(12) United States Patent
Wittle

(10) Patent No.: US 11,662,287 B2
(45) Date of Patent: May 30, 2023

(54) DEVICES AND METHODS FOR MONITORING

(71) Applicant: PRECISION FERMENTATION, INC., Durham, NC (US)

(72) Inventor: Eric Wittle, Chapel Hill, NC (US)

(73) Assignee: PRECISION FERMENTATION, INC., Durham, NC (US)

( * ) Notice: Subject to any disclaimer, the term of this patent is extended or adjusted under 35 U.S.C. 154(b) by 0 days.

(21) Appl. No.: 17/652,402

(22) Filed: Feb. 24, 2022

(65) Prior Publication Data

US 2022/0268679 A1 Aug. 25, 2022

Related U.S. Application Data

(60) Provisional application No. 63/153,177, filed on Feb. 24, 2021.

(51) Int. Cl.
*G01N 9/00* (2006.01)
*G01N 1/14* (2006.01)

(52) U.S. Cl.
CPC ............... *G01N 9/00* (2013.01); *G01N 1/14* (2013.01)

(58) Field of Classification Search
CPC ................................. G01N 9/00; G01N 1/14
USPC ........................................................ 73/32 R
See application file for complete search history.

(56) References Cited

U.S. PATENT DOCUMENTS

| | | | |
|---|---|---|---|
| 4,683,207 A * | 7/1987 | Waarvik | C12M 41/00 422/552 |
| 4,703,664 A * | 11/1987 | Kirkpatrick | E21B 21/08 73/866.5 |
| 6,190,914 B1 | 2/2001 | Grivell et al. | |
| 6,874,355 B2 | 4/2005 | Kornfeldt et al. | |
| 6,874,356 B2 | 4/2005 | Kornfeldt et al. | |
| 11,326,996 B2 | 5/2022 | Wells et al. | |
| 2002/0151700 A1 | 10/2002 | Farwick et al. | |
| 2004/0106170 A1 | 6/2004 | Kornfeldt et al. | |
| 2004/0112121 A1 | 6/2004 | Kornfeldt et al. | |
| 2008/0090047 A1 | 4/2008 | Kuroda et al. | |
| 2012/0077232 A1 * | 3/2012 | Budaraju | C12M 41/32 435/291.1 |
| 2012/0295338 A1 | 11/2012 | Reep et al. | |
| 2015/0291982 A1 | 10/2015 | Budaraju et al. | |
| 2019/0093065 A1 * | 3/2019 | Haase | C12M 41/32 |
| 2020/0292501 A1 * | 9/2020 | Wells | G01F 1/74 |

(Continued)

FOREIGN PATENT DOCUMENTS

| | | |
|---|---|---|
| CN | 207108972 | 3/2018 |
| WO | WO 03/029425 | 4/2003 |

(Continued)

OTHER PUBLICATIONS

Written Opinion cited in Application No. PCT/US/2022/070793 dated Jun. 9, 2022.

(Continued)

*Primary Examiner* — Marrit Eyassu
(74) *Attorney, Agent, or Firm* — DLA Piper LLP (US)

(57) ABSTRACT

Example monitoring devices, systems and methods for use are provided. The devices can comprise one or more paths. In an embodiment, a first fluid path is connected to a sensor manifold, the sensor manifold comprising one or more sensors for sensing one or more characteristics of a fluid, and a second fluid path connected to a second sensor component, the second sensor component comprising a density sensor for sensing the density of the fluid.

32 Claims, 89 Drawing Sheets

(56) References Cited

U.S. PATENT DOCUMENTS

2020/0294234 A1 9/2020 Rance et al.
2020/0319005 A1* 10/2020 Folgerø .................... G01N 9/24

FOREIGN PATENT DOCUMENTS

| WO | WO 2004/027092 | 4/2004 |
| WO | WO 2017096385 | 6/2017 |
| WO | WO 2019/067558 | 4/2019 |
| WO | WO-2019071385 A1 * | 4/2019 |

OTHER PUBLICATIONS

International Search Report cited in Application No. PCT/US/2022/070793 dated Jun. 9, 2022.
English Abstract of CN 207108972 published on Mar. 16, 2018.
Yokogawa Electric Corporation, "Automatic and Continuous Monitoring of the Beer Fermentation Process (with a Liquid Density Meter)", Yokogawa Homepage, 2022, 1-3 page, URL: https://www.yokogawa.com/library/resources/application-notes/automatic-and-continuous-monitoring-of-the-beer-fermentation-process-with-a-liquid-density-meter/.
International Search Report and "Written Opinion of the International Searching Authority" (ISA/US) in HAASE, Steven B., et al., International Patent Application Serial No. PCT/US2018/052881, dated Dec. 6, 2018 (36 pages).
Crowell, Chris, "First look: The BrewMonitor system automates, live-streams fermentation monitoring to any levice," Craft Brewing Business, Aug. 13, 2018, available at Internet webpage <https://www.craftbrewingbusiness. mm/news/6000-breweries-operational-US-brewers-association-releases-2017-craft-beer-review/2018/>, accessed Sep. 6, 2018. (5 pages).
McGoff, K.A., Guo, X., Deckard, A., Kelliher, C.M., Leman, A.R., Francey, L.J., Hogenesch, J.B., -IAASE, S.B., and Harer, J., "The Local Edge Machine: inference of dynamic models of gene regulation," Genome Siology 17:214, published Oct. 19, 2016 (13 pages).
S. M. G. Saerens et al. "Monitoring the influence of high-gravity brewing and fermentation temperature on flavour formation by analysis of gene expression levels in brewing yeast" Appl Microbiol Biotechnol (2008) 80:1039-1051 (Year: 2008).
Michael D.G. et al., "Model-based transcriptome engineering promotes a fermentative transcritional state in yeast", Proceedings of the National Academy of Sciences, vol. 113, No. 47, pps. (Nov. 3, 2016).
Written Opinion issued in European Application No. 18863516.3 dated May 26, 2021.
International Search Report issued European Application No. PCT/US22/070793 dated May 26, 2021.
U.S. Appl. No. 16/142,736 dated Dec. 28, 2022.
U.S. Appl. No. 16/142,736 dated Mar. 2, 2023 (for Jan. 30, 2022 to Mar. 2, 2023).

* cited by examiner

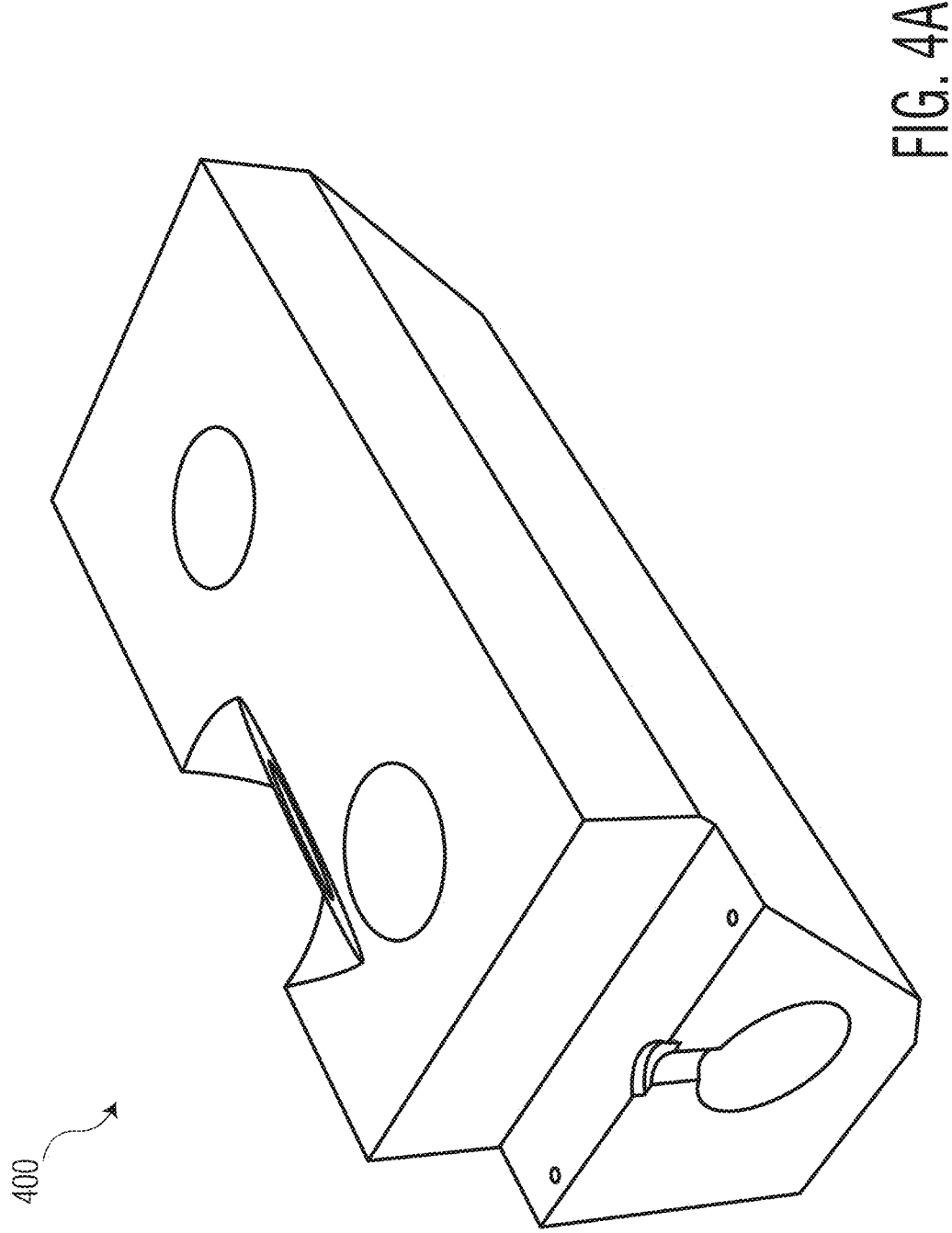

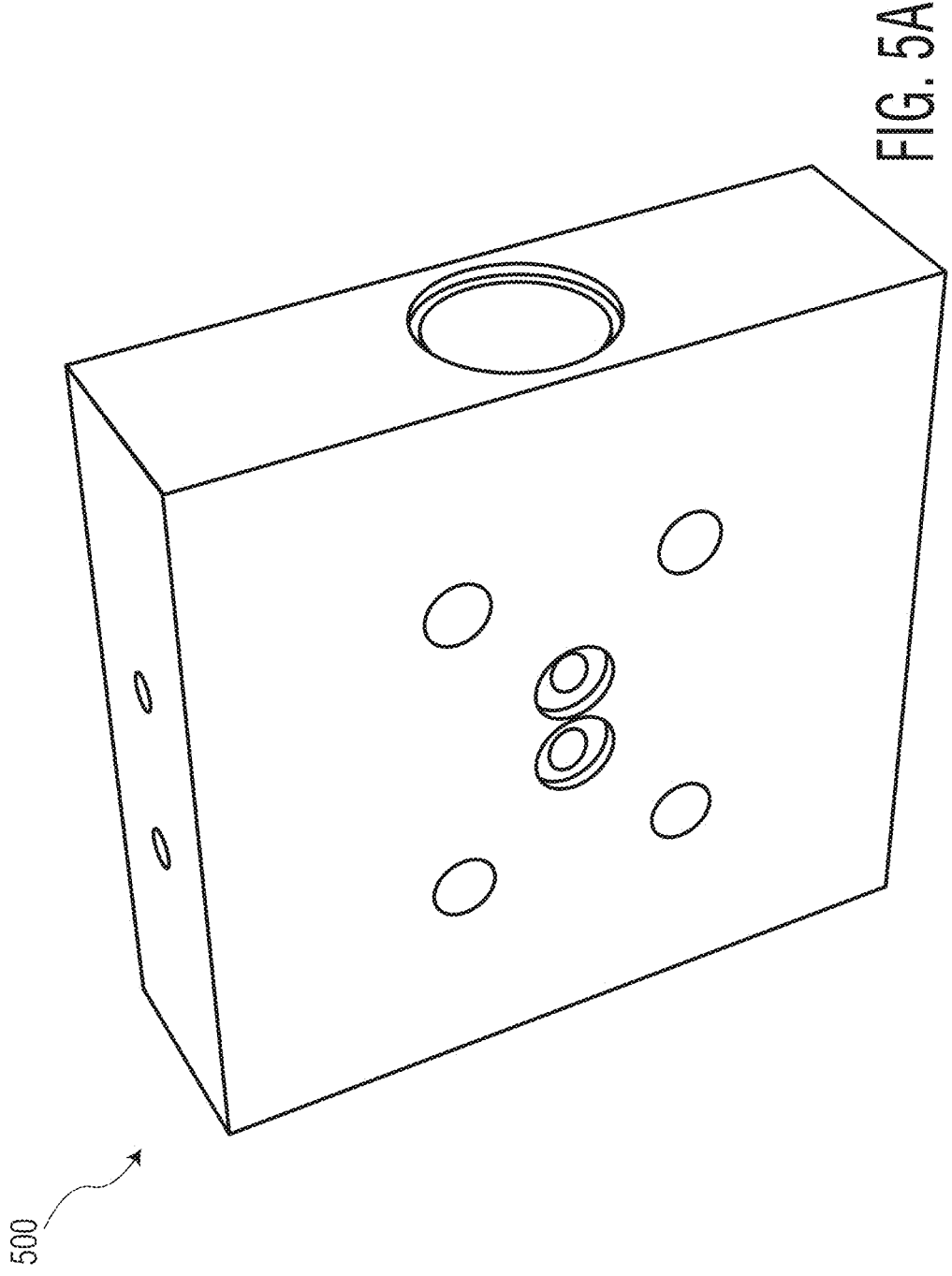

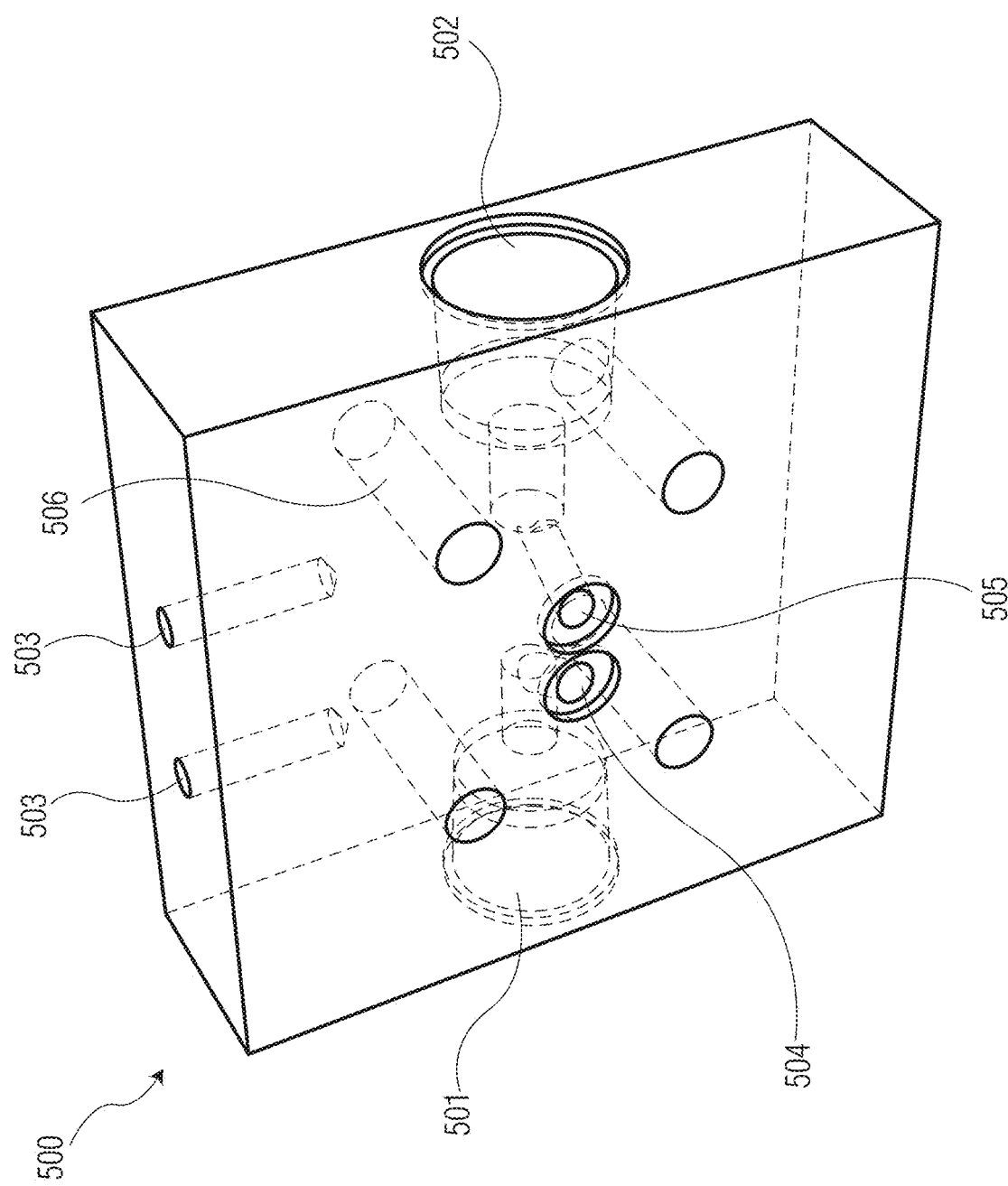

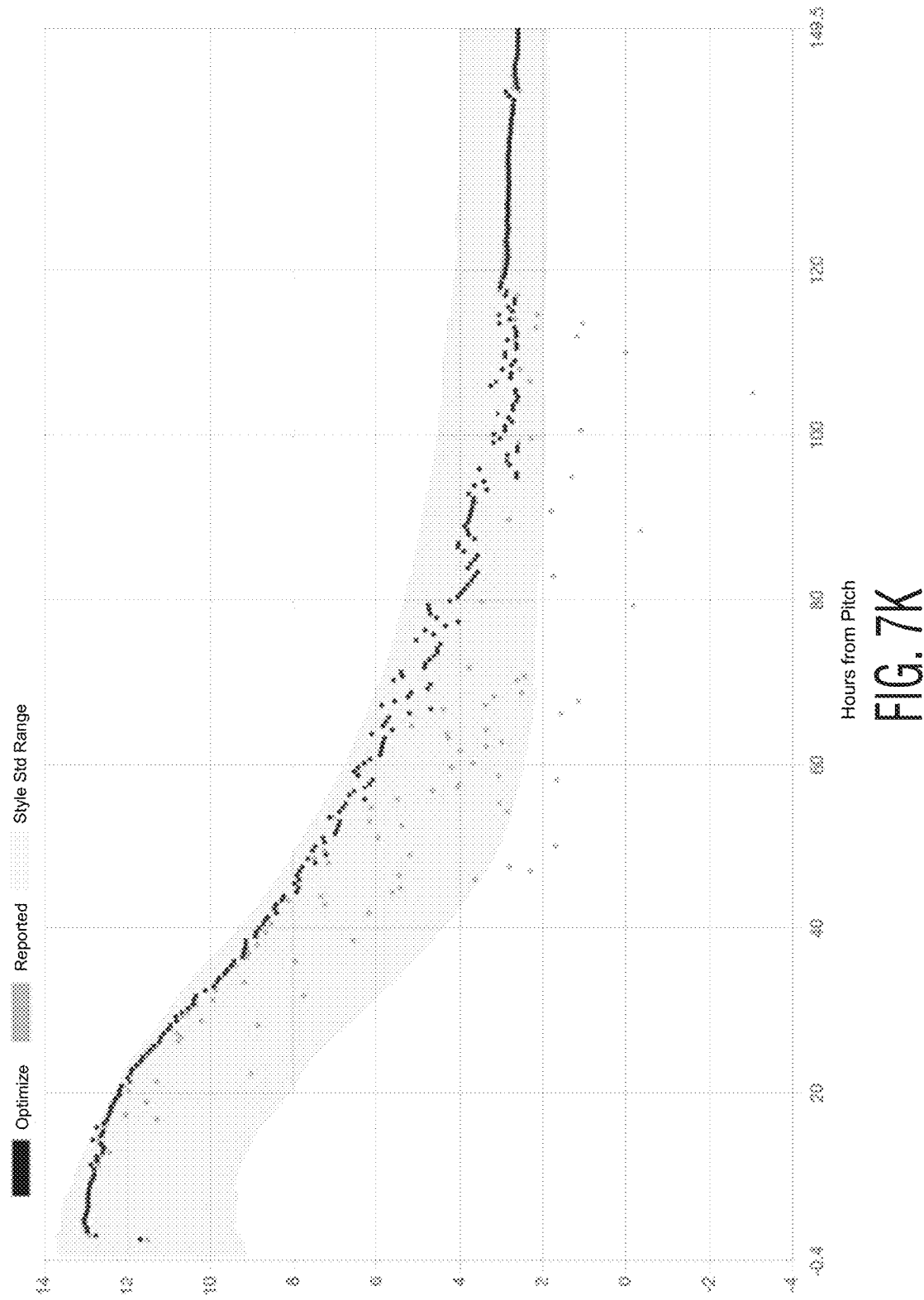

FIG. 7L

```
if not obs.rds_record('opt_plato') and obs.rds_record('obs_max') and not
issas(obs.rds_record('obs_max')):
    obs.rds_record('opt_plato') = obs.rds_record('obs_max')
    obs.properties('rules') += 'W'
```

FIG. 7N

```
curr_delta = cbs.prior_obs.rds_record['opt_pinto'] - cbs.rds_record['opt_pinto']
stream_delta = opt.prior_obs.rds_record['opt_pinto'] - cbs.rds_record['stream_max']
if (stream_delta > 0 and curr_delta < curr_delta) or \
   (stream_delta < 0 and curr_delta < stream_delta) or \
   (curr_delta < 0 and stream_delta > 0 \
    and stream_delta < opt.max_slope / 0):
    cbs.rds_record['opt_pinto'] = cbs.rds_record['stream_max']
    cbs.properties['rules'] += 'C'
```

FIG. 7P

```
if opt.p3_slope_ct > 0 and 's%' not in obs.properties('rules') \
    and not 'c%' in obs.properties('rules'):
    slope_est = opt.prior_obs.rds_record('opt_plato') + intervals * opt.p3_slope
    slope_key = 's'
    obs.properties('rules') += slope_key
    obs.rds_record('opt_plato') = round(slope_est,2)
```

FIG. 7R

| phase | hours_from_pitch | opt_plate | stream_max | rules | attenu-ation | dbs_max | dbs_valid | mode | pt_slope | pt_slope_sum | pt_slope_ct | rdng_density | rdng_ph | rdng_pressure | rdng_conductivity | rdng_do | rdng_temp_fld | std |
|---|---|---|---|---|---|---|---|---|---|---|---|---|---|---|---|---|---|---|
| 0 | 2.03 | 11.67 | | M | | 11.67 | 30 | 10.45 | | | | 1.045 | 5.23 | 0.215 | 2420 | 0.06 | 18.4 | 3.816 |
| | 2.20 | | | | | | | | | | | | 5.23 | 0.214 | 2429 | 0.06 | 18.3 | |
| | 2.37 | | | | | | | | | | | | 5.22 | 0.214 | 2432 | 0.06 | 18.2 | |
| 0 | 2.53 | 12.76 | 12.8 | 02 | -0.09 | 12.92 | 31 | 12.81 | | | | 1.051 | 5.21 | 0.214 | 2456 | 0.06 | 18.1 | 0.397 |
| | 2.70 | | | | | | | | | | | | 5.21 | 0.214 | 2465 | 0.06 | 18.1 | |
| | 2.87 | | | | | | | | | | | | 5.20 | 0.214 | 2462 | 0.06 | 18.1 | |
| 0 | 3.03 | 12.96 | 13 | 02 | -0.02 | 13.03 | 31 | 12.99 | | | | 1.051 | 5.20 | 0.213 | 2467 | 0.06 | 18.1 | 0.06 |
| | 3.20 | | | | | | | | | | | | 5.20 | 0.212 | 2466 | 0.06 | 18.1 | |
| | 3.37 | | | | | | | | | | | | 5.19 | 0.213 | 2470 | 0.06 | 18.1 | |
| 0 | 3.53 | 12.97 | 13 | 02 | -0 | 13.05 | 31 | 13.03 | | | | 1.051 | 5.18 | 0.212 | 2467 | 0.06 | 18.1 | 0.034 |
| | 3.70 | | | | | | | | | | | | 5.18 | 0.212 | 2470 | 0.06 | 18.0 | |
| | 3.87 | | | | | | | | | | | | 5.18 | 0.211 | 2472 | 0.06 | 18.1 | |
| 0 | 4.03 | 13.03 | 13 | 02 | -0.01 | 13.06 | 31 | 13.03 | | | | 1.052 | 5.16 | 0.210 | 2464 | 0.06 | 18.0 | 0.03 |
| | 4.20 | | | | | | | | | | | | 5.15 | 0.210 | 2466 | 0.06 | 18.0 | |
| | 4.37 | | | | | | | | | | | | 5.15 | 0.209 | 2465 | 0.06 | 18.0 | |
| 0 | 4.53 | 13.03 | 13 | 02 | | 13.06 | 31 | 13.05 | | | | 1.052 | 5.13 | 0.209 | 2464 | 0.06 | 18.0 | 0.031 |
| | 4.70 | | | | | | | | | | | | 5.14 | 0.210 | 2462 | 0.06 | 18.0 | |
| | 4.87 | | | | | | | | | | | | 5.13 | 0.210 | 2463 | 0.06 | 18.1 | |
| 0 | 5.03 | 13 | 13 | 0b | 0.002 | 13.02 | 31 | 13.00 | | | | 1.051 | 5.13 | 0.211 | 2462 | 0.06 | 18.1 | 0.008 |
| | 5.20 | | | | | | | | | | | | 5.13 | 0.211 | 2465 | 0.06 | 18.1 | |
| | 5.37 | | | | | | | | | | | | 5.13 | 0.213 | 2466 | 0.06 | 18.2 | |

| | | | | | | | | | | | | | | | | |
|---|---|---|---|---|---|---|---|---|---|---|---|---|---|---|---|---|
| 0 | 5.53 | 12.96 | 13 | 0b | 0.005 | 12.99 | 31 | 12.96 | | 1.051 | 5.12 | 0.213 | 2470 | 0.06 | 18.2 | 0.01 |
| | 5.70 | | | | | | | | | | 5.12 | 0.214 | 2472 | 0.06 | 18.2 | |
| | 5.87 | | | | | | | | | | 5.12 | 0.215 | 2472 | 0.06 | 18.3 | 0.015 |
| 0 | 6.03 | 12.94 | 13 | 0b | 0.007 | 12.96 | 31 | 12.94 | | 1.051 | 5.12 | 0.215 | 2474 | 0.06 | 18.3 | |
| | 6.20 | | | | | | | | | | 5.11 | 0.214 | 2480 | 0.06 | 18.2 | |
| | 6.37 | | | | | | | | | | 5.10 | 0.214 | 2484 | 0.06 | 18.2 | |
| 0 | 6.53 | 12.94 | 13 | 02 | 0.007 | 12.96 | 30 | 12.94 | | 1.051 | 5.10 | 0.214 | 2488 | 0.06 | 18.2 | 0.021 |
| | 6.70 | | | | | | | | | | 5.10 | 0.214 | 2492 | 0.06 | 18.2 | |
| | 6.87 | | | | | | | | | | 5.09 | 0.214 | 2499 | 0.06 | 18.1 | |
| 0 | 7.03 | 12.95 | 13 | 02 | 0.007 | 12.96 | 31 | 12.95 | | 1.051 | 5.09 | 0.213 | 2504 | 0.06 | 18.1 | 0.023 |
| | 7.20 | | | | | | | | | | 5.09 | 0.213 | 2506 | 0.06 | 18.0 | |
| | 7.37 | | | | | | | | | | 5.08 | 0.214 | 2505 | 0.06 | 18.0 | |
| 0 | 7.53 | 12.93 | 13 | 0b | 0.008 | 12.95 | 31 | 12.93 | | 1.051 | 5.08 | 0.214 | 2505 | 0.06 | 18.0 | 0.02 |
| | 7.70 | | | | | | | | | | 5.07 | 0.214 | 2505 | 0.06 | 18.0 | |
| | 7.87 | | | | | | | | | | 5.07 | 0.214 | 2504 | 0.06 | 18.1 | |
| 0 | 8.03 | 12.92 | 12.9 | 0b | 0.008 | 12.93 | 31 | 12.92 | | 1.051 | 5.06 | 0.214 | 2506 | 0.06 | 18.1 | 0.021 |
| | 8.20 | | | | | | | | | | 5.06 | 0.215 | 2508 | 0.06 | 18.1 | |
| | 8.37 | | | | | | | | | | 5.05 | 0.214 | 2509 | 0.06 | 18.1 | |
| 0 | 8.53 | 12.9 | 12.9 | 0b | 0.01 | 12.91 | 31 | 12.90 | | 1.051 | 5.05 | 0.214 | 2510 | 0.06 | 18.1 | 0.019 |
| | 8.70 | | | | | | | | | | 5.05 | 0.214 | 2512 | 0.06 | 18.1 | |
| | 8.87 | | | | | | | | | | 5.04 | 0.214 | 2519 | 0.06 | 18.1 | |
| 0 | 9.03 | 12.88 | 12.9 | 0b | 0.011 | 12.91 | 31 | 12.88 | | 1.051 | 5.04 | 0.214 | 2522 | 0.06 | 18.1 | 0.021 |
| | 9.20 | | | | | | | | | | 5.04 | 0.214 | 2522 | 0.06 | 18.1 | |
| | 9.37 | | | | | | | | | | 5.03 | 0.214 | 2526 | 0.06 | 18.1 | |
| 0 | 9.53 | 12.83 | 12.8 | 0b | 0.016 | 12.9 | 31 | 12.83 | | 1.051 | 5.02 | 0.214 | 2523 | 0.06 | 18.2 | 0.035 |

| | | | | | | | | | | | | | | | | | | | |
|---|---|---|---|---|---|---|---|---|---|---|---|---|---|---|---|---|---|---|---|
| 0 | 9.70 | | | | | | | | | | | | | | | | | | |
| | 9.87 | | | | | | | | | 5.02 | 0.214 | 2524 | 0.06 | 18.2 | |
| 0 | 10.03 | 12.79 | 12.9 | 02 | 0.018 | 12.88 | 30 | 12.79 | | | 5.01 | 0.214 | 2529 | 0.06 | 18.1 | 0.052 |
| | 10.20 | | | | | | | | | | 5.01 | 0.214 | 2530 | 0.06 | 18.1 | |
| 0 | 10.37 | 12.81 | 12.8 | 02 | 0.017 | 13.04 | 31 | 12.73 | | 1.05 | 5.01 | 0.214 | 2530 | 0.06 | 18.1 | 0.103 |
| | 10.53 | | | | | | | | | | 5.00 | 0.214 | 2529 | 0.06 | 18.1 | |
| 0 | 10.70 | 12.88 | 12.9 | 02 | 0.012 | 12.91 | 31 | 12.71 | | | 5.00 | 0.214 | 2530 | 0.06 | 18.1 | 0.136 |
| | 10.87 | | | | | | | | | 1.05 | 4.99 | 0.214 | 2530 | 0.06 | 18.1 | |
| 0 | 11.03 | 12.72 | 12.9 | Ob | 0.023 | 12.82 | 31 | 12.72 | | | 4.99 | 0.214 | 2530 | 0.06 | 18.1 | 0.133 |
| | 11.20 | | | | | | | | | | 4.98 | 0.214 | 2529 | 0.06 | 18.1 | |
| 0 | 11.37 | 12.74 | 12.8 | M | 0.022 | 12.74 | 30 | 12.62 | | 1.05 | 4.98 | 0.214 | 2529 | 0.06 | 18.1 | 0.253 |
| | 11.53 | | | | | | | | | | 4.97 | 0.214 | 2529 | 0.06 | 18.2 | |
| 0 | 11.70 | 12.6 | 12.8 | M | 0.033 | 12.6 | 31 | 12.38 | | | 4.97 | 0.214 | 2526 | 0.06 | 18.1 | 0.317 |
| | 11.87 | | | | | | | | | 1.05 | 4.96 | 0.214 | 2531 | 0.06 | 18.1 | |
| 0 | 12.03 | 12.58 | 12.7 | M | 0.035 | 12.58 | 31 | 12.45 | -0.02 | | 4.96 | 0.214 | 2531 | 0.06 | 18.1 | |
| | 12.20 | | | | | | | | | 1.049 | 4.95 | 0.214 | 2531 | 0.06 | 18.2 | |
| 1 | 12.37 | | | | | | | | -0.02 | | 4.95 | 0.214 | 2503 | 0.06 | 18.1 | 0.308 |
| | 12.53 | | | | | | | | | | 4.94 | 0.215 | 2394 | 0.06 | 18.2 | |
| 1 | 12.70 | 12.64 | 12.7 | M | 0.03 | 12.64 | 31 | 12.60 | 0 | 1 | 4.95 | 0.216 | 2418 | 0.06 | 18.3 | |
| | 12.87 | | | | | | | | | 1.049 | 4.94 | 0.215 | 2385 | 0.06 | 18.3 | |
| 1 | 13.03 | | | | | | | | 0 | | 4.94 | 0.215 | 2413 | 0.06 | 18.2 | 0.308 |
| | 13.20 | | | | | | | | | | 4.94 | 0.216 | 2403 | 0.06 | 18.3 | |
| 1 | 13.37 | | | | | | | | | 1.05 | 4.93 | 0.216 | 2376 | 0.06 | 18.3 | |
| | 13.53 | | | | | | | | 0 | 2 | 4.93 | 0.216 | 2411 | 0.06 | 18.2 | 0.079 |
| | 13.70 | | | | | | | | | | 4.93 | 0.213 | 2371 | 0.06 | 18.3 | |
| | | | | | | | | | | | | | 2378 | 0.06 | 18.2 | |

FIG. 8C

| | | | | | | | | | | | | | | | | |
|---|---|---|---|---|---|---|---|---|---|---|---|---|---|---|---|---|
| 13.87 | | | | | | | | | | | | | | | | |
| 14.03 | 12.83 | 12.7 | M | 0.015 | 12.83 | 31 | 12.62 | 0 | 0 | | | 4.93 | 0.213 | 2377 | 0.06 | 18.2 | 0.16 |
| 14.20 | | | | | | | | | | 3 | 1.05 | 4.93 | 0.214 | 2362 | 0.06 | 18.2 | |
| 14.37 | | | | | | | | | | | | 4.93 | 0.210 | 2364 | 0.06 | 18.2 | |
| 14.53 | 12.64 | 12.6 | M | 0.03 | 12.64 | 31 | 12.58 | 0 | 0 | | | 4.93 | 0.211 | 2363 | 0.06 | 18.2 | 0.329 |
| 14.70 | | | | | | | | | | 4 | 1.05 | 4.92 | 0.213 | 2356 | 0.06 | 18.2 | |
| 14.87 | | | | | | | | | | | | 4.92 | 0.210 | 2354 | 0.06 | 18.2 | |
| 15.03 | 12.59 | 12.6 | M | 0.034 | 12.59 | 31 | 12.58 | 0 | 0 | | | 4.92 | 0.209 | 2357 | 0.06 | 18.1 | 0.158 |
| 15.20 | | | | | | | | | | 5 | 1.05 | 4.92 | 0.212 | 2358 | 0.06 | 18.1 | |
| 15.37 | | | | | | | | | | | | 4.91 | 0.209 | 2355 | 0.06 | 18.1 | |
| 15.53 | 12.74 | 12.6 | M | 0.022 | 12.74 | 31 | 12.49 | 0.02 | 0 | | | 4.91 | 0.209 | 2360 | 0.06 | 18.1 | 0.546 |
| 15.70 | | | | | | | | | | 6 | 1.049 | 4.91 | 0.212 | 2352 | 0.06 | 18.1 | |
| 15.87 | | | | | | | | | | | | 4.91 | 0.211 | 2378 | 0.06 | 18.1 | |
| 16.03 | 12.57 | 12.5 | M | 0.035 | 12.57 | 30 | 12.45 | 0.02 | 0 | | | 4.91 | 0.210 | 2361 | 0.06 | 18.1 | 0.327 |
| 16.20 | | | | | | | | | | 7 | 1.049 | 4.91 | 0.211 | 2320 | 0.06 | 18.1 | |
| 16.37 | | | | | | | | | | | | 4.91 | 0.209 | 2354 | 0.06 | 18.1 | |
| 16.53 | 12.49 | 12.5 | M | 0.041 | 12.49 | 29 | 12.22 | 0 | 0 | | | 4.90 | 0.209 | 2354 | 0.06 | 18.2 | 0.819 |
| 16.70 | | | | | | | | | | 8 | 1.044 | 4.90 | 0.211 | 2321 | 0.06 | 18.1 | |
| 16.87 | | | | | | | | | | | | 4.90 | 0.208 | 2352 | 0.06 | 18.1 | |
| 17.03 | 12.45 | 12.5 | M | 0.045 | 12.45 | 26 | 12.24 | −0.01 | 0 | | | 4.90 | 0.209 | 2350 | 0.06 | 18.1 | 0.877 |
| 17.20 | | | | | | | | | | 9 | 1.047 | 4.90 | 0.211 | 2347 | 0.06 | 18.1 | |
| 17.37 | | | | | | | | | | | | 4.90 | 0.210 | 2346 | 0.06 | 18.1 | |
| 17.53 | 12.42 | 12.5 | M | 0.047 | 12.42 | 30 | 12.36 | −0.03 | 0 | | | 4.89 | 0.208 | 2339 | 0.06 | 18.1 | 0.435 |
| 17.70 | | | | | | | | | | 10 | 1.049 | 4.89 | 0.213 | 2337 | 0.06 | 18.1 | |
| 17.87 | | | | | | | | | | | | 4.89 | 0.209 | 2335 | 0.06 | 18.1 | |

| | | | | | | | | | | | | | | | | | | | |
|---|---|---|---|---|---|---|---|---|---|---|---|---|---|---|---|---|---|---|---|
| 1 | 18.03 | 12.4 | 12.4 | M | 0.048 | 12.4 | 31 | 12.33 | | | -0.05 | 11 | 1.049 | 4.89 | 0.212 | 2341 | 0.06 | 18.1 | 0.277 |
| | 18.20 | | | | | | | | | | | | | 4.89 | 0.208 | 2330 | 0.06 | 18.1 | |
| 1 | 18.37 | 12.3 | 12.33 | | | | | | | | | | | 4.89 | 0.208 | 2330 | 0.06 | 18.1 | 1.087 |
| | 18.53 | | 12.33 | M | 0.054 | 12.33 | 28 | 12.15 | -0.01 | | -0.07 | 12 | 1.045 | 4.88 | 0.211 | 2329 | 0.06 | 18.0 | |
| 1 | 18.70 | 12.3 | | | | | | | | | | | | 4.88 | 0.208 | 2330 | 0.06 | 18.1 | |
| | 18.87 | | | | | | | | | | | | | 4.88 | 0.209 | 2327 | 0.06 | 18.0 | 0.593 |
| 1 | 19.03 | 12.2 | 12.29 | M | 0.057 | 12.29 | 30 | 12.19 | -0.01 | | -0.1 | 13 | 1.048 | 4.88 | 0.211 | 2333 | 0.06 | 17.9 | |
| | 19.20 | | | | | | | | | | | | | 4.88 | 0.208 | 2326 | 0.06 | 18.0 | 0.813 |
| | 19.37 | | | | | | | | | | | | | 4.87 | 0.209 | 2352 | 0.06 | 18.0 | |
| 1 | 19.53 | 12.2 | 12.21 | M | 0.063 | 12.21 | 25 | 11.99 | -0.01 | | -0.12 | 14 | 1.048 | 4.87 | 0.210 | 2318 | 0.06 | 18.0 | |
| | 19.70 | | | | | | | | | | | | | 4.87 | 0.209 | 2335 | 0.06 | 18.0 | 0.306 |
| | 19.87 | | | | | | | | | | | | | 4.87 | 0.206 | 2320 | 0.06 | 17.9 | |
| 2 | 20.03 | 12.1 | 12.19 | M | 0.064 | 12.19 | 30 | 11.84 | -0.01 | | -0.15 | 15 | 1.047 | 4.87 | 0.207 | 2289 | 0.06 | 17.9 | |
| 2 | 20.20 | | | | | | | | | | | | | 4.86 | 0.205 | 2319 | 0.06 | 17.9 | 0.233 |
| 2 | 20.37 | | | | | | | | | | | | | 4.86 | 0.205 | 2318 | 0.06 | 17.9 | |
| 2 | 20.53 | 12.1 | 12.15 | M | 0.068 | 12.15 | 31 | 12.06 | -0.01 | | -0.18 | 16 | 1.048 | 4.86 | 0.207 | 2314 | 0.06 | 17.9 | |
| 2 | 20.70 | | | | | | | | | | | | | 4.86 | 0.205 | 2310 | 0.06 | 18.0 | 1.225 |
| 2 | 20.87 | | | | | | | | | | | | | 4.85 | 0.206 | 2311 | 0.06 | 17.9 | |
| 2 | 21.03 | 12.1 | 11.93 | M | 0.084 | 11.93 | 28 | 10.41 | -0.01 | | -0.22 | 17 | 1.044 | 4.85 | 0.207 | 2292 | 0.06 | 17.9 | |
| 2 | 21.20 | | | | | | | | | | | | | 4.85 | 0.205 | 2308 | 0.06 | 17.9 | |
| 2 | 21.37 | | | | | | | | | | | | | 4.85 | 0.205 | 2309 | 0.06 | 17.9 | 0.178 |
| 2 | 21.53 | 12.1 | 11.99 | M | 0.08 | 11.99 | 26 | 11.93 | -0.01 | | -0.25 | 18 | 1.047 | 4.85 | 0.207 | 2307 | 0.06 | 17.9 | |
| 2 | 21.70 | | | | | | | | | | | | | 4.84 | 0.205 | 2298 | 0.06 | 18.0 | |
| 2 | 21.87 | | | | | | | | | | | | | 4.84 | 0.205 | 2296 | 0.06 | 18.0 | |
| 2 | 22.03 | 12 | 11.9 | M | 0.087 | 11.9 | 29 | 11.36 | -0.02 | | -0.29 | 19 | 1.035 | 4.84 | 0.207 | 2249 | 0.06 | 18.1 | 2.401 |

FIG. 8F

| | | | | | | | | | | | | | | | | | | |
|---|---|---|---|---|---|---|---|---|---|---|---|---|---|---|---|---|---|---|
| 22.20 | | | | | | | | | | | | | | | 2282 | 0.06 | 18.0 | |
| 22.37 | | 11.87 | 11.9 | | | | | | | | | | 4.84 | 0.205 | 2274 | 0.06 | 18.1 | |
| 22.53 | 2 | | | | | | | | | | | | 4.84 | 0.204 | 2279 | 0.06 | 18.1 | 0.747 |
| 22.70 | | | | | | | | | | | | | 4.84 | 0.208 | 2280 | 0.06 | 18.1 | |
| 22.87 | | | | | | | | | | | | | 4.83 | 0.205 | 2278 | 0.06 | 18.1 | |
| 23.03 | 2 | 11.76 | 11.8 | M | 0.089 | 11.87 | 30 | 11.73 | -0.02 | -0.33 | 20 | 1.046 | 4.83 | 0.205 | 2265 | 0.06 | 18.2 | 0.357 |
| 23.20 | | | | | | | | | | | | | 4.83 | 0.208 | 2263 | 0.06 | 18.2 | |
| 23.37 | | | | | | | | | | | | | 4.83 | 0.204 | 2259 | 0.06 | 18.2 | |
| 23.53 | 2 | 11.66 | 11.7 | M | 0.097 | 11.76 | 30 | 11.63 | -0.02 | -0.37 | 21 | 1.046 | 4.83 | 0.205 | 2258 | 0.06 | 18.2 | 0.231 |
| 23.70 | | | | | | | | | | | | | 4.83 | 0.207 | 2263 | 0.06 | 18.1 | |
| 23.87 | | | | | | | | | | | | | 4.83 | 0.205 | 2248 | 0.06 | 18.2 | |
| 24.03 | 2 | 11.61 | 11.6 | Mt | 0.105 | 11.77 | 30 | 11.62 | -0.02 | -0.41 | 22 | 1.045 | 4.82 | 0.209 | 2250 | 0.06 | 18.3 | 1.164 |
| 24.20 | | | | | | | | | | | | | 4.82 | 0.204 | 2200 | 0.06 | 18.3 | |
| 24.37 | | | | | | | | | | | | | 4.82 | 0.204 | 2227 | 0.06 | 18.3 | |
| 24.53 | 2 | 11.51 | 11.5 | Mt | 0.109 | 11.56 | 30 | 11.40 | -0.02 | -0.45 | 23 | 1.045 | 4.82 | 0.207 | 2224 | 0.06 | 18.3 | 0.314 |
| 24.70 | | | | | | | | | | | | | 4.81 | 0.205 | 2231 | 0.06 | 18.2 | |
| 24.87 | | | | | | | | | | | | | 4.81 | 0.205 | 2235 | 0.06 | 18.3 | |
| 25.03 | 2 | 11.44 | | Mt | 0.117 | 11.47 | 25 | 11.31 | -0.02 | -0.5 | 24 | 1.045 | 4.81 | 0.207 | 2215 | 0.06 | 18.3 | 0.412 |
| 25.20 | | | 11.4 | | | | | | | | | | 4.81 | 0.205 | 2233 | 0.06 | 18.3 | |
| 25.37 | | | | | | | | | | | | | 4.81 | 0.205 | 2246 | 0.06 | 18.4 | |
| 25.53 | 2 | 11.35 | | Mt | 0.122 | 11.44 | 31 | 11.12 | -0.02 | -0.54 | 25 | 1.044 | 4.81 | 0.209 | 2241 | 0.06 | 18.3 | 0.994 |
| 25.70 | | | | | | | | | | | | | 4.81 | 0.205 | 2216 | 0.06 | 18.3 | |
| 25.87 | | | | | | | | | | | | | 4.81 | 0.204 | 2218 | 0.06 | 18.3 | |
| 26.03 | 2 | 11.22 | | M | 0.129 | 11.31 | 30 | 10.76 | -0.02 | -0.59 | 26 | 1.044 | 4.80 | 0.206 | 2203 | 0.06 | 18.3 | 1.645 |
| 26.20 | | | | | | | | | | | | | 4.80 | 0.205 | 2234 | 0.06 | 18.3 | |

| | | | | | | | | | | | | | | | | | | |
|---|---|---|---|---|---|---|---|---|---|---|---|---|---|---|---|---|---|---|
| 2 | 26.37 | | | | | | | | | | | | | | | | | |
| 2 | 26.53 | 11.18 | 11.2 | Mt | 0.142 | 11.05 | 27 | 10.65 | -0.02 | -0.69 | 28 | 1.041 | 4.80 | 0.204 | 2209 | 0.06 | 18.3 | 0.592 |
| | 26.70 | | | | | | | | | | | | 4.80 | 0.205 | 2207 | 0.06 | 18.4 | |
| | 26.87 | | | | | | | | | | | | 4.80 | 0.205 | 2225 | 0.06 | 18.3 | |
| 2 | 27.03 | 11.11 | 11.1 | Mt | 0.147 | 11.03 | 29 | 10.77 | -0.03 | -0.74 | 29 | 1.042 | 4.80 | 0.204 | 2209 | 0.06 | 18.3 | 1.12 |
| | 27.20 | | | | | | | | | | | | 4.79 | 0.204 | 2189 | 0.06 | 18.3 | |
| | 27.37 | | | | | | | | | | | | 4.79 | 0.205 | 2198 | 0.06 | 18.3 | |
| 2 | 27.53 | 11.01 | 11 | Mt | 0.155 | 10.95 | 29 | 10.88 | -0.03 | -0.8 | 30 | 1.042 | 4.79 | 0.205 | 2201 | 0.06 | 18.3 | 0.494 |
| | 27.70 | | | | | | | | | | | | 4.79 | 0.207 | 2201 | 0.06 | 18.3 | |
| | 27.87 | | | | | | | | | | | | 4.78 | 0.205 | 2203 | 0.06 | 18.3 | |
| 2 | 28.03 | 10.95 | 11 | Mt | 0.16 | 10.84 | 30 | 10.37 | -0.03 | -0.85 | 31 | 1.034 | 4.78 | 0.204 | 2175 | 0.06 | 18.3 | 1.376 |
| | 28.20 | | | | | | | | | | | | 4.78 | 0.207 | 2193 | 0.06 | 18.3 | |
| | 28.37 | | | | | | | | | | | | 4.78 | 0.204 | 2196 | 0.06 | 18.3 | |
| 2 | 28.53 | 10.81 | 10.8 | Mt | 0.17 | 10.75 | 27 | 10.15 | -0.03 | -0.91 | 32 | 1.039 | 4.78 | 0.205 | 2184 | 0.06 | 18.3 | 1.059 |
| | 28.70 | | | | | | | | | | | | 4.77 | 0.207 | 2210 | 0.06 | 18.3 | |
| | 28.87 | | | | | | | | | | | | 4.77 | 0.204 | 2204 | 0.06 | 18.3 | |
| 2 | 29.03 | 10.83 | | M | 0.169 | 10.83 | 30 | 10.59 | -0.03 | -0.96 | 33 | 1.041 | 4.77 | 0.206 | 2166 | 0.06 | 18.3 | 0.634 |
| | 29.20 | | | | | | | | | | | | 4.77 | 0.203 | 2188 | 0.06 | 18.3 | |
| | 29.37 | | | | | | | | | | | | 4.77 | 0.204 | 2189 | 0.06 | 18.3 | |
| 2 | 29.53 | 10.68 | 10.7 | Mt | 0.18 | 10.57 | 25 | 10.43 | -0.03 | -1.02 | 34 | 1.041 | 4.77 | 0.206 | 2185 | 0.06 | 18.3 | 0.775 |
| | 29.70 | | | | | | | | | | | | 4.77 | 0.205 | 2199 | 0.06 | 18.3 | |
| | 29.87 | | | | | | | | | | | | 4.76 | 0.205 | 2197 | 0.06 | 18.3 | |
| 2 | 30.03 | 10.54 | | M | 0.191 | 10.54 | 31 | 10.31 | -0.03 | -1.08 | 35 | 1.04 | 4.76 | 0.206 | 2203 | 0.06 | 18.3 | 0.591 |
| | 30.20 | | | | | | | | | | | | 4.76 | 0.204 | 2180 | 0.06 | 18.3 | |
| | 30.37 | | | | | | | | | | | | 4.76 | 0.204 | 2165 | 0.06 | 18.3 | |

| | | | | | | | | | | | | | | | | | | |
|---|---|---|---|---|---|---|---|---|---|---|---|---|---|---|---|---|---|---|
| 2 | 30.53 | 10.42 | 10.4 | Mt | 0.2 | 10.38 | 31 | 10.27 | -0.03 | -1.14 | 36 | 1.04 | 4.76 | 0.206 | 2186 | 0.06 | 18.3 | 1.154 |
| 2 | 30.70 | | | | | | | | | | | | | 0.203 | 2178 | 0.06 | 18.3 | |
| 2 | 30.87 | | | | | | | | | | | | 4.76 | 0.204 | 2156 | 0.06 | 18.3 | |
| 2 | 31.03 | 10.39 | 10.4 | Mt | 0.203 | 10.97 | 22 | 9.51 | -0.03 | -1.2 | 37 | 1.038 | 4.76 | 0.205 | 2171 | 0.06 | 18.3 | 1.963 |
| 2 | 31.20 | | | | | | | | | | | | 4.75 | 0.203 | 2144 | 0.06 | 18.3 | |
| 2 | 31.37 | | | | | | | | | | | | | 0.204 | 2200 | 0.06 | 18.3 | |
| 2 | 31.53 | 10.35 | 10.4 | Mt | 0.206 | 10.13 | 27 | 9.37 | -0.03 | -1.26 | 38 | 1.029 | 4.75 | 0.206 | 2180 | 0.06 | 18.3 | 1.517 |
| 2 | 31.70 | | | | | | | | | | | | 4.75 | 0.204 | 2187 | 0.06 | 18.2 | |
| 2 | 31.87 | | | | | | | | | | | | | 0.203 | 2180 | 0.06 | 18.3 | |
| 2 | 32.03 | 10.17 | 10.2 | Mt | 0.219 | 10.09 | 28 | 9.74 | -0.03 | -1.32 | 39 | 1.039 | 4.75 | 0.206 | 2174 | 0.06 | 18.3 | 1.319 |
| 2 | 32.20 | | | | | | | | | | | | 4.74 | 0.204 | 2177 | 0.06 | 18.3 | |
| 2 | 32.37 | | | | | | | | | | | | 4.74 | 0.203 | 2161 | 0.06 | 18.3 | |
| 2 | 32.53 | 10.08 | 10.1 | Mt | 0.226 | 10.02 | 27 | 9.76 | -0.03 | -1.38 | 40 | 1.037 | 4.74 | 0.205 | 2155 | 0.06 | 18.3 | 1.308 |
| 2 | 32.70 | | | | | | | | | | | | 4.74 | 0.203 | 2172 | 0.06 | 18.3 | |
| 2 | 32.87 | | | | | | | | | | | | 4.74 | 0.203 | 2148 | 0.06 | 18.3 | |
| 2 | 33.03 | 9.92 | | M | 0.239 | 9.92 | 29 | 9.89 | -0.04 | -1.45 | 41 | 1.038 | 4.73 | 0.206 | 2168 | 0.06 | 18.3 | 0.403 |
| 2 | 33.20 | | | | | | | | | | | | 4.73 | 0.203 | 2163 | 0.06 | 18.1 | |
| 2 | 33.37 | | | | | | | | | | | | 4.73 | 0.204 | 2192 | 0.06 | 18.2 | |
| 2 | 33.53 | 9.84 | 9.96 | M | 0.245 | 9.84 | 30 | 9.49 | -0.04 | -1.51 | 42 | 1.035 | 4.73 | 0.205 | 2139 | 0.06 | 18.2 | 0.961 |
| 2 | 33.70 | | | | | | | | | | | | 4.73 | 0.203 | 2159 | 0.06 | 18.2 | |
| 2 | 33.87 | | | | | | | | | | | | | 0.203 | 2167 | 0.06 | 18.2 | |
| 2 | 34.03 | 9.8 | 9.8 | Mt | 0.248 | 9.76 | 31 | 9.62 | -0.04 | -1.58 | 43 | 1.037 | 4.72 | 0.206 | 2161 | 0.06 | 18.3 | 0.494 |
| 2 | 34.20 | | | | | | | | | | | | 4.72 | 0.205 | 2199 | 0.06 | 18.2 | |
| 2 | 34.37 | | | | | | | | | | | | 4.72 | 0.202 | 2170 | 0.06 | 18.2 | |
| 2 | 34.53 | 9.66 | | M | 0.259 | 9.66 | 31 | 9.62 | -0.04 | -1.64 | 44 | 1.037 | 4.72 | 0.206 | 2172 | 0.06 | 18.2 | 0.496 |

FIG. 8I

| C1 | C2 | C3 | C4 | C5 | C6 | C7 | C8 | C9 | C10 | C11 | C12 | C13 | C14 | C15 | C16 | C17 | C18 | C19 |
|----|------|------|------|-----|-------|------|----|------|-------|-------|----|-------|------|-------|------|------|------|-------|
| 2  | 34.70 |      |      |     |       |      |    |      |       |       |    |       |      |       |      |      |      |       |
|    | 34.87 | 9.61 | 9.66 |     |       |      |    |      |       |       |    |       |      |       |      |      |      |       |
| 2  | 35.03 |      |      | M   | 0.262 | 9.61 | 30 | 9.49 | -0.04 | -1.71 | 45 | 1.037 | 4.72 | 0.203 | 2169 | 0.06 | 18.1 | 0.734 |
|    | 35.20 |      |      |     |       |      |    |      |       |       |    |       | 4.72 | 0.203 | 2182 | 0.06 | 18.2 |       |
| 2  | 35.37 | 9.51 |      |     |       |      |    |      |       |       |    |       | 4.71 | 0.207 | 2177 | 0.06 | 18.1 | 0.959 |
|    | 35.53 |      |      | M   | 0.27  | 9.51 | 27 | 9.35 | -0.04 | -1.78 | 46 |       | 4.71 | 0.203 | 2179 | 0.06 | 18.1 |       |
|    | 35.70 |      |      |     |       |      |    |      |       |       |    | 1.036 | 4.71 | 0.203 | 2158 | 0.06 | 18.2 |       |
| 2  | 35.87 | 9.44 | 9.47 |     |       |      |    |      |       |       |    |       | 4.71 | 0.206 | 2153 | 0.06 | 18.2 | 1.123 |
|    | 36.03 |      |      | M   | 0.276 | 9.44 | 30 | 9.09 | -0.04 | -1.84 | 47 |       | 4.71 | 0.202 | 2155 | 0.06 | 18.1 |       |
|    | 36.20 |      |      |     |       |      |    |      |       |       |    | 1.03  | 4.70 | 0.203 | 2169 | 0.06 | 18.1 |       |
| 2  | 36.37 | 9.24 | 9.49 |     |       |      |    |      |       |       |    |       | 4.70 | 0.205 | 2163 | 0.06 | 18.2 | 1.507 |
|    | 36.53 |      |      | M   | 0.291 | 9.24 | 28 | 8.82 | -0.04 | -1.91 | 48 |       | 4.70 | 0.202 | 2163 | 0.06 | 18.1 |       |
|    | 36.70 |      |      |     |       |      |    |      |       |       |    | 1.035 | 4.70 | 0.201 | 2156 | 0.06 | 18.1 |       |
| 2  | 36.87 | 9.21 | 9.31 |     |       |      |    |      |       |       |    |       | 4.70 | 0.204 | 2144 | 0.06 | 18.1 | 0.716 |
|    | 37.03 |      |      | M   | 0.293 | 9.21 | 30 | 8.79 | -0.04 | -1.98 | 49 |       | 4.70 | 0.203 | 2176 | 0.06 | 18.1 |       |
|    | 37.20 |      |      |     |       |      |    |      |       |       |    | 1.035 | 4.70 | 0.202 | 2173 | 0.06 | 18.1 |       |
| 2  | 37.37 | 9.18 | 42.8 |     |       |      |    |      |       |       |    |       | 4.70 | 0.205 | 2150 | 0.06 | 18.1 | 0.303 |
|    | 37.53 |      |      | M   | 0.295 | 9.18 | 28 | 9.11 | -0.04 | -2.05 | 50 |       | 4.69 | 0.202 | 2151 | 0.06 | 18.1 |       |
|    | 37.70 |      |      |     |       |      |    |      |       |       |    | 1.034 | 4.69 | 0.202 | 2147 | 0.06 | 18.1 |       |
| 2  | 37.87 | 9.16 | 9.16 |     |       |      |    |      |       |       |    |       | 4.69 | 0.205 | 2148 | 0.06 | 18.1 | 1.416 |
|    | 38.03 |      |      | M   | 0.297 | 9.16 | 27 | 8.31 | -0.04 | -2.12 | 51 |       | 4.69 | 0.202 | 2142 | 0.06 | 18.1 |       |
|    | 38.20 |      |      |     |       |      |    |      |       |       |    |       | 4.69 | 0.201 | 2142 | 0.06 | 18.1 |       |
| 2  | 38.37 | 9.16 |      |     |       |      |    |      |       |       |    | 1.025 | 4.69 | 0.204 | 2141 | 0.06 | 18.1 | 1.58  |
|    | 38.53 |      |      | MSm | 0.297 | 8.45 | 26 | 7.19 | -0.04 | -2.19 | 52 |       | 4.69 | 0.205 | 2152 | 0.06 | 18.1 |       |
|    | 38.70 |      |      |     |       |      |    |      |       |       |    |       | 4.69 | 0.201 | 2128 | 0.06 | 18.1 |       |

| | | | | | | | | | | | | | | | | | |
|---|---|---|---|---|---|---|---|---|---|---|---|---|---|---|---|---|---|
| 2 | 38.87 | 8.91 | | | | | | | | | | 4.68 | 0.203 | 2142 | 0.06 | 18.0 | |
| | 39.03 | 8.91 | 9.1 | M | 0.316 | 8.91 | 31 | 8.47 | -0.04 | -2.26 | 53 | 1.034 | 4.68 | 0.204 | 2144 | 0.06 | 18.1 | 1.151 |
| | 39.20 | 8.88 | 8.9 | | | | | | | | | | 4.68 | 0.202 | 2122 | 0.06 | 18.1 | |
| 2 | 39.37 | 8.88 | 8.9 | | | | | | | | | | 4.68 | 0.202 | 2129 | 0.06 | 18.1 | |
| | 39.53 | 8.81 | 8.93 | M | 0.318 | 8.88 | 29 | 8.64 | -0.04 | -2.32 | 54 | 1.033 | 4.68 | 0.204 | 2133 | 0.06 | 18.1 | 0.49 |
| | 39.70 | | | | | | | | | | | | 4.68 | 0.202 | 2141 | 0.06 | 18.1 | |
| 2 | 39.87 | 8.81 | 8.9 | | | | | | | | | | 4.68 | 0.202 | 2137 | 0.06 | 18.0 | |
| | 40.03 | 8.71 | 8.93 | M | 0.324 | 8.81 | 26 | 8.74 | -0.04 | -2.39 | 55 | 1.034 | 4.68 | 0.205 | 2130 | 0.06 | 18.1 | 0.951 |
| | 40.20 | | | | | | | | | | | | 4.68 | 0.202 | 2131 | 0.06 | 18.1 | |
| 2 | 40.37 | 8.71 | 8.9 | | | | | | | | | | 4.68 | 0.202 | 2152 | 0.06 | 18.0 | |
| | 40.53 | 8.67 | 3.71 | M | 0.332 | 8.71 | 23 | 8.25 | -0.04 | -2.46 | 56 | 1.033 | 4.68 | 0.204 | 2118 | 0.06 | 18.1 | 1.643 |
| | 40.70 | | | | | | | | | | | | 4.67 | 0.201 | 2146 | 0.06 | 18.1 | |
| 2 | 40.87 | 8.67 | 8.55 | | | | | | | | | | 4.67 | 0.201 | 2117 | 0.06 | 18.0 | |
| | 41.03 | 8.62 | 8.55 | M | 0.335 | 8.67 | 28 | 8.30 | -0.04 | -2.53 | 57 | 1.033 | 4.67 | 0.206 | 2119 | 0.06 | 18.1 | 1.263 |
| | 41.20 | | | | | | | | | | | | 4.67 | 0.201 | 2129 | 0.06 | 18.0 | |
| 2 | 41.37 | 8.62 | 8.6 | | | | | | | | | | 4.67 | 0.201 | 2134 | 0.06 | 18.1 | |
| | 41.53 | 8.39 | 8.6 | M | 0.338 | 8.62 | 31 | 8.32 | -0.04 | -2.6 | 58 | 1.033 | 4.67 | 0.205 | 2111 | 0.06 | 18.0 | 1.111 |
| | 41.70 | | | | | | | | | | | | 4.67 | 0.201 | 2109 | 0.06 | 18.1 | |
| 2 | 41.87 | 8.39 | 8.6 | | | | | | | | | | 4.67 | 0.200 | 2119 | 0.06 | 17.9 | |
| | 42.03 | 8.39 | 8.63 | M | 0.356 | 8.39 | 25 | 7.76 | -0.05 | -2.67 | 59 | 1.023 | 4.67 | 0.203 | 2139 | 0.06 | 18.0 | 1.54 |
| | 42.20 | | | | | | | | | | | | 4.66 | 0.201 | 2084 | 0.06 | 18.0 | |
| 2 | 42.37 | 8.45 | 8.63 | | | | | | | | | | 4.66 | 0.200 | 2140 | 0.06 | 18.1 | |
| | 42.53 | 8.45 | | M | 0.351 | 8.45 | 27 | 8.28 | -0.05 | -2.74 | 60 | 1.032 | 4.66 | 0.205 | 2141 | 0.06 | 17.9 | 0.891 |
| | 42.70 | | | | | | | | | | | | 4.66 | 0.202 | 2139 | 0.06 | 17.9 | |
| | 42.87 | | | | | | | | | | | | 4.66 | 0.201 | | | | |

| | | | | | | | | | | | | | | | | | | |
|---|---|---|---|---|---|---|---|---|---|---|---|---|---|---|---|---|---|---|
| 2 | 43.03 | 8.41 | 8.37 | M | 0.355 | 8.41 | 31 | 7.60 | -0.05 | -2.81 | 61 | 1.027 | 4.66 | 0.204 | 2134 | 0.06 | 17.9 | 0.627 |
| 2 | 43.20 | 8.27 | | | | | | | | | | | 4.66 | 0.201 | 2139 | 0.06 | 18.0 | |
| 2 | 43.37 | | | | | | | | | | | | 4.66 | 0.201 | 2105 | 0.06 | 18.0 | |
| 2 | 43.53 | 8.27 | 8.64 | M | 0.365 | 8.27 | 31 | 7.14 | -0.05 | -2.88 | 62 | 1.031 | 4.66 | 0.204 | 2111 | 0.06 | 18.0 | 0.702 |
| 2 | 43.70 | | | | | | | | | | | | 4.66 | 0.200 | 2108 | 0.06 | 18.1 | |
| 2 | 43.87 | | | | | | | | | | | | 4.66 | 0.200 | 2110 | 0.06 | 18.1 | |
| 2 | 44.03 | 8.23 | 8.42 | M | 0.368 | 8.23 | 30 | 7.49 | -0.05 | -2.95 | 63 | 1.028 | 4.66 | 0.204 | 2112 | 0.06 | 18.1 | 0.802 |
| 2 | 44.20 | | | | | | | | | | | | 4.66 | 0.200 | 2103 | 0.06 | 18.2 | |
| 2 | 44.37 | | | | | | | | | | | | 4.66 | 0.200 | 2104 | 0.06 | 18.3 | |
| 2 | 44.53 | 7.92 | 8.33 | M | 0.392 | 7.92 | 19 | 6.92 | -0.05 | -3.02 | 64 | 1.021 | 4.66 | 0.205 | 2091 | 0.06 | 18.3 | 1.25 |
| 2 | 44.70 | | | | | | | | | | | | 4.66 | 0.200 | 2087 | 0.06 | 18.3 | |
| 2 | 44.87 | | | | | | | | | | | | 4.66 | 0.201 | 2098 | 0.06 | 18.1 | |
| 2 | 45.03 | 7.87 | | Ms | 0.396 | 7.92 | 18 | 6.36 | -0.05 | -3.09 | 65 | 1.02 | 4.66 | 0.204 | 2092 | 0.06 | 18.3 | 1.392 |
| 2 | 45.20 | | | | | | | | | | | | 4.66 | 0.201 | 2115 | 0.06 | 18.3 | |
| 2 | 45.37 | | | | | | | | | | | | 4.66 | 0.200 | 2092 | 0.06 | 18.3 | |
| 2 | 45.53 | 7.97 | 8.21 | M | 0.388 | 7.97 | 27 | 7.68 | -0.05 | -3.16 | 66 | 1.03 | 4.66 | 0.203 | 2113 | 0.06 | 18.3 | 0.973 |
| 2 | 45.70 | | | | | | | | | | | | 4.66 | 0.202 | 2116 | 0.06 | 18.2 | |
| 2 | 45.87 | | | | | | | | | | | | 4.66 | 0.200 | 2106 | 0.06 | 18.3 | |
| 2 | 46.03 | 7.86 | 8.25 | M | 0.397 | 7.86 | 23 | 7.12 | -0.05 | -3.24 | 67 | 1.013 | 4.65 | 0.204 | 2123 | 0.06 | 18.4 | 1.57 |
| 2 | 46.20 | | | | | | | | | | | | 4.66 | 0.200 | 2096 | 0.06 | 18.3 | |
| 2 | 46.37 | | | | | | | | | | | | 4.65 | 0.201 | 2102 | 0.06 | 18.3 | |
| 2 | 46.53 | 7.91 | 7.91 | MSm | 0.393 | 7.13 | 21 | 6.69 | -0.05 | -3.3 | 68 | 1.02 | 4.65 | 0.205 | 2097 | 0.06 | 18.4 | 1.119 |
| 2 | 46.70 | | | | | | | | | | | | 4.66 | 0.201 | 2103 | 0.06 | 18.3 | |
| 2 | 46.87 | | | | | | | | | | | | 4.65 | 0.201 | 2102 | 0.06 | 18.3 | |
| 2 | 47.03 | 7.85 | | MSq | 0.398 | 7.12 | 10 | 6.28 | -0.05 | -3.37 | 69 | 1.007 | 4.65 | 0.205 | 2102 | 0.06 | 18.3 | 1.492 |

| | | | | | | | | | | | | | | | | |
|---|---|---|---|---|---|---|---|---|---|---|---|---|---|---|---|---|
| 2 | 47.20 | | | | | | | | | | | | | | | |
| | 47.37 | 7.78 | | | | | | | | | | | | 18.3 | | |
| | 47.53 | | | | | | | | | | 4.65 | 0.202 | 2094 | 0.06 | 18.3 | 1.597 |
| 2 | 47.70 | | | | | | | | | | 4.65 | 0.202 | 2117 | 0.06 | 18.4 | |
| | 47.87 | | | | | | | | | | 4.65 | 0.204 | 2090 | 0.06 | 18.3 | |
| | 48.03 | 7.47 | | M | 0.403 | 7.78 | 16 | 7.33 | -0.08 | -4.48 | 4.65 | 0.202 | 2132 | 0.06 | 18.3 | 1.139 |
| 2 | 48.20 | | | | | | | | | | 4.65 | 0.200 | 2070 | 0.06 | 18.4 | |
| | 48.37 | | | | | | | | | | 4.65 | 0.205 | 2067 | 0.06 | 18.4 | |
| | 48.53 | 7.65 | | M | 0.427 | 7.47 | 24 | 7.13 | -0.08 | -4.55 | 4.65 | 0.200 | 2084 | 0.06 | 18.3 | 0.789 |
| 2 | 48.70 | | | | | | | | | 1.009 | 4.65 | 0.200 | 2047 | 0.06 | 18.4 | |
| | 48.87 | | | | | | | | | | 4.65 | 0.204 | 2077 | 0.06 | 18.3 | |
| | 49.03 | 7.22 | | M | 0.413 | 7.65 | 25 | 7.43 | -0.08 | -4.62 | 4.65 | 0.201 | 2095 | 0.06 | 18.4 | 0.948 |
| 2 | 49.20 | | | | | | | | | 1.027 | 4.65 | 0.199 | 2072 | 0.06 | 18.3 | |
| | 49.37 | | | | | | | | | | 4.65 | 0.205 | 2100 | 0.06 | 18.4 | |
| | 49.53 | 7.54 | | M | 0.446 | 7.22 | 24 | 6.57 | -0.08 | -4.69 | 4.65 | 0.201 | 2104 | 0.06 | 18.4 | 0.672 |
| 2 | 49.70 | | | | | | | | | 1.028 | 4.65 | 0.201 | 1901 | 0.06 | 18.5 | |
| | 49.87 | | 7.55 | | | | | | | | 4.65 | 0.204 | 2058 | 0.06 | 18.5 | |
| | 50.03 | 7.47 | | M | 0.421 | 7.54 | 28 | 7.31 | -0.08 | -4.76 | 4.65 | 0.200 | 2088 | 0.06 | 18.6 | 1.034 |
| 2 | 50.20 | | | | | | | | | 1.019 | 4.65 | 0.198 | 1997 | 0.06 | 18.6 | |
| | 50.37 | | | | | | | | | | 4.64 | 0.205 | 2074 | 0.06 | 18.6 | |
| | 50.53 | 7.25 | | MSm | 0.427 | 5.65 | 9 | 5.21 | -0.08 | -4.83 | 4.65 | 0.201 | 2010 | 0.06 | 18.4 | 1.415 |
| 2 | 50.70 | | 7.47 | M- | 0.444 | 7.25 | 9 | 5.42 | -0.08 | -4.9 | 4.65 | 0.200 | 1843 | 0.06 | 18.6 | |
| | 50.87 | | | | | | | | | 1.027 | 4.65 | 0.206 | 2081 | 0.06 | 18.5 | |
| | 51.03 | 7.29 | | M | 0.441 | 7.29 | 27 | 6.96 | -0.08 | -4.97 | 4.65 | 0.199 | 2078 | 0.06 | 18.5 | 0.629 |
| 2 | 51.20 | | | | | | | | | 1.022 | 4.64 | 0.201 | 1953 | 0.06 | 18.5 | |
| | | | | | | | | | | | 4.65 | 0.205 | 2081 | 0.06 | 18.5 | |
| | | | | | | | | | | | 4.64 | 0.200 | 2079 | 0.06 | 18.5 | |

| | | | | | | | | | | | | | | | | | | | |
|---|---|---|---|---|---|---|---|---|---|---|---|---|---|---|---|---|---|---|---|
| 2 | 51.37 | | | | | | | | | | | | 4.64 | 0.200 | 2050 | 0.06 | 18.6 | |
| 2 | 51.53 | 7 | 7.17 | M- | 0.463 | 7 | 18 | 6.45 | -0.08 | -5.04 | 64 | | 4.64 | 0.205 | 2082 | 0.06 | 18.5 | 1.061 |
| 2 | 51.70 | | | | | | | | | | | | 4.64 | 0.200 | 2088 | 0.06 | 18.5 | |
| 2 | 51.87 | | | | | | | | | | | | 4.64 | 0.198 | 1602 | 0.06 | 18.5 | |
| 2 | 52.03 | 6.96 | | MSsq* | 0.466 | 5.79 | 5 | 5.62 | -0.08 | -5.11 | 65 | | 4.64 | 0.206 | 2084 | 0.06 | 18.6 | 0.764 |
| 2 | 52.20 | | | | | | | | | | | | 4.64 | 0.200 | 2030 | 0.06 | 18.5 | |
| 2 | 52.37 | | | | | | | | | | | | 4.64 | 0.199 | 1917 | 0.06 | 18.6 | |
| 2 | 52.53 | 6.92 | | Mq* | 0.469 | 6.79 | 13 | 6.50 | -0.08 | -5.19 | 66 | 1.019 | 4.64 | 0.206 | 2083 | 0.06 | 18.6 | 0.867 |
| 2 | 52.70 | | | | | | | | | | | | 4.64 | 0.201 | 2103 | 0.06 | 18.6 | |
| 2 | 52.87 | | | | | | | | | | | | 4.64 | 0.198 | 1709 | 0.06 | 18.6 | |
| 2 | 53.03 | 6.89 | | M | 0.471 | 6.89 | 20 | 6.38 | -0.08 | -5.37 | 67 | 1.023 | 4.64 | 0.204 | 2070 | 0.06 | 18.6 | 0.871 |
| 2 | 53.20 | | | | | | | | | | | | 4.64 | 0.201 | 2043 | 0.06 | 18.5 | |
| 2 | 53.37 | | | | | | | | | | | | 4.64 | 0.199 | 2071 | 0.06 | 18.4 | |
| 2 | 53.53 | 7.13 | 7.4 | M | 0.453 | 7.13 | 25 | 6.98 | -0.08 | -5.44 | 68 | 1.026 | 4.64 | 0.207 | 2085 | 0.06 | 18.6 | 0.478 |
| 2 | 53.70 | | | | | | | | | | | | 4.64 | 0.199 | 2086 | 0.06 | 18.5 | |
| 2 | 53.87 | | | | | | | | | | | | 4.64 | 0.198 | 1863 | 0.06 | 18.5 | |
| 2 | 54.03 | 6.9 | | M | 0.47 | 6.9 | 15 | 6.46 | -0.08 | -5.51 | 69 | 1.009 | 4.64 | 0.205 | 2113 | 0.06 | 18.6 | 1.171 |
| 2 | 54.20 | | | | | | | | | | | | 4.64 | 0.200 | 1986 | 0.06 | 18.5 | |
| 2 | 54.37 | | | | | | | | | | | | 4.63 | 0.201 | 2102 | 0.06 | 18.4 | |
| 2 | 54.53 | 6.82 | | M | 0.477 | 6.82 | 30 | 6.36 | -0.08 | -5.57 | 70 | 1.023 | 4.64 | 0.206 | 2071 | 0.06 | 18.6 | 0.852 |
| 2 | 54.70 | | | | | | | | | | | | 4.64 | 0.201 | 2085 | 0.06 | 18.4 | |
| 2 | 54.87 | | 6.97 | | | | | | | | | | 4.63 | 0.200 | 2063 | 0.06 | 18.5 | |
| 2 | 55.03 | 6.75 | | M | 0.482 | 6.75 | 12 | 6.47 | -0.08 | -5.64 | 71 | 1.01 | 4.64 | 0.204 | 2093 | 0.06 | 18.6 | 1.469 |
| 2 | 55.20 | | | | | | | | | | | | 4.63 | 0.201 | 2091 | 0.06 | 18.5 | |
| 2 | 55.37 | | | | | | | | | | | | 4.63 | 0.201 | 2097 | 0.06 | 18.4 | |

| | | | | | | | | | | | | | | | | | | |
|---|---|---|---|---|---|---|---|---|---|---|---|---|---|---|---|---|---|---|
| 2 | 55.53 | 6.3 | | M | 0.517 | 6.3 | 10 | 6.02 | -0.08 | -5.72 | 72 | 1.02 | 4.63 | 0.207 | 2065 | 0.06 | 18.6 | 1.268 |
| | 55.70 | | | | | | | | | | | | 4.63 | 0.199 | 2064 | 0.06 | 18.6 | |
| | 55.87 | | | | | | | | | | | | 4.63 | 0.199 | 2007 | 0.06 | 18.6 | |
| 2 | 56.03 | 6.66 | | M- | 0.489 | 6.66 | 6 | 6.32 | -0.08 | -5.79 | 73 | | 4.63 | 0.204 | 2075 | 0.06 | 18.6 | 0.166 |
| | 56.20 | | | | | | | | | | | | 4.63 | 0.200 | 2016 | 0.06 | 18.6 | |
| | 56.37 | | | | | | | | | | | | 4.63 | 0.199 | 2039 | 0.06 | 18.5 | |
| 2 | 56.53 | 6.55 | | M | 0.497 | 6.55 | 11 | 6.21 | -0.08 | -5.85 | 74 | 1.016 | 4.63 | 0.206 | 2076 | 0.06 | 18.6 | 1.305 |
| | 56.70 | | | | | | | | | | | | 4.63 | 0.201 | 2105 | 0.06 | 18.6 | |
| | 56.87 | | | | | | | | | | | | 4.63 | 0.201 | 1583 | 0.06 | 18.7 | |
| 2 | 57.03 | 6.3 | | M | 0.517 | 6.3 | 15 | 5.43 | -0.08 | -5.92 | 75 | 1.014 | 4.63 | 0.207 | 2075 | 0.06 | 18.6 | 1.116 |
| | 57.20 | | | | | | | | | | | | 4.63 | 0.199 | 2067 | 0.06 | 18.5 | |
| | 57.37 | | | | | | | | | | | | 4.63 | 0.198 | 1839 | 0.06 | 18.7 | |
| 2 | 57.53 | 6.18 | | M | 0.526 | 6.18 | 14 | 5.79 | -0.08 | -6 | 76 | 1.014 | 4.63 | 0.205 | 2070 | 0.06 | 18.6 | 1.132 |
| | 57.70 | | | | | | | | | | | | 4.63 | 0.200 | 2088 | 0.06 | 18.6 | |
| | 57.87 | | | | | | | | | | | | 4.63 | 0.200 | 1606 | 0.06 | 18.7 | |
| 2 | 58.03 | 6.1 | | MSs | 0.532 | 5.12 | 9 | 3.24 | -0.08 | -6.07 | 77 | 1.005 | 4.63 | 0.205 | 2070 | 0.06 | 18.6 | 0.836 |
| | 58.20 | | | | | | | | | | | | 4.63 | 0.200 | 2073 | 0.06 | 18.5 | |
| | 58.37 | | | | | | | | | | | | 4.63 | 0.199 | 2009 | 0.06 | 18.6 | |
| 2 | 58.53 | 6.46 | | M | 0.504 | 6.46 | 14 | 5.92 | -0.07 | -5.8 | 78 | 1.01 | 4.63 | 0.203 | 2074 | 0.06 | 18.8 | 0.55 |
| | 58.70 | | | | | | | | | | | | 4.63 | 0.200 | 1853 | 0.06 | 18.7 | |
| | 58.87 | | | | | | | | | | | | 4.63 | 0.201 | 1218 | 0.06 | 18.6 | |
| 2 | 59.03 | 6.55 | | M | 0.497 | 6.55 | 27 | 6.26 | -0.07 | -5.86 | 79 | 1.024 | 4.63 | 0.205 | 2094 | 0.06 | 18.6 | 0.647 |
| | 59.20 | | | | | | | | | | | | 4.63 | 0.200 | 2094 | 0.06 | 18.6 | |
| | 59.37 | | | | | | | | | | | | 4.63 | 0.199 | 2009 | 0.06 | 18.7 | |
| 2 | 59.53 | 6.46 | 6.46 | MSm | 0.504 | 5.55 | 17 | 5.09 | -0.07 | -5.93 | 80 | 1.015 | 4.62 | 0.205 | 2048 | 0.06 | 18.8 | 0.905 |

FIG. 8N

| | | | | | | | | | | | | | | | | |
|---|---|---|---|---|---|---|---|---|---|---|---|---|---|---|---|---|
| 59.70 | | | | | | | | | | | | | | | | |
| 59.87 | 6.31 | | | | | | | | | | | | | | | |
| 2 | 60.03 | | MSsq* | 0.516 | 5.63 | 10 | 5.27 | -0.07 | -5.99 | 81 | 1.013 | 4.63 | 0.200 | 2087 | 0.06 | 18.7 | |
| | 60.20 | | | | | | | | | | | 4.63 | 0.200 | 1673 | 0.06 | 18.9 | 0.835 |
| | 60.37 | 6.17 | | | | | | | | | | 4.62 | 0.205 | 2065 | 0.06 | 18.8 | |
| 2 | 60.53 | | M | 0.526 | 6.17 | 4 | 4.51 | -0.07 | -6.09 | 82 | | 4.63 | 0.199 | 2021 | 0.06 | 18.7 | |
| | 60.70 | | | | | | | | | | | 4.62 | 0.199 | 1633 | 0.06 | 18.9 | 1.004 |
| | 60.87 | 5.89 | | | | | | | | | | 4.62 | 0.206 | 2068 | 0.06 | 18.8 | |
| 2 | 61.03 | | M | 0.548 | 5.89 | 7 | 5.66 | -0.07 | -6.16 | 83 | | 4.62 | 0.200 | 2075 | 0.06 | 18.7 | |
| | 61.20 | | | | | | | | | | | 4.62 | 0.199 | 1981 | 0.06 | 18.9 | 0.401 |
| | 61.37 | 5.87 | | | | | | | | | | 4.62 | 0.204 | 2067 | 0.06 | 18.8 | |
| 2 | 61.53 | | MSsq* | 0.55 | 4.82 | 12 | 3.74 | -0.07 | -6.23 | 84 | 1.014 | 4.62 | 0.200 | 1975 | 0.06 | 18.9 | |
| | 61.70 | | | | | | | | | | | 4.62 | 0.199 | 1167 | 0.06 | 18.8 | 0.604 |
| | 61.87 | 5.85 | | | | | | | | | | 4.62 | 0.203 | 2050 | 0.06 | 18.9 | |
| 2 | 62.03 | | Mq* | 0.551 | 5.44 | 13 | 4.37 | -0.07 | -6.3 | 85 | 1.011 | 4.62 | 0.199 | 2026 | 0.06 | 18.8 | |
| | 62.20 | | | | | | | | | | | 4.62 | 0.199 | 1792 | 0.06 | 18.8 | 0.757 |
| | 62.37 | 5.83 | | | | | | | | | | 4.62 | 0.205 | 2041 | 0.06 | 18.8 | |
| 2 | 62.53 | | Mq* | 0.553 | 5.49 | 11 | 5.09 | -0.07 | -6.37 | 86 | 1.01 | 4.62 | 0.201 | 2062 | 0.06 | 18.7 | |
| | 62.70 | | | | | | | | | | | 4.62 | 0.199 | 1730 | 0.06 | 19.0 | 0.869 |
| | 62.87 | 5.79 | | | | | | | | | | 4.62 | 0.206 | 2058 | 0.06 | 18.9 | |
| 2 | 63.03 | | M | 0.556 | 5.79 | 8 | 4.01 | -0.07 | -6.47 | 87 | 1.015 | 4.62 | 0.200 | 2052 | 0.05 | 18.7 | |
| | 63.20 | | | | | | | | | | | 4.62 | 0.200 | 1040 | 0.06 | 18.9 | 0.884 |
| | 63.37 | 6.13 | | | | | | | | | | 4.62 | 0.204 | 2057 | 0.06 | 18.8 | |
| 2 | 63.53 | | M | 0.53 | 6.13 | 10 | 4.36 | -0.07 | -6.53 | 88 | 1.015 | 4.62 | 0.200 | 2052 | 0.06 | 18.9 | |
| | 63.70 | | | | | | | | | | | 4.62 | 0.204 | 1305 | 0.06 | 18.9 | 0.83 |
| | | | | | | | | | | | | 4.62 | 0.199 | 2063 | 0.06 | 18.8 | |
| | | | | | | | | | | | | 4.62 | | 2051 | 0.06 | 18.8 | |

| | | | | | | | | | | | | | | | | | |
|---|---|---|---|---|---|---|---|---|---|---|---|---|---|---|---|---|---|
| 2 | 63.87 | | | | | | | | | | | | 0.198 | 2055 | 0.06 | 18.9 | |
| 2 | 64.03 | 5.61 | M | 0.569 | 5.61 | 14 | 4.75 | -0.07 | -6.6 | 89 | 1.011 | 4.62 | 0.204 | 2080 | 0.06 | 19.0 | 0.725 |
| 2 | 64.20 | | | | | | | | | | | 4.62 | 0.199 | 2028 | 0.06 | 18.9 | |
| 2 | 64.37 | | | | | | | | | | | | 0.201 | 1840 | 0.06 | 18.8 | 0.686 |
| 2 | 64.53 | 5.83 | M | 0.553 | 5.83 | 18 | 5.19 | -0.07 | -6.66 | 90 | 1.018 | 4.62 | 0.204 | 2090 | 0.06 | 18.9 | |
| 2 | 64.70 | | | | | | | | | | | 4.62 | 0.200 | 2092 | 0.06 | 18.8 | |
| 2 | 64.87 | 5.76 | MSs- | 0.558 | 5.12 | 7 | | | | | | 4.61 | 0.198 | 2003 | 0.06 | 19.1 | 0.805 |
| 2 | 65.03 | 5.69 | M | 0.563 | 5.69 | 3 | 4.70 | -0.07 | -6.73 | 91 | | 4.61 | 0.203 | 2111 | 0.06 | 19.0 | |
| 2 | 65.20 | | | | | | | | | | | 4.62 | 0.200 | 1922 | 0.06 | 18.9 | |
| 2 | 65.37 | | | | | | | | | | | | 0.199 | 2036 | 0.06 | 18.9 | 1.255 |
| 2 | 65.53 | 5.2 | M | 0.601 | 5.2 | 6 | 4.34 | -0.07 | -6.79 | 92 | | 4.62 | 0.205 | 2079 | 0.06 | 18.9 | |
| 2 | 65.70 | | | | | | | | | | | 4.61 | 0.199 | 2058 | 0.06 | 18.8 | |
| 2 | 65.87 | | | | | | | | | | | 4.62 | 0.199 | 2054 | 0.06 | 18.9 | 0.598 |
| 2 | 66.03 | 4.692 | Mo | 0.64 | 5.77 | 14 | 5.01 | -0.07 | -6.86 | 93 | 1.004 | 4.61 | 0.205 | 2100 | 0.06 | 18.9 | |
| 2 | 66.20 | | | | | | | | | | | 4.61 | 0.198 | 2064 | 0.06 | 19.1 | |
| 2 | 66.37 | | | | | | | | | | | 4.61 | 0.198 | 1616 | 0.06 | 19.0 | 0.828 |
| 2 | 66.53 | 5.86 | M | 0.55 | 5.86 | 14 | 4.69 | -0.07 | -6.94 | 94 | 1.015 | 4.61 | 0.203 | 2088 | 0.06 | 19.1 | |
| 2 | 66.70 | | | | | | | | | | | 4.61 | 0.197 | 1924 | 0.06 | 19.1 | |
| 2 | 66.87 | | | | | | | | | | | | 0.200 | 1651 | 0.06 | 19.1 | 0.907 |
| 2 | 67.03 | 5.86 | M | 0.574 | 5.01 | 7 | 3.21 | -0.07 | -6.39 | 95 | 1.011 | 4.61 | 0.204 | 2084 | 0.06 | 19.0 | |
| 2 | 67.20 | | | | | | | | | | | 4.61 | 0.198 | 2023 | 0.06 | 19.0 | |
| 2 | 67.37 | | | | | | | | | | | | 0.199 | 1421 | 0.06 | 18.9 | 0.441 |
| 2 | 67.53 | 5.55 | MSsq* | | | | 4.10 | -0.07 | -6.45 | 96 | 1.002 | 4.61 | 0.204 | 2107 | 0.06 | 18.9 | |
| 2 | 67.70 | | | | | | | | | | | 4.61 | 0.198 | 2080 | 0.06 | 18.9 | |
| | 67.87 | | | | | | | | | | | 4.61 | 0.198 | 1545 | 0.06 | 18.9 | |

FIG. 8Q

| 2 | 68.03 | 5.23 |     | 0.599 | 5.23 | 13 | 4.82 | -0.07 | -7.03 | 97  | 1.01  | 4.61 | 0.204 | 2116 | 0.06 | 18.9 | 0.542 |
| - | ----- | ---- | --- | ----- | ---- | -- | ---- | ----- | ----- | --- | ----- | ---- | ----- | ---- | ---- | ---- | ----- |
| 2 | 68.20 |      |     |       |      |    |      |       |       |     |       | 4.61 | 0.199 | 2042 | 0.06 | 18.9 |       |
|   | 68.37 |      |     |       |      |    |      |       |       |     |       | 4.61 | 0.199 | 1657 | 0.06 | 18.9 |       |
| 2 | 68.53 | 5.16 |     | 0.604 | 4.16 | 3  | 3.37 | -0.07 | -7.09 | 98  | 1.008 | 4.61 | 0.205 | 2085 | 0.06 | 18.9 | 0.491 |
|   | 68.70 |      |     |       |      |    |      |       |       |     |       | 4.61 | 0.199 | 2067 | 0.05 | 18.9 |       |
|   | 68.87 |      |     |       |      |    |      |       |       |     |       | 4.61 | 0.195 | 1960 | 0.05 | 19.2 |       |
| 2 | 69.03 | 4.77 | M   | 0.634 | 4.77 | 3  | 4.63 | -0.07 | -7.16 | 99  |       | 4.61 | 0.201 | 2106 | 0.06 | 18.8 | 0.509 |
|   | 69.20 |      |     |       |      |    |      |       |       |     |       | 4.61 | 0.198 | 2027 | 0.06 | 18.8 |       |
|   | 69.37 |      |     |       |      |    |      |       |       |     |       | 4.61 | 0.199 | 1638 | 0.05 | 18.9 |       |
| 2 | 69.53 | 4.7  | MSs | 0.639 | 4.06 | 1  |      | -0.07 | -7.23 | 100 | 1.008 | 4.61 | 0.206 | 2102 | 0.06 | 18.8 |       |
|   | 69.70 |      |     |       |      |    |      |       |       |     |       | 4.61 | 0.199 | 2079 | 0.06 | 18.7 |       |
|   | 69.87 |      |     |       |      |    |      |       |       |     |       | 4.61 | 0.198 | 1932 | 0.06 | 18.7 |       |
| 2 | 70.03 | 5.58 | M   | 0.572 | 5.58 | 15 | 5.36 | -0.07 | -6.67 | 101 | 1.008 | 4.61 | 0.203 | 2089 | 0.06 | 18.6 | 0.906 |
|   | 70.20 |      |     |       |      |    |      |       |       |     |       | 4.61 | 0.198 | 2039 | 0.06 | 18.6 |       |
|   | 70.37 |      |     |       |      |    |      |       |       |     |       | 4.61 | 0.198 | 1877 | 0.06 | 18.6 |       |
| 2 | 70.53 | 5.37 | M   | 0.588 | 5.37 | 6  | 3.30 | -0.07 | -6.73 | 102 | 1.008 | 4.61 | 0.202 | 2076 | 0.06 | 18.7 | 0.978 |
|   | 70.70 |      |     |       |      |    |      |       |       |     |       | 4.61 | 0.199 | 2103 | 0.06 | 18.6 |       |
|   | 70.87 |      |     |       |      |    |      |       |       |     |       | 4.60 | 0.199 | 1957 | 0.06 | 18.6 |       |
| 2 | 71.03 | 5.4  | M   | 0.586 | 5.4  | 2  | 4.55 | -0.07 | -6.79 | 103 |       | 4.60 | 0.205 | 2110 | 0.06 | 18.6 | 1.556 |
|   | 71.20 |      |     |       |      |    |      |       |       |     |       | 4.60 | 0.197 | 2050 | 0.06 | 18.6 |       |
|   | 71.37 |      |     |       |      |    |      |       |       |     |       | 4.60 | 0.198 | 1235 | 0.06 | 18.7 |       |
| 2 | 71.53 | 4.84 | M   | 0.629 | 4.84 | 9  |      | -0.07 | -6.86 | 104 | 1.013 | 4.60 | 0.205 | 1961 | 0.06 | 18.6 | 0.68  |
|   | 71.70 |      |     |       |      |    |      |       |       |     |       | 4.60 | 0.196 | 2073 | 0.06 | 18.8 |       |
|   | 71.87 |      |     |       |      |    |      |       |       |     |       | 4.60 | 0.197 | 1810 | 0.06 | 18.8 |       |
| 2 | 72.03 | 4.82 | M   | 0.63  | 4.82 | 3  | 4.46 | -0.07 | -6.93 | 105 |       | 4.60 | 0.204 | 2114 | 0.06 | 18.7 | 0.959 |

| | | | | | | | | | | | | | | |
|---|---|---|---|---|---|---|---|---|---|---|---|---|---|---|
| 72.20 | | | | | | | | | 4.60 | 0.197 | 2067 | 0.06 | 18.8 | |
| 72.37 | | | | | | | | | 4.60 | 0.198 | 1629 | 0.06 | 18.6 | |
| 72.53 | 4.72 | Ssq* | 0.638 | | 0 | | -0.07 | -6.99 | 4.60 | 0.205 | 2092 | 0.06 | 18.6 | |
| 72.70 | | | | | | | | | 4.60 | 0.199 | 2091 | 0.06 | 18.6 | |
| 72.87 | | | | | | | | | 4.60 | 0.197 | 1981 | 0.06 | 18.8 | |
| 73.03 | 4.62 | MSsq* | 0.645 | 3.72 | 1 | | -0.07 | -7.06 | 4.60 | 0.205 | 2124 | 0.06 | 18.6 | |
| 73.20 | | | | | | | | | 4.60 | 0.196 | 2057 | 0.06 | 18.8 | |
| 73.37 | | | | | | | | | 4.60 | 0.196 | 1778 | 0.06 | 18.8 | 0.91 |
| 73.53 | 4.53 | M | 0.652 | 4.53 | 6 | 3.80 | -0.07 | -7.73 | 4.60 | 0.204 | 2089 | 0.06 | 18.5 | |
| 73.70 | | | | | | | | | 4.60 | 0.196 | 1942 | 0.06 | 18.6 | 0.976 |
| 73.87 | | | | | | | | | 4.60 | 0.198 | 1874 | 0.06 | 18.5 | |
| 74.03 | 4.54 | M | 0.652 | 4.54 | 7 | 4.21 | -0.07 | -7.79 | 4.60 | 0.203 | 2080 | 0.06 | 18.6 | |
| 74.20 | | | | | | | | | 4.60 | 0.197 | 2079 | 0.06 | 18.6 | |
| 74.37 | | | | | | | | | 4.60 | 0.197 | 1907 | 0.06 | 18.7 | |
| 74.53 | 4.46 | M | 0.658 | 4.46 | 1 | | -0.07 | -7.86 | 4.60 | 0.206 | 2101 | 0.06 | 18.6 | |
| 74.70 | | | | | | | | | 4.60 | 0.196 | 2077 | 0.06 | 18.6 | 0.085 |
| 74.87 | | | | | | | | | 4.60 | 0.198 | 1990 | 0.06 | 18.8 | |
| 75.03 | 5.04 | M | 0.613 | 5.04 | 3 | 5.01 | -0.07 | -7.92 | 4.60 | 0.203 | 2128 | 0.06 | 18.6 | |
| 75.20 | | | | | | | | | 4.60 | 0.196 | 2027 | 0.06 | 18.6 | 0.15 |
| 75.37 | | | | | | | | | 4.60 | 0.197 | 806 | 0.05 | 18.7 | |
| 75.53 | 4.62 | M | 0.645 | 4.62 | 3 | 4.39 | -0.07 | -7.98 | 4.60 | 0.203 | 2074 | 0.05 | 18.6 | |
| 75.70 | | | | | | | | | 4.60 | 0.195 | 2068 | 0.05 | 18.8 | |
| 75.87 | | | | | | | | | 4.60 | 0.199 | 1484 | 0.05 | 18.6 | 1.018 |
| 76.03 | 4.82 | M | 0.63 | 4.82 | 5 | 4.42 | -0.07 | -8.04 | 4.60 | 0.203 | 2077 | 0.06 | 18.6 | |
| 76.20 | | | | | | | | | 4.60 | 0.198 | 2077 | 0.06 | 18.6 | |

| | | | | M | | | | | | | | | | | | | | |
|---|---|---|---|---|---|---|---|---|---|---|---|---|---|---|---|---|---|---|
| | 76.37 | | | | | | | | | | | | 4.60 | 0.197 | 1821 | 0.06 | 18.7 | 0.675 |
| 3 | 76.53 | 4.34 | | M | 0.667 | 4.34 | 6 | 4.16 | | | | | 4.60 | 0.204 | 2105 | 0.05 | 18.5 | |
| | 76.70 | | | | | | | | −0.07 | −8.11 | 114 | | 4.59 | 0.197 | 2084 | 0.05 | 18.6 | |
| | 76.87 | | | | | | | | | | | | 4.60 | 0.196 | 759 | 0.05 | 18.7 | |
| 3 | 77.03 | 4.04 | | M | 0.69 | 4.04 | 1 | | −0.07 | −8.17 | 115 | | 4.59 | 0.203 | 2118 | 0.05 | 18.7 | |
| | 77.20 | | | | | | | | | | | | 4.60 | 0.196 | 2076 | 0.05 | 18.6 | |
| | 77.37 | | | | | | | 4.28 | −0.07 | −8.24 | 116 | | 4.59 | 0.196 | 1862 | 0.05 | 18.6 | 0.245 |
| 3 | 77.53 | 4.56 | | M | 0.65 | 4.56 | 6 | | | | | | 4.59 | 0.204 | 2087 | 0.06 | 18.6 | |
| | 77.70 | | | | | | | 4.47 | −0.07 | −8.3 | 117 | | 4.59 | 0.196 | 1926 | 0.05 | 18.6 | |
| | 77.87 | | | | | | | | | | | | 4.59 | 0.197 | 1927 | 0.05 | 18.7 | 0.302 |
| 3 | 78.03 | 4.7 | | M | 0.639 | 4.7 | 5 | | −0.07 | −8.36 | 118 | | 4.59 | 0.200 | 2088 | 0.05 | 18.5 | |
| | 78.20 | | | | | | | | | | | 0.998 | 4.59 | 0.196 | 2037 | 0.05 | 18.7 | |
| | 78.37 | | | | | | | | −0.07 | −8.41 | 119 | | 4.59 | 0.197 | 1928 | 0.05 | 18.6 | |
| 3 | 78.53 | 4.73 | | M | 0.637 | 4.73 | 1 | | | | | | 4.59 | 0.203 | 2024 | 0.05 | 18.7 | |
| | 78.70 | | | | | | | | | | | | 4.59 | 0.197 | 2076 | 0.05 | 18.8 | |
| | 78.87 | | | | | | | | −0.07 | −8.48 | 120 | 1.012 | 4.59 | 0.196 | 2064 | 0.06 | 18.6 | |
| 3 | 79.03 | 4.75 | | M | 0.635 | 4.75 | 2 | 3.45 | | | | | 4.59 | 0.202 | 2068 | 0.06 | 18.7 | 0.445 |
| | 79.20 | | | | | | | | | | | | 4.59 | 0.198 | 2044 | 0.06 | 18.6 | |
| | 79.37 | | | | | | | | −0.07 | −8.54 | 121 | | 4.59 | 0.196 | 2061 | 0.06 | 18.7 | |
| 3 | 79.53 | 4.24 | | M | 0.675 | 4.24 | 12 | | | | | | 4.59 | 0.203 | 2091 | 0.06 | 18.6 | 0.571 |
| | 79.70 | | | | | | | | | | | | 4.59 | 0.196 | 2060 | 0.06 | 18.8 | |
| | 79.87 | | | | | | | | | | | | 4.59 | 0.197 | 2012 | 0.05 | 18.8 | |
| 3 | 80.03 | 4.05 | | M | 0.689 | 4.05 | 1 | | | | | | 4.59 | 0.205 | 2096 | 0.06 | 18.6 | |
| | 80.20 | | | | | | | | | | | | 4.59 | 0.196 | 2094 | 0.06 | 18.8 | |
| | 80.37 | | | | | | | | | | | | 4.59 | 0.196 | 2013 | 0.06 | 18.8 | |

| | | | | | | | | | | | | | | | | | |
|---|---|---|---|---|---|---|---|---|---|---|---|---|---|---|---|---|---|
| 3 | 80.53 | 3.97 | | | | | | | | | | | | | | | |
| | 80.70 | | MSsq* | 0.695 | 3.16 | 1 | | -0.07 | -8.6 | 122 | | 4.59 | 0.199 | 2117 | 0.05 | 18.8 | |
| | 80.87 | | | | | | | | | | | 4.59 | 0.195 | 1977 | 0.05 | 18.9 | |
| 3 | 81.03 | 3.89 | Ssq* | 0.701 | | 0 | | | | | | 4.59 | 0.193 | 995 | 0.05 | 18.9 | |
| | 81.20 | | | | | | | -0.07 | -8.67 | 123 | | 4.59 | 0.200 | 2138 | 0.05 | 18.7 | |
| | 81.37 | | | | | | | | | | | 4.59 | 0.197 | 1999 | 0.06 | 18.8 | |
| 3 | 81.53 | 3.81 | MSsq* | 0.708 | 2.83 | 1 | | | | | | 4.59 | 0.196 | 1933 | 0.06 | 18.9 | |
| | 81.70 | | | | | | | -0.07 | -8.73 | 124 | | 4.59 | 0.206 | 2120 | 0.05 | 18.8 | |
| | 81.87 | | | | | | | | | | | 4.59 | 0.194 | 2084 | 0.05 | 18.9 | |
| 3 | 82.03 | 3.72 | M | 0.715 | 3.72 | 5 | 3.70 | | | | | 4.59 | 0.196 | 1300 | 0.05 | 18.9 | 0.22 |
| | 82.20 | | | | | | | -0.07 | -8.53 | 125 | | 4.59 | 0.200 | 2126 | 0.05 | 18.8 | |
| | 82.37 | | | | | | | | | | | 4.59 | 0.194 | 2108 | 0.05 | 18.9 | |
| 3 | 82.53 | 3.65 | Ss | 0.72 | | 0 | | | | | 1.005 | 4.59 | 0.195 | 1954 | 0.05 | 18.9 | |
| | 82.70 | | | | | | | -0.07 | -8.6 | 126 | | 4.59 | 0.199 | 2103 | 0.05 | 18.8 | |
| | 82.87 | | | | | | | | | | | 4.59 | 0.194 | 2029 | 0.05 | 18.9 | |
| 3 | 83.03 | 3.58 | Ss | 0.725 | | 0 | | | | | | 4.59 | 0.195 | 1983 | 0.05 | 19.1 | |
| | 83.20 | | | | | | | -0.07 | -8.66 | 127 | | 4.58 | 0.203 | 2106 | 0.05 | 18.9 | |
| | 83.37 | | | | | | | | | | | 4.59 | 0.193 | 2045 | 0.06 | 18.9 | |
| 3 | 83.53 | 3.81 | M | 0.708 | 3.81 | 2 | | | | | | 4.59 | 0.195 | 1956 | 0.05 | 19.0 | 0.622 |
| | 83.70 | | | | | | | -0.07 | -8.72 | 128 | | 4.59 | 0.202 | 2092 | 0.06 | 18.8 | |
| | 83.87 | | | | | | | | | | | 4.58 | 0.195 | 2118 | 0.05 | 18.9 | |
| 3 | 84.03 | 3.74 | Ss | 0.713 | | 0 | | | | | | 4.58 | 0.194 | 1883 | 0.05 | 18.9 | |
| | 84.20 | | | | | | | -0.07 | -8.79 | 129 | | 4.58 | 0.197 | 2089 | 0.05 | 18.9 | |
| | 84.37 | | | | | | | | | | | 4.58 | 0.194 | 2083 | 0.06 | 18.9 | |
| 3 | 84.53 | 3.65 | M | 0.72 | 3.65 | 2 | | | | | | 4.58 | 0.195 | 2010 | 0.06 | 19.0 | |
| | | 4.3 | | | | | | -0.07 | -8.85 | 130 | | 4.58 | 0.202 | 2070 | 0.06 | 18.9 | 0.099 |

FIG. 8T

| | | | | | | | | | | | | | | | | | | | |
|---|---|---|---|---|---|---|---|---|---|---|---|---|---|---|---|---|---|---|---|
| 3 | 84.70 | | | | | | | | | | | | | 4.58 | 0.194 | 2119 | 0.06 | 19.0 | |
| | 84.87 | 3.58 | | | | | | | | | | | | 4.58 | 0.194 | 2045 | 0.05 | 18.9 | |
| 3 | 85.03 | | | MSs | 0.725 | 2.32 | 1 | | -0.07 | -8.91 | 131 | | | 4.59 | 0.204 | 2113 | 0.05 | 18.8 | |
| | 85.20 | | | | | | | | | | | | | 4.58 | 0.194 | 2096 | 0.06 | 18.9 | |
| 3 | 85.37 | 3.91 | | M | 0.7 | 3.91 | 1 | | -0.07 | -8.97 | 132 | | | 4.58 | 0.193 | 1875 | 0.06 | 19.0 | |
| | 85.53 | | | | | | | | | | | | | 4.58 | 0.201 | 2060 | 0.06 | 18.9 | |
| 3 | 85.70 | | | M | 0.689 | 4.05 | 4 | 3.65 | -0.06 | -8.2 | 133 | | | 4.58 | 0.194 | 2102 | 0.06 | 18.9 | |
| | 85.87 | 4.05 | | | | | | | | | | | | 4.58 | 0.194 | 2056 | 0.06 | 18.9 | 0.335 |
| 3 | 86.03 | | | M | 0.691 | 4.03 | 4 | 3.98 | -0.06 | -8.26 | 134 | | | 4.58 | 0.202 | 2055 | 0.06 | 18.8 | |
| | 86.20 | | | | | | | | | | | | | 4.58 | 0.194 | 2089 | 0.05 | 18.9 | |
| 3 | 86.37 | 4.03 | | M | 0.72 | 3.65 | 11 | 2.54 | -0.06 | -8.32 | 135 | | | 4.58 | 0.197 | 1910 | 0.05 | 18.8 | 0.185 |
| | 86.53 | | 4.24 | | | | | | | | | | | 4.58 | 0.200 | 2063 | 0.06 | 18.8 | |
| 3 | 86.70 | | | M | 0.709 | 3.79 | 2 | | -0.06 | -8.37 | 136 | | | 4.58 | 0.195 | 2098 | 0.05 | 18.9 | |
| | 86.87 | 3.65 | | | | | | | | | | | | 4.58 | 0.193 | 1997 | 0.06 | 18.8 | |
| 3 | 87.03 | | | M | 0.707 | 3.82 | 3 | 3.47 | -0.06 | -8.43 | 137 | | | 4.58 | 0.201 | 2050 | 0.06 | 18.8 | 0.334 |
| | 87.20 | | | | | | | | | | | | | 4.58 | 0.194 | 2100 | 0.06 | 18.8 | |
| 3 | 87.37 | 3.79 | | | | | | | | | | | | 4.58 | 0.194 | 2040 | 0.06 | 18.8 | |
| | 87.53 | | | M | 0.702 | 3.88 | 4 | 3.81 | -0.06 | -8.49 | 138 | | 0.997 | 4.58 | 0.200 | 2094 | 0.06 | 18.8 | 0.092 |
| | 87.70 | | | | | | | | | | | | | 4.58 | 0.193 | 2094 | 0.06 | 18.8 | |
| 3 | 87.87 | 3.82 | | | | | | | | | | | | 4.58 | 0.194 | 2007 | 0.06 | 18.6 | |
| | 88.03 | | | | | | | | | | | | | 4.58 | 0.201 | 2058 | 0.06 | 18.6 | 0.214 |
| | 88.20 | | | | | | | | | | | | | 4.58 | 0.194 | 2097 | 0.06 | 18.5 | |
| 3 | 88.37 | | | | | | | | | | | | | 4.58 | 0.194 | 2052 | 0.06 | 18.4 | |
| | 88.53 | 3.88 | | | | | | | | | | | | 4.58 | 0.202 | 2104 | 0.06 | 18.5 | 0.172 |
| | 88.70 | | | | | | | | | | | | | 4.58 | 0.195 | 2083 | 0.06 | 18.4 | |

FIG. 8U

| | | | | | | | | | | | | | | | | |
|---|---|---|---|---|---|---|---|---|---|---|---|---|---|---|---|---|
| 3 | 88.87 | | | | | | | | | | | | | | | |
| | 89.03 | 3.82 | | Ms | 0.707 | 3.88 | 7 | 3.79 | -0.06 | -8.55 | 139 | | 4.58 | 0.195 | 1839 | 0.06 | 18.3 | 0.036 |
| | 89.20 | | | | | | | | | | | | 4.58 | 0.204 | 2096 | 0.06 | 18.4 |
| 3 | 89.37 | 3.79 | | MSsq* | 0.709 | 2.8 | 15 | 2.78 | -0.06 | -8.61 | 140 | | 4.58 | 0.194 | 2088 | 0.06 | 18.4 | 0.053 |
| | 89.53 | | | | | | | | | | | | 4.58 | 0.193 | 1949 | 0.06 | 18.2 |
| | 89.70 | | | | | | | | | | | 1.01 | 4.58 | 0.197 | 2108 | 0.06 | 18.6 |
| 3 | 89.87 | 3.76 | | MSsq* | 0.711 | 3.06 | 1 | | -0.06 | -8.66 | 141 | | 4.58 | 0.193 | 2045 | 0.06 | 18.5 |
| | 90.03 | | | | | | | | | | | | 4.58 | 0.194 | 2061 | 0.06 | 18.3 |
| | 90.20 | | | | | | | | | | | | 4.58 | 0.202 | 2140 | 0.06 | 18.5 | 0.182 |
| 3 | 90.37 | 3.73 | | Mq* | 0.714 | 3.83 | 3 | 3.57 | -0.06 | -8.72 | 142 | | 4.58 | 0.194 | 2094 | 0.06 | 18.4 |
| | 90.53 | | | | | | | | | | | 1.006 | 4.58 | 0.193 | 1771 | 0.06 | 18.4 |
| | 90.70 | | | | | | | | | | | | 4.58 | 0.201 | 2027 | 0.06 | 18.6 |
| 3 | 90.87 | 3.7 | | Mq* | 0.716 | 3.7 | 3 | 3.01 | -0.06 | -8.78 | 143 | | 4.58 | 0.193 | 2078 | 0.06 | 18.6 | 0.428 |
| | 91.03 | | | | | | | | | | | | 4.58 | 0.194 | 2061 | 0.06 | 18.6 |
| | 91.20 | | | | | | | | | | | 1.013 | 4.58 | 0.203 | 2021 | 0.05 | 18.8 |
| 3 | 91.37 | 3.68 | | M | 0.718 | 3.68 | 31 | 3.65 | -0.06 | -8.57 | 144 | | 4.58 | 0.194 | 2101 | 0.05 | 18.9 |
| 3 | 91.53 | 3.68 | 15.4 | Ssq* | 0.718 | | 0 | | | -8.62 | 145 | | 4.58 | 0.193 | 1994 | 0.05 | 19.0 | 0.222 |
| | 91.62 | | | | | | | | | | | | 4.58 | 0.196 | 2073 | 0.05 | 19.1 |
| | 91.78 | | | | | | | | | | | | 4.57 | 0.206 | 2098 | 0.05 | 19.1 |
| | 91.95 | | | | | | | | | | | | 4.57 | 0.194 | 2090 | 0.05 | 19.3 |
| 3 | 92.12 | 3.67 | | MS≈ | 0.718 | 2.89 | 9 | 2.48 | -0.06 | -8.58 | 145.17 | | 4.57 | 0.193 | 1838 | 0.05 | 19.4 | 0.139 |
| | 92.28 | | | | | | | | | | | | 4.58 | 0.201 | 2080 | 0.05 | 19.3 |
| | 92.45 | | | | | | | | | | | | 4.57 | 0.194 | 2071 | 0.05 | 19.4 |
| 3 | 92.62 | 3.79 | | M | 0.709 | 3.79 | 2 | | -0.06 | -8.63 | 146.17 | | 4.58 | 0.198 | 2075 | 0.05 | 19.6 | 0.304 |
| | 92.78 | | | | | | | | | | | | 4.58 | 0.193 | 1721 | 0.05 | 19.6 |
| | | | | | | | | | | | | | 4.58 | | 2086 | 0.05 | 19.8 |

| | | | | | | | | | | | | | | | | | |
|---|---|---|---|---|---|---|---|---|---|---|---|---|---|---|---|---|---|
| 4 | 92.95 | | | | | | | | | | | | | | | | |
|  | 93.12 | 3.36 | | | | | | | | | | 4.58 | 0.194 | 2032 | 0.05 | 20.0 | 0.035 |
| 4 | 93.28 | | M | 0.742 | 3.36 | 2 | | | | | | 4.58 | 0.203 | 2096 | 0.05 | 19.8 | |
|  | 93.45 | | | | | | | | | | | 4.58 | 0.193 | 2088 | 0.05 | 19.9 | |
| 4 | 93.62 | 3.66 | 4.M | 0.719 | 3.66 | 11 | 2.23 | | | | | 4.58 | 0.193 | 1819 | 0.05 | 20.3 | 0.476 |
|  | 93.78 | | | | | | | | | | | 4.58 | 0.203 | 2039 | 0.05 | 19.8 | |
| 4 | 93.95 | | | | | | | | | | | 4.57 | 0.192 | 2089 | 0.05 | 20.1 | |
|  | 94.12 | 3.422 | O | 0.737 | 3.82 | 13 | 3.42 | | | | | 4.58 | 0.193 | 2030 | 0.05 | 20.6 | 0.111 |
|  | 94.28 | | | | | | | | | | | 4.57 | 0.202 | 1744 | 0.06 | 20.2 | |
|  | 94.45 | | | | | | | | | | | 4.58 | 0.193 | 2079 | 0.06 | 20.6 | |
| 4 | 94.62 | 2.62 | 4.M | 0.799 | 2.62 | 12 | 1.32 | | 1.011 | | | 4.57 | 0.194 | 2054 | 0.06 | 20.6 | |
|  | 94.78 | | | | | | | | | | | 4.58 | 0.202 | 2098 | 0.06 | 20.4 | 0.376 |
| 4 | 94.95 | | L | 0.799 | 1.65 | 10 | 1.65 | | | | | 4.57 | 0.194 | 2101 | 0.05 | 21.1 | |
|  | 95.12 | 2.62 | | | | | | | | | | 4.57 | 0.192 | 1807 | 0.05 | 21.6 | 0.014 |
| 4 | 95.28 | | O | 0.728 | 3.54 | 9 | 3.54 | | 1.003 | | | 4.58 | 0.202 | 2102 | 0.05 | 20.7 | |
|  | 95.45 | | | | | | | | | | | 4.58 | 0.193 | 2094 | 0.05 | 20.9 | |
| 4 | 95.62 | 3.54 | | | | | | | | | | 4.58 | 0.202 | 1961 | 0.05 | 20.9 | 0.01 |
|  | 95.78 | | O | 0.787 | 3.36 | 9 | 2.78 | | | | | 4.58 | 0.193 | 2038 | 0.05 | 20.8 | |
|  | 95.95 | | | | | | | | | | | 4.58 | 0.194 | 2114 | 0.05 | 21.1 | |
| 4 | 96.12 | 2.776 | | | | | | | | | | 4.57 | 0.193 | 2079 | 0.05 | 21.4 | 0.205 |
|  | 96.28 | | 4.M | 0.781 | 2.85 | 9 | 1.40 | | | | | 4.58 | 0.202 | 2062 | 0.05 | 20.9 | |
|  | 96.45 | | | | | | | | | | | 4.58 | 0.193 | 2093 | 0.05 | 21.2 | |
| 4 | 96.62 | 2.85 | | | | | | | | | | 4.58 | 0.193 | 1986 | 0.05 | 21.3 | |
|  | 96.78 | | | | | | | | | | | 4.58 | 0.202 | 2090 | 0.05 | 21.1 | 0.612 |
|  | 96.95 | | | | | | | | | | | 4.57 | 0.194 | 2106 | 0.05 | 21.7 | |
|  |  | | | | | | | | | | | | | 1974 | 0.05 | 21.6 | |

FIG. 8X

| | | | | | | | | | | | | | | | | | | | | |
|---|---|---|---|---|---|---|---|---|---|---|---|---|---|---|---|---|---|---|---|---|
| 4 | 97.12 | 2.85 | | | | | | | 2 | | | | 4.58 | 0.202 | 2031 | 0.05 | 20.9 | 0.566 |
| | 97.28 | | | L | 0.781 | 1.76 | | | | | | | 4.58 | 0.193 | 2074 | 0.05 | 21.0 | |
| | 97.45 | | | | | | | | | | | | 4.58 | 0.194 | 2044 | 0.05 | 20.6 | |
| 4 | 97.62 | 2.82 | | 4.M | 0.784 | 2.82 | | 9 | 1.00 | | | | 4.58 | 0.202 | 2052 | 0.05 | 20.6 | 0.606 |
| | 97.78 | | | | | | | | | | | | 4.58 | 0.195 | 2132 | 0.05 | 20.9 | |
| | 97.95 | | | | | | | | | | | | 4.58 | 0.193 | 2069 | 0.05 | 21.1 | |
| 4 | 98.12 | 2.6 | | 0 | 0.8 | 2.62 | | 10 | 2.60 | | | | 4.58 | 0.201 | 2142 | 0.05 | 21.1 | 0.589 |
| | 98.28 | | | | | | | | | | | | 4.58 | 0.193 | 2151 | 0.05 | 21.3 | |
| | 98.45 | | | | | | | | | | | | 4.58 | 0.192 | 2088 | 0.05 | 21.7 | |
| 4 | 98.62 | 2.6 | | L | 0.8 | 3.48 | | 2 | | | | | 4.58 | 0.203 | 2029 | 0.05 | 20.7 | 0.269 |
| | 98.78 | | | | | | | | | | | | 4.58 | 0.194 | 2107 | 0.05 | 20.8 | |
| | 98.95 | | | | | | | | 2.49 | | | | 4.58 | 0.192 | 2045 | 0.05 | 20.8 | |
| 4 | 99.12 | 3.2 | | 4.M | 0.754 | 3.2 | | 30 | | 1.008 | | | 4.58 | 0.201 | 2020 | 0.05 | 20.5 | 0.142 |
| | 99.28 | | | | | | | | | | | | 4.58 | 0.195 | 2098 | 0.05 | 20.7 | |
| | 99.45 | | | | | | | | 2.23 | | | | 4.58 | 0.193 | 2053 | 0.05 | 20.8 | |
| 4 | 99.62 | 3.02 | 3.45 | 4.M | 0.768 | 3.02 | | 23 | | | 1.007 | | 4.58 | 0.203 | 2044 | 0.05 | 20.6 | 0.196 |
| | 99.78 | | -0.7 | | | | | | | | | | 4.58 | 0.193 | 2131 | 0.05 | 21.0 | |
| | 99.95 | | | | | | | | 3.19 | | | | 4.59 | 0.194 | 2085 | 0.05 | 20.6 | |
| 4 | 100.12 | 3.188 | | 0 | 0.755 | 3.48 | | 4 | | | | | 4.59 | 0.203 | 2093 | 0.05 | 20.4 | 0.182 |
| | 100.28 | | | | | | | | | | | | 4.59 | 0.194 | 2096 | 0.05 | 20.4 | |
| | 100.45 | | | | | | | | 1.09 | | | | 4.59 | 0.195 | 2066 | 0.05 | 20.4 | |
| 4 | 100.62 | 2.89 | | 4.M | 0.778 | 2.89 | | 16 | | | | 1.002 | 4.59 | 0.205 | 2088 | 0.05 | 20.4 | 0.45 |
| | 100.78 | | | | | | | | | | | | 4.59 | 0.194 | 2127 | 0.05 | 20.3 | |
| | 100.95 | | | | | | | | | | | | 4.59 | 0.194 | 2103 | 0.05 | 20.5 | |
| 4 | 101.12 | 2.89 | | L | 0.778 | 2.42 | | 2 | | | | | 4.59 | 0.204 | 2100 | 0.05 | 20.4 | 0.163 |

FIG. 8Y

| | | | | | | | | | | | | | | | | | |
|---|---|---|---|---|---|---|---|---|---|---|---|---|---|---|---|---|---|
| 101.28 | 4 | | | | | | | | | | | | | | | | |
| 101.45 | | 2.727 | | | | | | | | | | | | | | | |
| 101.62 | 4 | | 0 | 0.791 | 2.81 | 9 | 2.73 | | | | 4.59 | 0.194 | 2147 | 0.05 | 20.6 | | |
| 101.78 | | | | | | | | | | | 4.59 | 0.193 | 2108 | 0.05 | 20.5 | 0.697 | |
| 101.95 | 4 | 2.81 | 4.M | 0.784 | 2.81 | 5 | 2.54 | | | | 4.59 | 0.199 | 1976 | 0.05 | 20.4 | | |
| 102.12 | 4 | | | | | | | | | | 4.58 | 0.194 | 2150 | 0.05 | 20.9 | 0.391 | |
| 102.28 | | | | | | | | | | | 4.59 | 0.194 | 2062 | 0.05 | 20.6 | | |
| 102.45 | 4 | 3.08 | 4.M | 0.764 | 3.08 | 4 | 2.20 | | | | 4.59 | 0.204 | 2102 | 0.06 | 20.3 | | |
| 102.62 | 4 | | | | | | | | | | 4.59 | 0.194 | 2101 | 0.05 | 20.3 | 0.541 | |
| 102.78 | | | | | | | | | | | 4.59 | 0.193 | 2031 | 0.05 | 20.4 | | |
| 102.95 | 4 | 2.707 | 0 | 0.792 | 2.87 | 8 | 2.71 | | | | 4.59 | 0.206 | 2143 | 0.05 | 20.2 | | |
| 103.12 | | | | | | | | | | | 4.59 | 0.194 | 2131 | 0.05 | 20.4 | 0.09 | |
| 103.28 | | | | | | | | | | | 4.59 | 0.193 | 2027 | 0.06 | 20.3 | | |
| 103.45 | 4 | 2.707 | L | 0.792 | 2.73 | 2 | | | | | 4.59 | 0.205 | 2148 | 0.05 | 20.2 | | |
| 103.62 | | | | | | | | | | | 4.59 | 0.194 | 2135 | 0.06 | 20.4 | 0.092 | |
| 103.78 | | | | | | | | | | | 4.59 | 0.193 | 2110 | 0.06 | 20.4 | | |
| 103.95 | 4 | 2.62 | 4.M | 0.799 | 2.62 | 8 | 2.40 | | | | 4.59 | 0.204 | 2140 | 0.06 | 20.1 | | |
| 104.12 | | | | | | | | | | | 4.59 | 0.194 | 2133 | 0.06 | 20.3 | 0.108 | |
| 104.28 | | | | | | | | | | | 4.59 | 0.193 | 2150 | 0.06 | 20.6 | | |
| 104.45 | 4 | 2.577 | 0 | 0.802 | 3.07 | 5 | 2.58 | 2.99 | | | 4.59 | 0.201 | 2079 | 0.06 | 20.4 | | |
| 104.62 | | | | | | | | | | | 4.59 | 0.194 | 2131 | 0.06 | 20.4 | 0.642 | |
| 104.78 | | | | | | | | | | | 4.59 | 0.195 | 2036 | 0.06 | 20.4 | | |
| 104.95 | 4 | 2.64 | 4.M | 0.797 | 2.64 | 5 | 2.01 | | | | 4.59 | 0.200 | 2018 | 0.06 | 20.5 | | |
| 105.12 | | | | | | | | | | | 4.59 | 0.196 | 2142 | 0.06 | 21.0 | 0.743 | |
| 105.28 | | | | | | | | | | | 4.59 | 0.193 | 2112 | 0.05 | 20.4 | | |
| | | | | | | | | | | | 4.59 | 0.203 | 2129 | 0.05 | 20.4 | | |
| | | | | | | | | | | | 4.59 | 0.194 | 2124 | 0.06 | 20.7 | | |

FIG. 8Z

| | | | | | | | | | | | | | | | | | |
|---|---|---|---|---|---|---|---|---|---|---|---|---|---|---|---|---|---|
| 4 | 105.45 | | | | | | | | | | 4.59 | 0.194 | 2137 | 0.05 | 20.9 | |
| | 105.62 | 2.64 | | | L | 0.797 | 2.44 | 4 | 2.05 | | | 4.59 | 0.201 | 2087 | 0.05 | 20.6 | 0.447 |
| | 105.78 | | | | | | | | | | | 4.59 | 0.194 | 2152 | 0.05 | 20.7 | |
| | 105.95 | | | | | | | | | | | 4.59 | 0.193 | 2128 | 0.05 | 20.8 | |
| 4 | 106.12 | 3.26 | 3.74 | 4.M | 0.75 | 3.26 | 7 | 2.30 | | | | 4.59 | 0.201 | 2098 | 0.05 | 20.6 | 0.843 |
| | 106.28 | | | | | | | | | | | 4.59 | 0.195 | 2133 | 0.05 | 20.6 | |
| | 106.45 | | | | | | | | | | | 4.59 | 0.194 | 2074 | 0.05 | 20.6 | |
| 4 | 106.62 | 3.13 | 3.28 | 4.M | 0.76 | 3.13 | 14 | 2.20 | | | | 4.59 | 0.205 | 2087 | 0.05 | 20.4 | 0.381 |
| | 106.78 | | | | | | | | | | | 4.59 | 0.194 | 2122 | 0.05 | 20.6 | |
| | 106.95 | | | | | | | | | | | 4.59 | 0.194 | 2144 | 0.05 | 20.6 | |
| 4 | 107.12 | 2.762 | | 0 | 0.788 | 3.03 | 16 | 2.76 | | 1.007 | | 4.59 | 0.204 | 2135 | 0.06 | 20.4 | 0.396 |
| | 107.28 | | | | | | | | | | | 4.59 | 0.195 | 2132 | 0.06 | 20.5 | |
| | 107.45 | | | | | | | | | | | 4.59 | 0.193 | 2113 | 0.06 | 20.6 | |
| 4 | 107.62 | 2.74 | | 4.M | 0.79 | 2.74 | 8 | 2.15 | | 1.009 | | 4.59 | 0.203 | 2145 | 0.06 | 20.4 | 0.321 |
| | 107.78 | | | | | | | | | | | 4.59 | 0.194 | 2119 | 0.06 | 20.4 | |
| | 107.95 | | | | | | | | | | | 4.59 | 0.193 | 2145 | 0.06 | 20.4 | |
| 4 | 108.12 | 2.96 | | 4.M | 0.773 | 2.96 | 21 | 2.55 | | 1.008 | | 4.59 | 0.205 | 2142 | 0.06 | 20.3 | 0.342 |
| | 108.28 | | | | | | | | | | | 4.59 | 0.196 | 2147 | 0.06 | 20.4 | |
| | 108.45 | | | | | | | | | | | 4.59 | 0.195 | 2084 | 0.06 | 20.3 | |
| 4 | 108.62 | 2.729 | | 0 | 0.791 | 2.78 | 4 | 2.73 | | | | 4.59 | 0.203 | 2134 | 0.06 | 20.3 | 0.476 |
| | 108.78 | | | | | | | | | | | 4.59 | 0.194 | 2137 | 0.06 | 20.4 | |
| | 108.95 | | | | | | | | | | | 4.59 | 0.194 | 2141 | 0.06 | 20.4 | |
| 4 | 109.12 | 2.662 | | 0 | 0.796 | 2.95 | 6 | 2.66 | | | | 4.59 | 0.202 | 2138 | 0.06 | 20.3 | 0.907 |
| | 109.28 | | | | | | | | | | | 4.59 | 0.194 | 2148 | 0.06 | 20.4 | |
| | 109.45 | | | | | | | | | | | 4.60 | 0.194 | 2133 | 0.06 | 20.3 | |

FIG. 8AA

| C1 | C2 | C3 | C4 | C5 | C6 | C7 | C8 | C9 | C10 | C11 | C12 | C13 | C14 | C15 | C16 |
|---|---|---|---|---|---|---|---|---|---|---|---|---|---|---|---|
| 4 | 109.62 | 2.89 | 3.2 | 0 | 0.778 | 3 | 5 | 2.89 | | 4.60 | 0.206 | 2162 | 0.06 | 20.3 | 0.211 |
| 4 | 109.78 | | | | | | | | | 4.59 | 0.194 | 2137 | 0.06 | 20.4 | |
| 4 | 109.95 | | | | | | | | | 4.59 | 0.195 | 2121 | 0.06 | 20.3 | |
| 4 | 110.12 | 2.89 | | L2 | 0.778 | 2.55 | 3 | 1.86 | 0.998 | 4.60 | 0.205 | 2172 | 0.06 | 20.3 | 0.422 |
| 4 | 110.28 | | | | | | | | | 4.60 | 0.194 | 2136 | 0.06 | 20.4 | |
| 4 | 110.45 | | | | | | | | | 4.60 | 0.195 | 2127 | 0.06 | 20.3 | |
| 4 | 110.62 | 2.62 | | 0 | 0.799 | 2.82 | 4 | 2.62 | | 4.60 | 0.203 | 2153 | 0.05 | 20.3 | 0.253 |
| 4 | 110.78 | | | | | | | | | 4.59 | 0.193 | 2151 | 0.05 | 20.3 | |
| 4 | 110.95 | | | | | | | | | 4.60 | 0.194 | 2127 | 0.05 | 20.3 | |
| 4 | 111.12 | 2.62 | 3.48 | L | 0.799 | 1.89 | 6 | 1.77 | | 4.60 | 0.204 | 2161 | 0.05 | 20.3 | 0.549 |
| 4 | 111.28 | | | | | | | | | 4.60 | 0.196 | 2146 | 0.05 | 20.3 | |
| 4 | 111.45 | | | | | | | | | 4.60 | 0.196 | 2143 | 0.05 | 20.2 | |
| 4 | 111.62 | 2.828 | | 0 | 0.783 | 3.16 | 14 | 2.83 | 1.008 | 4.60 | 0.202 | 2158 | 0.05 | 20.2 | 0.844 |
| 4 | 111.78 | | | | | | | | | 4.59 | 0.196 | 2138 | 0.05 | 20.3 | |
| 4 | 111.95 | | | | | | | | | 4.60 | 0.197 | 2139 | 0.05 | 20.3 | |
| 4 | 112.12 | 2.622 | 3.16 | 0 | 0.799 | 2.85 | 10 | 2.62 | 1.003 | 4.60 | 0.202 | 2168 | 0.05 | 20.3 | 0.878 |
| 4 | 112.28 | | | | | | | | | 4.60 | 0.196 | 2149 | 0.06 | 20.3 | |
| 4 | 112.45 | | | | | | | | | 4.60 | 0.196 | 2142 | 0.05 | 20.3 | |
| 4 | 112.62 | 2.622 | 3.17 | L | 0.799 | 1.84 | 4 | 1.72 | | 4.60 | 0.203 | 2171 | 0.05 | 20.3 | 0.311 |
| 4 | 112.78 | | | | | | | | | 4.60 | 0.197 | 2172 | 0.05 | 20.3 | |
| 4 | 112.95 | | | | | | | | | 4.60 | 0.197 | 2124 | 0.05 | 20.2 | |
| 4 | 113.12 | 2.668 | | 0 | 0.795 | 3 | 9 | 2.67 | 1.007 | 4.60 | 0.203 | 2156 | 0.05 | 20.2 | 0.833 |
| 4 | 113.28 | | | | | | | | | 4.60 | 0.197 | 2163 | 0.05 | 20.1 | |
| 4 | 113.45 | | | | | | | | | 4.60 | 0.198 | 2135 | 0.05 | 20.1 | |
| 4 | 113.62 | 3.03 | 3.06 | 4.M | 0.767 | 3.03 | 11 | 1.38 | 1.002 | 4.60 | 0.203 | 2152 | 0.05 | 20.1 | 0.691 |

FIG. 8BB

| | | | | | | | | | | | | | | | | | |
|---|---|---|---|---|---|---|---|---|---|---|---|---|---|---|---|---|---|
| 4 | 113.78 | | | | | | | | | | | | | | | | |
|   | 113.95 | | | | | | | | | | | 4.60 | 0.197 | 2145 | 0.05 | 20.1 | |
| 4 | 114.12 | 2.776 | 3.24 | 0 | 0.787 | 3.24 | 19 | 2.78 | | | | 4.60 | 0.198 | 2153 | 0.05 | 20.1 | |
|   | 114.28 | | | | | | | | | | 1.009 | 4.60 | 0.202 | 2157 | 0.05 | 20.1 | 0.761 |
|   | 114.45 | | | | | | | | | | | 4.60 | 0.196 | 2134 | 0.05 | 20.1 | |
| 4 | 114.62 | 3.04 | 4.02 | 4.M | 0.767 | 3.04 | 14 | 2.46 | | | | 4.60 | 0.200 | 2165 | 0.05 | 20.1 | |
|   | 114.78 | | | | | | | | | | 1.006 | 4.60 | 0.202 | 2145 | 0.05 | 20.1 | 0.429 |
|   | 114.95 | | | | | | | | | | | 4.60 | 0.199 | 2147 | 0.05 | 20.1 | |
| 4 | 115.12 | 2.707 | 3.54 | 0 | 0.792 | 3 | 17 | 2.71 | | | | 4.60 | 0.198 | 2143 | 0.05 | 20.2 | |
|   | 115.28 | | | | | | | | | | 1.009 | 4.60 | 0.202 | 2187 | 0.05 | 20.3 | 0.632 |
|   | 115.45 | | | | | | | | | | | 4.60 | 0.197 | 2128 | 0.05 | 20.5 | |
| 4 | 115.62 | 2.81 | 3.26 | 4.M | 0.784 | 2.81 | 7 | 2.01 | | | | 4.60 | 0.198 | 2157 | 0.05 | 20.4 | |
| 4 | 115.67 | 2.66 | | 4.M | 0.796 | 2.66 | 4 | 2.38 | | | | 4.60 | 0.202 | 2161 | 0.05 | 20.4 | 0.56 |
|   | 115.83 | | | | | | | | | | | 4.60 | 0.204 | 2191 | 0.05 | 20.6 | 0.316 |
| 4 | 116.00 | | | L | | | | | | | | 4.60 | 0.195 | 2145 | 0.06 | 20.7 | |
| 4 | 116.17 | 2.66 | | | 0.796 | 2.41 | 3 | 1.93 | | | | 4.60 | 0.195 | 2157 | 0.05 | 20.8 | |
|   | 116.33 | | | | | | | | | | | 4.60 | 0.202 | 2141 | 0.05 | 20.7 | 0.31 |
|   | 116.50 | | | | | | | | | | | 4.60 | 0.196 | 2138 | 0.05 | 20.8 | |
| 4 | 116.67 | 2.88 | 3.3 | 4.M | 0.779 | 2.88 | 16 | 2.55 | | | | 4.60 | 0.198 | 2142 | 0.05 | 20.7 | |
|   | 116.83 | | | | | | | | | | 1.008 | 4.60 | 0.202 | 2168 | 0.05 | 20.8 | 0.354 |
|   | 117.00 | | | | | | | | | | | 4.60 | 0.209 | 2165 | 0.05 | 20.8 | |
| 4 | 117.17 | 2.851 | 3.29 | 0 | 0.781 | 3.12 | 20 | 2.85 | | | | 4.60 | 0.229 | 2178 | 0.05 | 20.8 | |
|   | 117.33 | | | | | | | | | | 1.01 | 4.60 | 0.251 | 2182 | 0.05 | 20.8 | 0.767 |
|   | 117.50 | | | | | | | | | | | 4.60 | 0.266 | 2166 | 0.06 | 20.6 | |
| 4 | 117.67 | 3.003 | 3.85 | 0 | 0.77 | 3.14 | 31 | 3.00 | | | 1.01 | 4.60 | 0.281 | 2177 | 0.06 | 20.7 | |
|   |        |       |      |   |      |      |    |      | | | 1.01 | 4.61 | 0.295 | 2179 | 0.06 | 20.7 | 0.504 |

FIG. 8CC

| 4 | 117.83 | | | | | | | | | | | | | | | | | | |
|---|---|---|---|---|---|---|---|---|---|---|---|---|---|---|---|---|---|---|---|
| | 118.00 | 2.967 | 2.65 | 0 | 0.772 | 3.05 | 31 | 2.97 | | | 4.61 | 0.308 | 2183 | 0.06 | 20.7 | 0.619 |
| | 118.17 | | | | | | | | | | 4.61 | 0.318 | 2191 | 0.06 | 20.7 | |
| | 118.33 | | | | | | | | | | 4.61 | 0.331 | 2187 | 0.06 | 20.9 | |
| 4 | 118.50 | 2.945 | 3.41 | 0 | 0.774 | 2.99 | 31 | 2.95 | | | 4.61 | 0.341 | 2204 | 0.06 | 20.7 | 0.128 |
| | 118.67 | | | | | | | | | | 4.61 | 0.351 | 2237 | 0.06 | 20.7 | |
| | 118.83 | | | | | | | | | 1.009 | 4.61 | 0.360 | 2239 | 0.06 | 20.7 | |
| 4 | 119.00 | 2.902 | 3.63 | 0 | 0.777 | 2.99 | 31 | 2.90 | | | 4.61 | 0.370 | 2274 | 0.05 | 20.6 | 0.384 |
| | 119.17 | | | | | | | | | | 4.61 | 0.376 | 2219 | 0.06 | 20.7 | |
| | 119.33 | | | | | | | | | | 4.61 | 0.385 | 2262 | 0.06 | 20.7 | |
| 4 | 119.50 | 2.886 | 2.7 | 0 | 0.779 | 2.98 | 30 | 2.89 | | 1.009 | 4.61 | 0.393 | 2255 | 0.06 | 20.7 | |
| | 119.67 | | | | | | | | | | 4.61 | 0.400 | 2254 | 0.06 | 20.7 | |
| | 119.83 | | | | | | | | | | 4.61 | 0.406 | 2243 | 0.06 | 20.8 | 0.322 |
| 4 | 120.00 | 2.873 | 2.68 | 0 | 0.78 | 2.95 | 31 | 2.87 | | | 4.61 | 0.413 | 2251 | 0.05 | 20.8 | |
| | 120.17 | | | | | | | | | 1.009 | 4.61 | 0.421 | 2269 | 0.05 | 20.8 | 0.38 |
| | 120.33 | | | | | | | | | | 4.61 | 0.428 | 2268 | 0.05 | 20.8 | |
| 4 | 120.50 | 2.844 | 2.89 | 0 | 0.782 | 2.93 | 29 | 2.84 | | | 4.61 | 0.432 | 2274 | 0.05 | 20.7 | |
| | 120.67 | | | | | | | | | | 4.61 | 0.440 | 2238 | 0.06 | 20.9 | 0.421 |
| | 120.83 | | | | | | | | | 1.009 | 4.61 | 0.445 | 2252 | 0.05 | 20.8 | |
| 4 | 121.00 | 2.836 | 2.72 | 0 | 0.782 | 2.92 | 30 | 2.84 | | | 4.61 | 0.450 | 2261 | 0.06 | 20.7 | |
| | 121.17 | | | | | | | | | | 4.61 | 0.456 | 2284 | 0.05 | 20.7 | 0.412 |
| | 121.33 | | | | | | | | | | 4.61 | 0.462 | 2287 | 0.05 | 20.6 | |
| 4 | 121.50 | 2.811 | 2.68 | 0 | 0.784 | 2.9 | 30 | 2.81 | | 1.009 | 4.61 | 0.467 | 2290 | 0.05 | 20.7 | |
| | 121.67 | | | | | | | | | | 4.61 | 0.473 | 2290 | 0.05 | 20.7 | 0.579 |
| | 121.83 | | | | | | | | | | 4.62 | 0.485 | 2289 | 0.06 | 20.7 | |

| | | | | | | | | | | | | | | | | | |
|---|---|---|---|---|---|---|---|---|---|---|---|---|---|---|---|---|---|
| 4 | 122.00 | | | | | | | | | | | | 0.490 | 2292 | 0.05 | 20.6 | |
| | 122.17 | 2.83 | 2.6 | 0 | 0.783 | 2.89 | 30 | 2.83 | | | 1.009 | 4.61 | 0.494 | 2292 | 0.05 | 20.6 | 0.363 |
| | 122.33 | | | | | | | | | | | 4.61 | 0.499 | 2291 | 0.05 | 20.6 | |
| | 122.50 | | | | | | | | | | | 4.61 | 0.504 | 2265 | 0.05 | 20.7 | |
| 4 | 122.67 | 2.82 | 2.98 | 0 | 0.784 | 2.89 | 30 | 2.82 | | | 1.009 | 4.61 | 0.509 | 2288 | 0.05 | 20.7 | 0.312 |
| | 122.83 | | | | | | | | | | | 4.61 | 0.514 | 2293 | 0.05 | 20.6 | |
| | 123.00 | | | | | | | | | | | 4.62 | 0.518 | 2301 | 0.05 | 20.6 | |
| 4 | 123.17 | 2.841 | 2.79 | 0 | 0.782 | 2.92 | 31 | 2.84 | | | 1.009 | 4.61 | 0.523 | 2263 | 0.06 | 20.7 | 0.207 |
| | 123.33 | | | | | | | | | | | 4.61 | 0.526 | 2299 | 0.06 | 20.6 | |
| | 123.50 | | | | | | | | | | | 4.61 | 0.531 | 2301 | 0.06 | 20.5 | |
| 4 | 123.67 | 2.854 | 2.69 | 0 | 0.781 | 2.9 | 31 | 2.85 | | | 1.009 | 4.61 | 0.536 | 2301 | 0.06 | 20.5 | 0.074 |
| | 123.83 | | | | | | | | | | | 4.61 | 0.540 | 2306 | 0.05 | 20.5 | |
| | 124.00 | | | | | | | | | | | 4.61 | 0.544 | 2303 | 0.05 | 20.5 | |
| 4 | 124.17 | 2.846 | 2.97 | 0 | 0.782 | 2.93 | 31 | 2.85 | | | 1.009 | 4.61 | 0.549 | 2301 | 0.06 | 20.5 | 0.1 |
| | 124.33 | | | | | | | | | | | 4.61 | 0.552 | 2301 | 0.06 | 20.5 | |
| | 124.50 | | | | | | | | | | | 4.61 | 0.558 | 2303 | 0.06 | 20.6 | |
| 4 | 124.67 | 2.829 | | 0 | 0.783 | 2.88 | 31 | 2.83 | | | 1.009 | 4.61 | 0.562 | 2300 | 0.06 | 20.6 | 0.144 |
| | 124.83 | | | | | | | | | | | 4.61 | 0.565 | 2308 | 0.05 | 20.5 | |
| | 125.00 | | | | | | | | | | | 4.61 | 0.568 | 2311 | 0.05 | 20.5 | |
| 4 | 125.17 | 2.811 | | 0 | 0.784 | 2.87 | 31 | 2.81 | | | 1.009 | 4.61 | 0.573 | 2310 | 0.05 | 20.5 | 0.146 |
| | 125.33 | | | | | | | | | | | 4.61 | 0.577 | 2306 | 0.05 | 20.5 | |
| | 125.50 | | | | | | | | | | | 4.61 | 0.581 | 2320 | 0.05 | 20.4 | |
| 4 | 125.67 | 2.816 | 2.57 | 0 | 0.784 | 2.85 | 31 | 2.82 | | | 1.009 | 4.61 | 0.584 | 2305 | 0.05 | 20.6 | 0.111 |
| | 125.83 | | | | | | | | | | | 4.61 | 0.588 | 2310 | 0.05 | 20.5 | |
| | 126.00 | | | | | | | | | | | 4.61 | 0.591 | 2313 | 0.05 | 20.5 | |

FIG. 8DD

| 4 | 126.17 | 2.835 |      | 0 | 0.782 | 2.87 | 30 | 2.84 |  | 1.009 | 4.61 | 0.595 | 2314 | 0.05 | 20.5 | 0.086 |
| 4 | 126.33 |       |      |   |       |      |    |      |  |       | 4.61 | 0.599 | 2313 | 0.05 | 20.4 |       |
| 4 | 126.50 |       |      |   |       |      |    |      |  |       | 4.61 | 0.603 | 2322 | 0.05 | 20.5 | 0.078 |
| 4 | 126.67 | 2.818 |      | 0 | 0.784 | 2.84 | 31 | 2.82 |  | 1.009 | 4.61 | 0.605 | 2321 | 0.05 | 20.5 |       |
| 4 | 126.83 |       |      |   |       |      |    |      |  |       | 4.61 | 0.608 | 2322 | 0.05 | 20.4 |       |
| 4 | 127.00 |       |      |   |       |      |    |      |  |       | 4.61 | 0.612 | 2319 | 0.05 | 20.4 | 0.077 |
| 4 | 127.17 | 2.814 |      | 0 | 0.784 | 2.85 | 31 | 2.81 |  | 1.009 | 4.61 | 0.616 | 2319 | 0.05 | 20.4 |       |
| 4 | 127.33 |       |      |   |       |      |    |      |  |       | 4.61 | 0.619 | 2323 | 0.05 | 20.4 |       |
| 4 | 127.50 |       |      |   |       |      |    |      |  |       | 4.61 | 0.622 | 2324 | 0.05 | 20.4 | 0.068 |
| 4 | 127.67 | 2.819 |      | 0 | 0.784 | 2.85 | 31 | 2.82 |  | 1.009 | 4.61 | 0.625 | 2303 | 0.05 | 20.4 |       |
| 4 | 127.83 |       |      |   |       |      |    |      |  |       | 4.61 | 0.629 | 2323 | 0.06 | 20.4 |       |
| 4 | 128.00 |       |      |   |       |      |    |      |  |       | 4.61 | 0.632 | 2327 | 0.06 | 20.3 | 0.062 |
| 4 | 128.17 | 2.824 | 2.57 | 0 | 0.783 | 2.89 | 31 | 2.82 |  | 1.009 | 4.61 | 0.635 | 2323 | 0.06 | 20.4 |       |
| 4 | 128.33 |       |      |   |       |      |    |      |  |       | 4.61 | 0.639 | 2329 | 0.06 | 20.4 |       |
| 4 | 128.50 |       |      |   |       |      |    |      |  |       | 4.61 | 0.643 | 2324 | 0.06 | 20.4 | 0.065 |
| 4 | 128.67 | 2.811 |      | 0 | 0.784 | 2.84 | 31 | 2.81 |  | 1.009 | 4.61 | 0.646 | 2329 | 0.06 | 20.4 |       |
| 4 | 128.83 |       |      |   |       |      |    |      |  |       | 4.61 | 0.650 | 2332 | 0.06 | 20.3 |       |
| 4 | 129.00 |       |      |   |       |      |    |      |  |       | 4.61 | 0.654 | 2334 | 0.06 | 20.3 | 0.06  |
| 4 | 129.17 | 2.806 | 2.77 | 0 | 0.785 | 2.82 | 31 | 2.81 |  | 1.009 | 4.61 | 0.657 | 2329 | 0.06 | 20.4 |       |
| 4 | 129.33 |       |      |   |       |      |    |      |  |       | 4.61 | 0.661 | 2327 | 0.06 | 20.4 |       |
| 4 | 129.50 |       |      |   |       |      |    |      |  |       | 4.61 | 0.665 | 2333 | 0.06 | 20.3 | 0.058 |
| 4 | 129.67 | 2.808 | 2.65 | 0 | 0.784 | 2.83 | 31 | 2.81 |  | 1.009 | 4.61 | 0.669 | 2332 | 0.06 | 20.3 |       |
| 4 | 129.83 |       |      |   |       |      |    |      |  |       | 4.61 | 0.672 | 2333 | 0.06 | 20.3 |       |
| 4 | 130.00 |       |      |   |       |      |    |      |  |       | 4.61 | 0.676 | 2335 | 0.06 | 20.3 |       |
| 4 | 130.17 | 2.801 | 2.62 | 0 | 0.785 | 2.83 | 31 | 2.80 |  | 1.009 | 4.61 | 0.679 | 2334 | 0.06 | 20.3 | 0.06  |

FIG. 8EE

| | | | | | | | | | | | | | | | | | | |
|---|---|---|---|---|---|---|---|---|---|---|---|---|---|---|---|---|---|---|
| 4 | 130.33 | | | | | | | | | | | | | | | | | |
| | 130.50 | | | | | | | | | | | | | | | | | |
| | 130.67 | 2.795 | 2.64 | 0 | 0.785 | 31 | 2.83 | 2.80 | | | 1.009 | 4.61 | 0.683 | 2331 | 0.06 | 20.4 | |
| | 130.83 | | | | | | | | | | | | 0.687 | 2334 | 0.06 | 20.3 | |
| 4 | 131.00 | | | | | | | | | | | 4.61 | 0.691 | 2334 | 0.06 | 20.3 | 0.062 |
| | 131.17 | 2.805 | 2.6 | 0 | 0.785 | 31 | 2.82 | 2.81 | | | | 4.61 | 0.695 | 2335 | 0.06 | 20.3 | |
| | 131.33 | | | | | | | | | | | 4.61 | 0.699 | 2336 | 0.06 | 20.3 | |
| | 131.50 | | | | | | | | | | 1.009 | 4.61 | 0.702 | 2340 | 0.06 | 20.3 | 0.064 |
| 4 | 131.67 | 2.808 | 2.59 | 0 | 0.784 | 31 | 2.82 | 2.81 | | | | 4.61 | 0.706 | 2337 | 0.05 | 20.3 | |
| | 131.83 | | | | | | | | | | | 4.61 | 0.709 | 2343 | 0.05 | 20.3 | |
| | 132.00 | | | | | | | | | | | 4.61 | 0.713 | 2338 | 0.05 | 20.3 | 0.059 |
| 4 | 132.17 | 2.799 | | 0 | 0.785 | 30 | 2.82 | 2.80 | | | 1.009 | 4.61 | 0.716 | 2359 | 0.05 | 20.3 | |
| | 132.33 | | | | | | | | | | | 4.61 | 0.719 | 2357 | 0.05 | 20.3 | |
| | 132.50 | | | | | | | | | | | 4.61 | 0.722 | 2360 | 0.05 | 20.3 | 0.078 |
| 4 | 132.67 | 2.805 | | 0 | 0.785 | 31 | 2.84 | 2.81 | | | | 4.61 | 0.725 | 2357 | 0.05 | 20.3 | |
| | 132.83 | | | | | | | | | | | 4.60 | 0.727 | 2354 | 0.05 | 20.3 | |
| | 133.00 | | | | | | | | | | 1.009 | 4.60 | 0.731 | 2377 | 0.05 | 20.3 | 0.063 |
| 4 | 133.17 | 2.814 | 2.7 | 0 | 0.784 | 31 | 2.84 | 2.81 | | | | 4.60 | 0.734 | 2376 | 0.05 | 20.3 | |
| | 133.33 | | | | | | | | | | | 4.60 | 0.737 | 2377 | 0.05 | 20.3 | |
| | 133.50 | | | | | | | | | | | 4.60 | 0.739 | 2378 | 0.05 | 20.3 | 0.061 |
| 4 | 133.67 | 2.812 | 2.69 | 0 | 0.784 | 31 | 2.83 | 2.81 | | | 1.009 | 4.60 | 0.742 | 2376 | 0.05 | 20.3 | |
| | 133.83 | | | | | | | | | | | 4.60 | 0.746 | 2377 | 0.05 | 20.3 | |
| | 134.00 | | | | | | | | | | | 4.60 | 0.748 | 2377 | 0.05 | 20.3 | 0.063 |
| 4 | 134.17 | 2.81 | 2.71 | 0 | 0.784 | 31 | 2.83 | 2.81 | | | | 4.60 | 0.750 | 2377 | 0.05 | 20.2 | |
| | 134.33 | | | | | | | | | | 1.009 | 4.60 | 0.753 | 2381 | 0.06 | 20.2 | |
| | | | | | | | | | | | | 4.60 | 0.757 | 2381 | 0.05 | 20.2 | 0.064 |
| | | | | | | | | | | | | 4.60 | 0.760 | 2388 | 0.05 | 20.2 | |

| | | | | | | | | | | | | | | | | |
|---|---|---|---|---|---|---|---|---|---|---|---|---|---|---|---|---|
| 4 | 134.50 | | | | | | | | | | | | | | | |
| 4 | 134.67 | 2.795 | 2.71 | 0 | 0.785 | 2.81 | 31 | 2.80 | | | | | | | | |
| 4 | 134.83 | | | | | | | | | | | | | | | |
| 4 | 135.00 | 2.794 | 2.76 | 0 | 0.786 | 2.81 | 31 | 2.79 | | | | | | | | |
| 4 | 135.17 | | | | | | | | | | | | | | | |
| 4 | 135.33 | | | | | | | | | | | | | | | |
| 4 | 135.50 | | | | | | | | | | | | | | | |
| 4 | 135.67 | 2.794 | 2.66 | 0 | 0.786 | 2.81 | 31 | 2.79 | | | | | | | | |
| 4 | 135.83 | | | | | | | | | | | | | | | |
| 4 | 136.00 | | | | | | | | | | | | | | | |
| 4 | 136.17 | 2.776 | 2.69 | 0 | 0.787 | 2.8 | 31 | 2.78 | | | | | | | | |
| 4 | 136.33 | | | | | | | | | | | | | | | |
| 4 | 136.50 | | | | | | | | | | | | | | | |
| 4 | 136.67 | 2.762 | 2.7 | 0 | 0.788 | 2.77 | 31 | 2.76 | | | | | | | | |
| 4 | 136.83 | | | | | | | | | | | | | | | |
| 4 | 137.00 | | | | | | | | | | | | | | | |
| 4 | 137.17 | 2.76 | 2.69 | 0 | 0.788 | 2.77 | 31 | 2.76 | | | | | | | | |
| 4 | 137.33 | | | | | | | | | | | | | | | |
| 4 | 137.50 | | | | | | | | | | | | | | | |
| 4 | 137.67 | 2.756 | | 0 | 0.788 | 2.77 | 31 | 2.76 | | | | | | | | |
| 4 | 137.83 | | | | | | | | | | | | | | | |
| 4 | 138.00 | | | | | | | | | | | | | | | |
| 4 | 138.17 | 2.74 | 2.68 | 0 | 0.79 | 2.75 | 31 | 2.74 | | | | | | | | |
| 4 | 138.33 | | | | | | | | | | | | | | | |
| 4 | 138.50 | | | | | | | | | | | | | | | |

| | | | | | | |
|---|---|---|---|---|---|---|
| | | | | | | |
| | 1.009 | 4.60 | 0.762 | 2389 | 0.05 | 20.3 | 0.052 |
| | | 4.60 | 0.765 | 2392 | 0.05 | 20.3 | |
| | | 4.60 | 0.768 | 2380 | 0.05 | 20.2 | 0.064 |
| | 1.009 | 4.60 | 0.770 | 2380 | 0.05 | 20.3 | |
| | | 4.60 | 0.773 | 2384 | 0.05 | 20.2 | 0.055 |
| | | 4.60 | 0.776 | 2371 | 0.05 | 20.3 | |
| | 1.009 | 4.60 | 0.778 | 2372 | 0.05 | 20.2 | |
| | | 4.60 | 0.781 | 2391 | 0.05 | 20.2 | 0.041 |
| | | 4.60 | 0.785 | 2394 | 0.05 | 20.2 | |
| | | 4.60 | 0.789 | 2398 | 0.05 | 20.2 | |
| | 1.009 | 4.60 | 0.792 | 2396 | 0.05 | 20.3 | 0.041 |
| | | 4.60 | 0.796 | 2394 | 0.05 | 20.3 | |
| | | 4.60 | 0.799 | 2398 | 0.05 | 20.3 | |
| | 1.009 | 4.60 | 0.803 | 2396 | 0.05 | 20.4 | 0.045 |
| | | 4.60 | 0.806 | 2400 | 0.06 | 20.4 | |
| | | 4.60 | 0.809 | 2402 | 0.06 | 20.4 | |
| | 1.009 | 4.60 | 0.812 | 2406 | 0.06 | 20.3 | 0.043 |
| | | 4.60 | 0.814 | 2403 | 0.06 | 20.4 | |
| | | 4.60 | 0.817 | 2403 | 0.06 | 20.4 | |
| | 1.009 | 4.60 | 0.820 | 2404 | 0.06 | 20.4 | |
| | | 4.60 | 0.823 | 2408 | 0.06 | 20.3 | |
| | | 4.60 | 0.825 | 2410 | 0.06 | 20.3 | 0.034 |
| | 1.009 | 4.60 | 0.828 | 2408 | 0.06 | 20.4 | |
| | | 4.60 | 0.831 | 2409 | 0.06 | 20.4 | |
| | | 4.60 | 0.834 | 2409 | 0.06 | 20.4 | |

FIG. 8HH

| | | | | | | | | | | | | | | | | | |
|---|---|---|---|---|---|---|---|---|---|---|---|---|---|---|---|---|---|
| 4 | 138.67 | 2.733 | 2.68 | 0 | 0.79 | 2.75 | 31 | 2.73 | | | | | | | | | 0.035 |
| | 138.83 | | | | | | | | | | | | | | | | |
| | 139.00 | | | | | | | | | 1.009 | 4.60 | 0.836 | 2405 | 0.06 | 20.4 | |
| 4 | 139.17 | 2.709 | 2.64 | 0 | 0.792 | 2.75 | 31 | 2.71 | | | 4.60 | 0.839 | 2405 | 0.05 | 20.4 | 0.032 |
| | 139.33 | | | | | | | | | | 4.60 | 0.842 | 2406 | 0.05 | 20.4 | |
| | 139.50 | | | | | | | | | 1.008 | 4.60 | 0.845 | 2403 | 0.05 | 20.5 | |
| 4 | 139.67 | 2.695 | 2.52 | 0 | 0.793 | 2.74 | 31 | 2.70 | | | 4.60 | 0.848 | 2404 | 0.05 | 20.5 | 0.073 |
| | 139.83 | | | | | | | | | | 4.60 | 0.851 | 2404 | 0.05 | 20.5 | |
| | 140.00 | | | | | | | | | 1.008 | 4.60 | 0.734 | 2351 | 0.05 | 20.5 | |
| 4 | 140.17 | 2.692 | | 0 | 0.793 | 2.72 | 30 | 2.69 | | | 4.60 | 0.732 | 2351 | 0.05 | 20.4 | 0.323 |
| | 140.33 | | | | | | | | | | 4.60 | 0.736 | 2353 | 0.05 | 20.4 | |
| | 140.50 | | | | | | | | | 1.008 | 4.60 | 0.740 | 2354 | 0.05 | 20.5 | |
| 4 | 140.67 | 2.672 | | 0 | 0.795 | 2.71 | 31 | 2.67 | | | 4.60 | 0.744 | 2362 | 0.05 | 20.4 | 0.105 |
| | 140.83 | | | | | | | | | | 4.60 | 0.748 | 2367 | 0.05 | 20.5 | |
| | 141.00 | | | | | | | | | 1.009 | 4.60 | 0.751 | 2370 | 0.05 | 20.5 | |
| 4 | 141.17 | 2.787 | | 0 | 0.786 | 2.97 | 30 | 2.79 | | | 4.62 | 0.753 | 2375 | 0.06 | 20.5 | 0.412 |
| | 141.33 | | | | | | | | | | 4.62 | 0.445 | 2376 | 0.06 | 20.4 | |
| | 141.50 | | | | | | | | | | 4.62 | 0.209 | 669 | 0.06 | 20.7 | |
| 4 | 141.67 | 2.87 | | 4.M | 0.78 | 2.87 | 17 | 2.45 | | | 4.62 | 0.178 | 1158 | 0.06 | 20.8 | 0.464 |
| | 141.83 | | | | | | | | | | 4.62 | 0.179 | 1335 | 0.06 | 20.9 | |
| | 142.00 | | | | | | | | | 1.008 | 4.62 | 0.180 | 2268 | 0.06 | 20.8 | |
| 4 | 142.17 | 2.593 | 2.93 | 0 | 0.801 | 2.8 | 20 | 2.59 | | | 4.62 | 0.179 | 2280 | 0.06 | 20.7 | 0.585 |
| | 142.33 | | | | | | | | | | 4.62 | 0.177 | 2273 | 0.06 | 20.8 | |
| | 142.50 | | | | | | | | | 1.008 | 4.62 | 0.230 | 2280 | 0.06 | 20.7 | |
| 4 | 142.67 | 2.618 | 2.44 | 0 | 0.799 | 2.67 | 28 | 2.62 | | | 4.62 | 0.323 | 2351 | 0.06 | 20.4 | 0.43 |
| | | | | | | | | | | | 4.62 | 0.339 | 2357 | 0.06 | 20.4 | |
| | | | | | | | | | | | 4.62 | 0.355 | 2363 | 0.06 | 20.4 | |

| | | | | | | | | | | | | | | | | |
|---|---|---|---|---|---|---|---|---|---|---|---|---|---|---|---|---|
| 4 | 142.83 | | | | | | | | | | | | | | | |
| | 143.00 | 2.624 | | | | | | | | | | | | | | |
| | 143.17 | | | 0.799 | 2.68 | 31 | 2.62 | | | 4.62 | 0.362 | 2374 | 0.06 | 20.4 | |
| | 143.33 | | | | | | | | 1.008 | 4.62 | 0.415 | 2440 | 0.05 | 20.6 | 0.112 |
| 4 | 143.50 | | | | | | | | | 4.62 | 0.417 | 2438 | 0.05 | 20.6 | |
| | 143.67 | 2.651 | 2.64 | 0.797 | 2.7 | 31 | 2.65 | | | 4.62 | 0.420 | 2441 | 0.05 | 20.5 | |
| | 143.83 | | | | | | | | 1.008 | 4.62 | 0.423 | 2440 | 0.05 | 20.4 | 0.047 |
| 4 | 144.00 | | | | | | | | | 4.62 | 0.426 | 2442 | 0.05 | 20.4 | |
| | 144.17 | 2.649 | | 0.797 | 2.7 | 31 | 2.65 | | | 4.62 | 0.429 | 2443 | 0.05 | 20.4 | |
| | 144.33 | | | | | | | | 1.008 | 4.62 | 0.433 | 2444 | 0.05 | 20.5 | 0.04 |
| 4 | 144.50 | | | | | | | | | 4.62 | 0.436 | 2440 | 0.05 | 20.5 | |
| | 144.67 | 2.659 | 2.5 | 0.796 | 2.69 | 31 | 2.66 | | | 4.62 | 0.439 | 2441 | 0.05 | 20.5 | |
| | 144.83 | | | | | | | | 1.008 | 4.62 | 0.442 | 2445 | 0.05 | 20.5 | 0.045 |
| 4 | 145.00 | | | | | | | | | 4.62 | 0.444 | 2443 | 0.05 | 20.5 | |
| | 145.17 | 2.641 | | 0.797 | 2.67 | 31 | 2.64 | | | 4.62 | 0.447 | 2445 | 0.06 | 20.5 | |
| | 145.33 | | | | | | | | 1.008 | 4.62 | 0.450 | 2446 | 0.06 | 20.5 | 0.038 |
| 4 | 145.50 | | | | | | | | | 4.62 | 0.451 | 2447 | 0.06 | 20.5 | |
| | 145.67 | 2.614 | 2.57 | 0.799 | 2.63 | 31 | 2.61 | | | 4.62 | 0.454 | 2448 | 0.06 | 20.5 | |
| | 145.83 | | | | | | | | 1.008 | 4.62 | 0.457 | 2450 | 0.06 | 20.5 | 0.037 |
| 4 | 146.00 | | | | | | | | | 4.62 | 0.460 | 2451 | 0.06 | 20.5 | |
| | 146.17 | 2.592 | | 0.801 | 2.63 | 31 | 2.59 | | | 4.62 | 0.462 | 2452 | 0.06 | 20.5 | |
| | 146.33 | | | | | | | | 1.008 | 4.62 | 0.464 | 2453 | 0.06 | 20.5 | 0.034 |
| 4 | 146.50 | | | | | | | | | 4.62 | 0.466 | 2454 | 0.06 | 20.5 | |
| | 146.67 | 2.583 | | 0.802 | 2.62 | 31 | 2.58 | | | 4.62 | 0.468 | 2455 | 0.06 | 20.5 | |
| | 146.83 | | | | | | | | 1.008 | 4.62 | 0.470 | 2459 | 0.05 | 20.5 | 0.034 |
| | | | | | | | | | | 4.62 | 0.473 | 2456 | 0.05 | 20.5 | |
| | | | | | | | | | | 4.62 | 0.475 | 2460 | 0.05 | 20.4 | |

FIG. 81II

| 4 | 147.00 | 2.589 | 2.52 |   |       |      | 31 |      |       |      | 4.62 | 0.476 | 2456 | 0.05 | 20.5 |       |
| 4 | 147.17 |       |      | 0 | 0.801 | 2.61 | 31 | 2.59 | 1.008 | 4.62 | 0.478 | 2460 | 0.05 | 20.4 | 0.041 |
|   | 147.33 |       |      |   |       |      |    |      |       |      | 4.62 | 0.480 | 2461 | 0.05 | 20.4 |       |
| 4 | 147.50 | 2.581 | 2.53 |   |       |      |    |      |       |      | 4.62 | 0.481 | 2462 | 0.05 | 20.4 |       |
| 4 | 147.67 |       |      | 0 | 0.802 | 2.6  | 31 | 2.58 | 1.008 | 4.62 | 0.483 | 2464 | 0.05 | 20.4 | 0.042 |
|   | 147.83 |       |      |   |       |      |    |      |       |      | 4.62 | 0.485 | 2467 | 0.05 | 20.4 |       |
| 4 | 148.00 | 2.576 | 2.53 |   |       |      |    |      |       | 4.63 | 0.487 | 2475 | 0.05 | 20.4 |       |
| 4 | 148.17 |       |      | 0 | 0.802 | 2.59 | 31 | 2.58 | 1.008 | 4.63 | 0.488 | 2485 | 0.06 | 20.4 | 0.039 |
|   | 148.33 |       |      |   |       |      |    |      |       |      | 4.63 | 0.490 | 2490 | 0.06 | 20.3 |       |
| 4 | 148.50 | 2.578 | 2.52 |   |       |      |    |      |       |      | 4.63 | 0.492 | 2498 | 0.06 | 20.4 |       |
| 4 | 148.67 |       |      | 0 | 0.802 | 2.6  | 31 | 2.58 | 1.008 | 4.63 | 0.493 | 2501 | 0.06 | 20.3 | 0.036 |
|   | 148.83 |       |      |   |       |      |    |      |       |      | 4.63 | 0.494 | 2499 | 0.06 | 20.4 |       |
| 4 | 149.00 | 2.583 | 2.54 |   |       |      |    |      |       |      | 4.63 | 0.496 | 2499 | 0.06 | 20.4 |       |
| 4 | 149.17 |       |      | 0 | 0.802 | 2.6  | 31 | 2.58 | 1.008 | 4.63 | 0.498 | 2500 | 0.06 | 20.4 | 0.039 |
|   | 149.33 |       |      |   |       |      |    |      |       |      | 4.63 | 0.500 | 2505 | 0.06 | 20.3 |       |
| 4 | 149.50 | 2.597 | 2.57 |   |       |      |    |      |       |      | 4.63 | 0.501 | 2506 | 0.06 | 20.3 |       |
| 4 | 149.67 |       |      | 0 | 0.801 | 2.61 | 31 | 2.60 | 1.008 | 4.63 | 0.503 | 2506 | 0.06 | 20.3 | 0.046 |
|   | 149.83 |       |      |   |       |      |    |      |       |      | 4.63 | 0.504 | 2507 | 0.06 | 20.3 |       |
| 4 | 150.00 | 2.605 | 2.57 |   |       |      |    |      |       |      | 4.63 | 0.506 | 2506 | 0.06 | 20.3 |       |
| 4 | 150.17 |       |      | 0 | 0.8   | 2.62 | 31 | 2.61 | 1.008 | 4.63 | 0.507 | 2506 | 0.05 | 20.3 | 0.045 |
|   | 150.33 |       |      |   |       |      |    |      |       |      | 4.63 | 0.508 | 2509 | 0.05 | 20.3 |       |
| 4 | 150.50 | 2.612 | 2.57 |   |       |      |    |      |       |      | 4.63 | 0.510 | 2509 | 0.05 | 20.3 |       |
| 4 | 150.67 |       |      | 0 | 0.8   | 2.64 | 31 | 2.61 | 1.008 | 4.63 | 0.511 | 2511 | 0.05 | 20.2 | 0.046 |
|   | 150.83 |       |      |   |       |      |    |      |       |      | 4.63 | 0.512 | 2511 | 0.05 | 20.2 |       |
|   | 151.00 |       |      |   |       |      |    |      |       |      | 4.63 | 0.514 | 2510 | 0.06 | 20.2 |       |

FIG. 8JJ

| | | | | | | | | | | | | | | | | | |
|---|---|---|---|---|---|---|---|---|---|---|---|---|---|---|---|---|---|
| 4 | 151.17 | 2.622 | 2.55 | 0 | 0.799 | 2.64 | 31 | 2.62 | | 1.008 | 4.63 | 0.516 | 2507 | 0.06 | 20.3 | 0.041 |
| | 151.33 | | | | | | | | | | 4.63 | 0.517 | 2510 | 0.06 | 20.2 | |
| | 151.50 | | | | | | | | | | 4.63 | 0.519 | 2508 | 0.06 | 20.3 | 0.029 |
| 4 | 151.67 | 2.597 | 2.59 | 0 | 0.801 | 2.61 | 31 | 2.60 | | | 4.63 | 0.521 | 2510 | 0.05 | 20.3 | |
| | 151.83 | | | | | | | | | | 4.63 | 0.522 | 2508 | 0.05 | 20.3 | |
| | 152.00 | | | | | | | | | | 4.63 | 0.524 | 2509 | 0.05 | 20.3 | 0.03 |
| 4 | 152.17 | 2.584 | 2.57 | 0 | 0.802 | 2.59 | 31 | 2.58 | | 1.008 | 4.63 | 0.525 | 2510 | 0.05 | 20.3 | |
| | 152.33 | | | | | | | | | | 4.63 | 0.527 | 2511 | 0.05 | 20.3 | |
| | 152.50 | | | | | | | | | | 4.63 | 0.528 | 2512 | 0.05 | 20.3 | 0.03 |
| 4 | 152.67 | 2.585 | 2.57 | 0 | 0.802 | 2.59 | 31 | 2.59 | | | 4.63 | 0.530 | 2510 | 0.06 | 20.4 | |
| | 152.83 | | | | | | | | | | 4.63 | 0.531 | 2510 | 0.05 | 20.4 | |
| | 153.00 | | | | | | | | | | 4.63 | 0.533 | 2511 | 0.06 | 20.4 | 0.033 |
| 4 | 153.17 | 2.582 | 2.59 | 0 | 0.802 | 2.59 | 31 | 2.58 | | 1.008 | 4.63 | 0.534 | 2512 | 0.05 | 20.4 | |
| | 153.33 | | | | | | | | | | 4.63 | 0.536 | 2515 | 0.06 | 20.3 | |
| | 153.50 | | | | | | | | | | 4.63 | 0.537 | 2516 | 0.06 | 20.3 | 0.032 |
| 4 | 153.67 | 2.584 | 2.55 | 0 | 0.802 | 2.59 | 31 | 2.58 | | | 4.63 | 0.539 | 2514 | 0.05 | 20.4 | |
| | 153.83 | | | | | | | | | | 4.63 | 0.540 | 2518 | 0.05 | 20.3 | |
| | 154.00 | | | | | | | | | | 4.63 | 0.542 | 2520 | 0.05 | 20.3 | 0.032 |
| 4 | 154.17 | 2.582 | 2.57 | 0 | 0.802 | 2.59 | 31 | 2.60 | | 1.008 | 4.63 | 0.543 | 2521 | 0.05 | 20.3 | |
| | 154.33 | | | | | | | | | | 4.63 | 0.544 | 2522 | 0.06 | 20.3 | |
| | 154.50 | | | | | | | | | | 4.63 | 0.546 | 2523 | 0.06 | 20.3 | 0.036 |
| 4 | 154.67 | 2.598 | 2.59 | 0 | 0.801 | 2.61 | 31 | 2.60 | | | 4.63 | 0.547 | 2523 | 0.06 | 20.3 | |
| | 154.83 | | | | | | | | | | 4.63 | 0.548 | 2624 | 0.05 | 20.3 | |
| | 155.00 | | | | | | | | | | 4.64 | 0.550 | 2528 | 0.05 | 20.3 | |
| 4 | 155.17 | 2.597 | 2.56 | 0 | 0.801 | 2.61 | 31 | 2.60 | | 1.008 | 4.63 | 0.551 | 2526 | 0.05 | 20.3 | 0.037 |

| | | | | | | | | | | | | | | |
|---|---|---|---|---|---|---|---|---|---|---|---|---|---|---|
| 155.33 | | | | | | | | | | | | | | |
| 155.50 | | | | | | | | | | | 0.552 | 2530 | 0.05 | 20.3 |
| 4 | 155.67 | 2.598 | 2.52 | 0 | 0.801 | 2.61 | 31 | 2.60 | | | 4.64 | 0.554 | 2527 | 0.05 | 20.3 | 0.039 |
| | 155.83 | | | | | | | | | 1.008 | 4.64 | 0.555 | 2527 | 0.06 | 20.3 | |
| | 156.00 | | | | | | | | | | 4.64 | 0.556 | 2531 | 0.06 | 20.3 | |
| 4 | 156.17 | 2.491 | 2.58 | 0 | 0.809 | 2.54 | 31 | 2.49 | | | 4.64 | 0.557 | 2532 | 0.06 | 20.3 | 0.023 |
| | 156.33 | | | | | | | | | | 4.64 | 0.559 | 2529 | 0.06 | 20.3 | |
| | 156.50 | | | | | | | | | 1.008 | 4.64 | 0.560 | 2533 | 0.06 | 20.3 | |
| 4 | 156.67 | 2.595 | 2.55 | 0 | 0.801 | 2.61 | 31 | 2.60 | | | 4.64 | 0.561 | 2534 | 0.06 | 20.3 | 0.049 |
| | 156.83 | | | | | | | | | | 4.64 | 0.562 | 2534 | 0.06 | 20.3 | |
| | 157.00 | | | | | | | | | 1.008 | 4.64 | 0.564 | 2532 | 0.06 | 20.3 | |
| 4 | 157.17 | 2.584 | 2.58 | 0 | 0.802 | 2.61 | 30 | 2.58 | | | 4.64 | 0.566 | 2536 | 0.06 | 20.3 | 0.032 |
| | 157.33 | | | | | | | | | | 4.64 | 0.567 | 2533 | 0.06 | 20.3 | |
| | 157.50 | | | | | | | | | 1.008 | 4.64 | 0.568 | 2534 | 0.06 | 20.3 | |
| 4 | 157.67 | 2.578 | 2.56 | 0 | 0.802 | 2.59 | 31 | 2.58 | | | 4.64 | 0.569 | 2534 | 0.06 | 20.3 | 0.029 |
| | 157.83 | | | | | | | | | | 4.64 | 0.571 | 2535 | 0.06 | 20.3 | |
| | 158.00 | | | | | | | | | 1.008 | 4.64 | 0.571 | 2539 | 0.06 | 20.3 | |
| 4 | 158.17 | 2.581 | 2.58 | 0 | 0.802 | 2.59 | 31 | 2.58 | | | 4.64 | 0.573 | 2536 | 0.06 | 20.3 | 0.028 |
| | 158.33 | | | | | | | | | | 4.64 | 0.575 | 2536 | 0.06 | 20.3 | |
| | 158.50 | | | | | | | | | 1.008 | 4.64 | 0.576 | 2537 | 0.06 | 20.3 | |
| 4 | 158.67 | 2.583 | 2.59 | 0 | 0.802 | 2.59 | 31 | 2.58 | | | 4.64 | 0.577 | 2537 | 0.06 | 20.3 | 0.03 |
| | 158.83 | | | | | | | | | | 4.64 | 0.578 | 2538 | 0.06 | 20.3 | |
| | 159.00 | | | | | | | | | 1.008 | 4.64 | 0.580 | 2542 | 0.05 | 20.3 | |
| 4 | 159.17 | 2.582 | 2.57 | 0 | 0.802 | 2.59 | 31 | 2.58 | | | 4.64 | 0.581 | 2539 | 0.05 | 20.3 | 0.032 |
| | 159.33 | | | | | | | | | | 4.64 | 0.582 | 2540 | 0.05 | 20.3 | |
| | | | | | | | | | | | 4.64 | 0.583 | 2540 | 0.05 | 20.3 | |

| | | | | | | | | | | | | | | | | | |
|---|---|---|---|---|---|---|---|---|---|---|---|---|---|---|---|---|---|
| 4 | 159.50 | | | | | | | | | | | | | | | | |
| | 159.67 | 2.583 | 2.57 | 0 | 0.802 | 2.59 | 31 | 2.58 | | | | 4.64 | 0.585 | 2541 | 0.05 | 20.3 | |
| | 159.83 | | | | | | | | | | 1.008 | 4.64 | 0.586 | 2541 | 0.06 | 20.3 | 0.031 |
| 4 | 160.00 | | | | | | | | | | | 4.64 | 0.587 | 2545 | 0.06 | 20.3 | |
| | 160.17 | 2.58 | 2.54 | 0 | 0.802 | 2.59 | 31 | 2.58 | | | | 4.64 | 0.588 | 2542 | 0.06 | 20.3 | |
| | 160.33 | | | | | | | | | | 1.008 | 4.64 | 0.589 | 2543 | 0.06 | 20.3 | 0.031 |
| | 160.50 | | | | | | | | | | | 4.64 | 0.589 | 2547 | 0.05 | 20.3 | |
| 4 | 160.67 | 2.58 | 2.57 | 0 | 0.802 | 2.59 | 31 | 2.58 | | | | 4.64 | 0.591 | 2544 | 0.05 | 20.3 | |
| | 160.83 | | | | | | | | | | 1.008 | 4.64 | 0.592 | 2545 | 0.05 | 20.3 | 0.029 |
| | 161.00 | | | | | | | | | | | 4.64 | 0.594 | 2545 | 0.05 | 20.3 | |
| 4 | 161.17 | 2.56 | 2.56 | 4M | 0.804 | 2.56 | 31 | 2.55 | | | | 4.64 | 0.595 | 2549 | 0.06 | 20.3 | |
| | 161.33 | | | | | | | | | | 1.008 | 4.64 | 0.596 | 2550 | 0.06 | 20.3 | 0.035 |
| | 161.50 | | | | | | | | | | | 4.64 | 0.597 | 2550 | 0.06 | 20.3 | |
| 4 | 161.67 | 2.571 | 2.56 | 0 | 0.803 | 2.59 | 31 | 2.57 | | | | 4.65 | 0.598 | 2547 | 0.06 | 20.3 | |
| | 161.83 | | | | | | | | | | 1.008 | 4.65 | 0.600 | 2548 | 0.06 | 20.3 | 0.032 |
| | 162.00 | | | | | | | | | | | 4.65 | 0.602 | 2551 | 0.06 | 20.3 | |
| 4 | 162.17 | 2.57 | 2.56 | 4M | 0.803 | 2.57 | 31 | 2.56 | | | | 4.65 | 0.603 | 2549 | 0.06 | 20.3 | |
| | 162.33 | | | | | | | | | | 1.008 | 4.64 | 0.604 | 2550 | 0.06 | 20.3 | 0.016 |
| | 162.50 | | | | | | | | | | | 4.65 | 0.607 | 2547 | 0.06 | 20.4 | |
| 4 | 162.67 | 2.57 | 2.54 | 4M | 0.803 | 2.57 | 31 | 2.54 | | | | 4.65 | 0.609 | 2543 | 0.06 | 20.4 | |
| | 162.83 | | | | | | | | | | 1.008 | 4.65 | 0.612 | 2538 | 0.05 | 20.6 | 0.018 |
| | 163.00 | | | | | | | | | | | 4.65 | 0.615 | 2542 | 0.05 | 20.5 | |
| 4 | 163.17 | 2.499 | 2.51 | 0 | 0.808 | 2.55 | 30 | 2.50 | | | | 4.65 | 0.617 | 2536 | 0.05 | 20.6 | |
| | 163.33 | | | | | | | | | | 1.007 | 4.65 | 0.620 | 2535 | 0.06 | 20.7 | 0.021 |
| | 163.50 | | | | | | | | | | | 4.65 | 0.623 | 2536 | 0.06 | 20.7 | |
| | | | | | | | | | | | | 4.65 | 0.626 | 2534 | 0.05 | 20.8 | |

| | | | | | | | | | | | | | | | | | |
|---|---|---|---|---|---|---|---|---|---|---|---|---|---|---|---|---|---|
| 4 | 163.67 | 2.477 | 2.5 | 0 | 0.81 | 2.55 | 31 | 2.48 | | 1.007 | 4.65 | 0.628 | 2536 | 0.06 | 20.8 | 0.025 |
| 4 | 163.83 | | | | | | | | | | | 0.630 | 2537 | 0.06 | 20.8 | |
| 4 | 164.00 | | | | | | | | | | 4.65 | 0.633 | 2538 | 0.06 | 20.8 | 0.031 |
| 4 | 164.17 | 2.464 | | 0 | 0.811 | 2.54 | 31 | 2.46 | | 1.007 | 4.66 | 0.635 | 2537 | 0.06 | 20.8 | |
| 4 | 164.33 | | | | | | | | | | 4.66 | 0.637 | 2540 | 0.05 | 20.8 | |
| 4 | 164.50 | | | | | | | | | | 4.66 | 0.638 | 2541 | 0.05 | 20.8 | 0.033 |
| 4 | 164.67 | 2.471 | | 0 | 0.81 | 2.52 | 31 | 2.47 | | 1.007 | 4.66 | 0.639 | 2542 | 0.06 | 20.8 | |
| 4 | 164.83 | | | | | | | | | | 4.66 | 0.641 | 2542 | 0.06 | 20.8 | |
| 4 | 165.00 | | | | | | | | | | 4.66 | 0.641 | 2543 | 0.06 | 20.8 | 0.026 |
| 4 | 165.17 | 2.462 | 2.45 | 0 | 0.811 | 2.52 | 31 | 2.46 | | 1.008 | 4.66 | 0.640 | 2542 | 0.06 | 20.8 | |
| 4 | 165.33 | | | | | | | | | | 4.66 | 0.639 | 2547 | 0.06 | 20.7 | |
| 4 | 165.50 | | | | | | | | | | 4.66 | 0.641 | 2550 | 0.06 | 20.6 | 0.028 |
| 4 | 165.67 | 2.477 | 2.48 | 0 | 0.81 | 2.54 | 31 | 2.48 | | 1.007 | 4.66 | 0.642 | 2547 | 0.06 | 20.7 | |
| 4 | 165.83 | | | | | | | | | | 4.66 | 0.643 | 2549 | 0.06 | 20.6 | |
| 4 | 166.00 | | | | | | | | | | 4.66 | 0.644 | 2549 | 0.06 | 20.6 | 0.022 |
| 4 | 166.17 | 2.484 | 2.5 | 0 | 0.809 | 2.53 | 31 | 2.48 | | 1.007 | 4.66 | 0.646 | 2544 | 0.06 | 20.8 | |
| 4 | 166.33 | | | | | | | | | | 4.66 | 0.647 | 2545 | 0.06 | 20.8 | |
| 4 | 166.50 | | | | | | | | | | 4.66 | 0.650 | 2548 | 0.06 | 20.8 | 0.022 |
| 4 | 166.67 | 2.481 | 2.46 | 0 | 0.81 | 2.54 | 31 | 2.48 | | 1.007 | 4.66 | 0.651 | 2550 | 0.06 | 20.8 | |
| 4 | 166.83 | | | | | | | | | | 4.66 | 0.652 | 2551 | 0.06 | 20.8 | |
| 4 | 167.00 | | | | | | | | | | 4.66 | 0.654 | 2552 | 0.06 | 20.8 | 0.021 |
| 4 | 167.17 | 2.483 | 2.48 | 0 | 0.809 | 2.53 | 31 | 2.48 | | 1.007 | 4.66 | 0.655 | 2553 | 0.06 | 20.8 | |
| 4 | 167.33 | | | | | | | | | | 4.66 | 0.656 | 2552 | 0.06 | 20.8 | |
| 4 | 167.50 | | | | | | | | | | 4.66 | 0.657 | 2555 | 0.06 | 20.7 | |
| 4 | 167.67 | 2.504 | 2.46 | 0 | 0.808 | 2.54 | 31 | 2.50 | | 1.008 | 4.66 | 0.657 | 2553 | 0.06 | 20.8 | 0.023 |

| | | | | | | | | | | | | | | | | | |
|---|---|---|---|---|---|---|---|---|---|---|---|---|---|---|---|---|---|
| 4 | 167.83 | | | | | | | | | | | | | | | | |
| | 168.00 | 2.494 | 2.49 | 0 | 0.809 | 2.54 | 31 | 2.49 | | | 4.66 | 0.658 | 2555 | 0.06 | 20.7 | |
| | 168.17 | | | | | | | | | | 4.66 | 0.659 | 2555 | 0.06 | 20.7 | 0.021 |
| | 168.33 | | | | | | | | | 1.008 | 4.66 | 0.660 | 2557 | 0.06 | 20.7 | |
| | 168.50 | | | | | | | | | | 4.66 | 0.661 | 2557 | 0.06 | 20.7 | |
| 4 | 168.67 | 2.488 | 2.49 | 0 | 0.809 | 2.53 | 31 | 2.49 | | | 4.66 | 0.662 | 2557 | 0.06 | 20.7 | 0.018 |
| | 168.83 | | | | | | | | | | 4.66 | 0.664 | 2559 | 0.06 | 20.7 | |
| | 169.00 | | | | | | | | | 1.008 | 4.66 | 0.664 | 2559 | 0.06 | 20.7 | |
| 4 | 169.17 | 2.497 | 2.47 | 0 | 0.808 | 2.53 | 31 | 2.50 | | | 4.66 | 0.665 | 2559 | 0.06 | 20.7 | 0.016 |
| | 169.33 | | | | | | | | | | 4.66 | 0.665 | 2560 | 0.06 | 20.7 | |
| | 169.50 | | | | | | | | | 1.008 | 4.66 | 0.667 | 2559 | 0.06 | 20.6 | |
| 4 | 169.67 | 2.494 | 2.5 | 0 | 0.809 | 2.54 | 31 | 2.49 | | | 4.66 | 0.668 | 2563 | 0.05 | 20.7 | 0.02 |
| | 169.83 | | | | | | | | | | 4.66 | 0.669 | 2561 | 0.05 | 20.6 | |
| | 170.00 | | | | | | | | | 1.008 | 4.66 | 0.669 | 2564 | 0.05 | 20.7 | |
| 4 | 170.17 | 2.51 | 2.51 | 0 | 0.807 | 2.54 | 31 | 2.51 | | | 4.66 | 0.670 | 2561 | 0.05 | 20.6 | 0.022 |
| | 170.33 | | | | | | | | | | 4.66 | 0.671 | 2565 | 0.05 | 20.6 | |
| | 170.50 | | | | | | | | | 1.008 | 4.66 | 0.672 | 2565 | 0.05 | 20.6 | |
| 4 | 170.67 | 2.496 | 2.47 | 0 | 0.808 | 2.55 | 31 | 2.50 | | | 4.66 | 0.673 | 2565 | 0.05 | 20.7 | 0.027 |
| | 170.83 | | | | | | | | | | 4.66 | 0.674 | 2563 | 0.05 | 20.6 | |
| | 171.00 | | | | | | | | | 1.008 | 4.66 | 0.674 | 2566 | 0.05 | 20.6 | |
| 4 | 171.17 | 2.53 | 2.51 | 0 | 0.806 | 2.54 | 31 | 2.53 | | | 4.66 | 0.675 | 2566 | 0.05 | 20.6 | 0.027 |
| | 171.33 | | | | | | | | | | 4.66 | 0.675 | 2567 | 0.05 | 20.6 | |
| | 171.50 | | | | | | | | | 1.008 | 4.66 | 0.676 | 2565 | 0.05 | 20.6 | |
| 4 | 171.67 | 2.542 | 2.48 | 0 | 0.805 | 2.55 | 31 | 2.54 | | | 4.66 | 0.677 | 2565 | 0.06 | 20.6 | 0.028 |
| | 171.83 | | | | | | | | | | 4.66 | 0.677 | 2569 | 0.06 | 20.6 | |
| | | | | | | | | | | | 4.66 | | 2571 | | 20.5 | |

FIG. 800

| | | | | | | | | | | | | | | | |
|---|---|---|---|---|---|---|---|---|---|---|---|---|---|---|---|
| 4 | 172.00 | | | | | | | | | | | | | | |
| 4 | 172.17 | 2.542 | 2.48 | 0 | 0.805 | 2.55 | 31 | 2.54 | 1.008 | 4.66 | 0.678 | 2571 | 0.06 | 20.5 | 0.029 |
| 4 | 172.33 | | | | | | | | | 4.66 | 0.678 | 2568 | 0.06 | 20.6 | |
| 4 | 172.50 | 2.546 | 2.5 | 0 | 0.805 | 2.55 | 30 | 2.55 | | 4.66 | 0.679 | 2572 | 0.06 | 20.5 | |
| 4 | 172.67 | | | | | | | | 1.008 | 4.66 | 0.679 | 2569 | 0.06 | 20.6 | 0.025 |
| 4 | 172.83 | | | | | | | | | 4.66 | 0.680 | 2567 | 0.06 | 20.6 | |
| 4 | 173.00 | 2.542 | 2.5 | 0 | 0.805 | 2.55 | 31 | 2.54 | | 4.66 | 0.681 | 2569 | 0.06 | 20.6 | |
| 4 | 173.17 | | | | | | | | 1.008 | 4.66 | 0.682 | 2574 | 0.06 | 20.6 | 0.025 |
| 4 | 173.33 | | | | | | | | | 4.66 | 0.683 | 2574 | 0.06 | 20.6 | |
| 4 | 173.50 | 2.527 | 2.54 | 0 | 0.806 | 2.55 | 31 | 2.53 | | 4.66 | 0.684 | 2573 | 0.06 | 20.6 | |
| 4 | 173.67 | | | | | | | | 1.008 | 4.66 | 0.684 | 2572 | 0.06 | 20.6 | 0.022 |
| 4 | 173.83 | | | | | | | | | 4.66 | 0.686 | 2571 | 0.06 | 20.6 | |
| 4 | 174.00 | 2.56 | 2.5 | 4.M | 0.804 | 2.56 | 31 | 2.55 | | 4.66 | 0.686 | 2571 | 0.06 | 20.6 | |
| 4 | 174.17 | | | | | | | | 1.008 | 4.66 | 0.687 | 2572 | 0.06 | 20.6 | 0.029 |
| 4 | 174.33 | | | | | | | | | 4.66 | 0.688 | 2572 | 0.06 | 20.6 | |
| 4 | 174.50 | 2.56 | 2.52 | 4.M | 0.804 | 2.56 | 31 | 2.55 | | 4.66 | 0.689 | 2571 | 0.06 | 20.6 | |
| 4 | 174.67 | | | | | | | | 1.008 | 4.66 | 0.690 | 2574 | 0.06 | 20.6 | 0.025 |
| 4 | 174.83 | | | | | | | | | 4.66 | 0.691 | 2573 | 0.06 | 20.6 | |
| 4 | 175.00 | 2.56 | 2.52 | 4.M | 0.804 | 2.56 | 31 | 2.55 | | 4.66 | 0.692 | 2573 | 0.06 | 20.6 | |
| 4 | 175.17 | | | | | | | | 1.008 | 4.66 | 0.693 | 2573 | 0.06 | 20.6 | 0.024 |
| 4 | 175.33 | | | | | | | | | 4.66 | 0.694 | 2575 | 0.06 | 20.6 | |
| 4 | 175.50 | 2.56 | 2.5 | 4.M | 0.804 | 2.56 | 31 | 2.55 | | 4.66 | 0.695 | 2575 | 0.06 | 20.6 | |
| 4 | 175.67 | | | | | | | | 1.008 | 4.66 | 0.696 | 2575 | 0.06 | 20.6 | 0.027 |
| 4 | 175.83 | | | | | | | | | 4.66 | 0.696 | 2574 | 0.06 | 20.6 | |
| 4 | 176.00 | | | | | | | | | 4.66 | 0.698 | 2575 | 0.06 | 20.6 | |

| 4 | 176.17 | 2.53 | 2.52 | 0 | 0.806 | 2.54 | 31 | 2.53 | | | | | | | 0.700 | 2572 | 0.06 | 20.6 | 0.02 |
|---|---|---|---|---|---|---|---|---|---|---|---|---|---|---|---|---|---|---|
| | 176.33 | | | | | | | | | | 1.008 | 4.66 | | 0.701 | 2574 | 0.06 | 20.6 | |
| | 176.50 | | | | | | | | | | | 4.66 | | 0.702 | 2576 | 0.06 | 20.6 | |
| 4 | 176.67 | 2.56 | 2.53 | 4.M | 0.804 | 2.56 | 31 | 2.53 | | | | 4.67 | | 0.703 | 2576 | 0.06 | 20.6 | 0.024 |
| | 176.83 | | | | | | | | | | | 4.67 | | 0.704 | 2576 | 0.06 | 20.6 | |
| | 177.00 | | | | | | | | | | | 4.67 | | 0.705 | 2579 | 0.06 | 20.6 | |
| 4 | 177.17 | 2.56 | 2.49 | 4.M | 0.804 | 2.56 | 31 | 2.54 | | | 1.008 | 4.66 | | 0.707 | 2579 | 0.06 | 20.9 | 0.03 |
| | 177.33 | | | | | | | | | | | 4.66 | | 0.707 | 2578 | 0.06 | 20.9 | |
| | 177.50 | | | | | | | | | | | 4.66 | | 0.709 | 2585 | 0.06 | 20.7 | |
| 4 | 177.67 | 2.57 | 2.51 | 4.M | 0.803 | 2.57 | 31 | 2.55 | | | 1.008 | 4.66 | | 0.709 | 2583 | 0.06 | 20.7 | 0.033 |
| | 177.83 | | | | | | | | | | | 4.67 | | 0.710 | 2584 | 0.06 | 20.6 | |
| | 178.00 | | | | | | | | | | | 4.67 | | 0.711 | 2582 | 0.06 | 20.6 | |
| 4 | 178.17 | 2.57 | 2.51 | 4.M | 0.803 | 2.57 | 31 | 2.56 | | | 1.008 | 4.67 | | 0.711 | 2577 | 0.06 | 20.6 | 0.032 |
| | 178.33 | | | | | | | | | | | 4.67 | | 0.713 | 2577 | 0.06 | 20.6 | |
| | 178.50 | | | | | | | | | | | 4.67 | | 0.714 | 2577 | 0.06 | 20.6 | |
| 4 | 178.67 | 2.57 | 2.49 | 4.M | 0.803 | 2.57 | 30 | 2.56 | | | 1.008 | 4.67 | | 0.715 | 2577 | 0.06 | 20.6 | 0.03 |
| | 178.83 | | | | | | | | | | | 4.67 | | 0.716 | 2578 | 0.06 | 20.6 | |
| | 179.00 | | | | | | | | | | | 4.67 | | 0.718 | 2579 | 0.06 | 20.8 | |
| 4 | 179.17 | 2.57 | 2.53 | 4.M | 0.803 | 2.57 | 31 | 2.55 | | | 1.008 | 4.66 | | 0.718 | 2573 | 0.06 | 20.7 | 0.03 |
| | 179.33 | | | | | | | | | | | 4.66 | | 0.719 | 2578 | 0.06 | 20.7 | |
| | 179.50 | | | | | | | | | | | 4.67 | | 0.721 | 2578 | 0.06 | 20.6 | |
| 4 | 179.67 | 2.56 | 2.44 | 4.M | 0.804 | 2.56 | 31 | 2.54 | | | 1.008 | 4.67 | | 0.722 | 2581 | 0.06 | 20.6 | 0.024 |
| | 179.83 | | | | | | | | | | | 4.67 | | 0.722 | 2579 | 0.06 | 20.6 | |
| | 180.00 | | | | | | | | | | | 4.67 | | 0.723 | 2582 | 0.06 | 20.6 | |
| 4 | 180.17 | 2.56 | 2.46 | 4.M | 0.804 | 2.56 | 31 | 2.53 | | | 1.008 | 4.67 | | 0.724 | 2581 | 0.06 | 20.6 | 0.025 |

| | | | | | | | | | | | | | | | | |
|---|---|---|---|---|---|---|---|---|---|---|---|---|---|---|---|---|
| | | | | | | | | | | | 4.67 | 0.726 | 2582 | 0.06 | 20.6 | |
| | | | | | | | | | | | 4.67 | 0.727 | 2578 | 0.05 | 20.6 | 0.026 |
| | | | | | | | | | | 1.008 | 4.67 | 0.728 | 2590 | 0.05 | 20.8 | |
| | | | | | | | | | | | 4.67 | 0.728 | 2586 | 0.05 | 20.8 | |
| | | | | | | | | | | | 4.67 | 0.729 | 2591 | 0.05 | 20.6 | 0.029 |
| | | | | | | | | | | 1.008 | 4.67 | 0.730 | 2588 | 0.05 | 20.6 | |
| | | | | | | | | | | | 4.67 | 0.731 | 2586 | 0.05 | 20.6 | |
| | | | | | | | | | | | 4.67 | 0.731 | 2585 | 0.05 | 20.6 | 0.027 |
| | | | | | | | | | | 1.008 | 4.67 | 0.732 | 2585 | 0.06 | 20.6 | |
| | | | | | | | | | | | 4.67 | 0.734 | 2586 | 0.06 | 20.6 | |
| | | | | | | | | | | | 4.66 | 0.735 | 2586 | 0.06 | 20.6 | 0.028 |
| | | | | | | | | | | 1.008 | 4.67 | 0.735 | 2582 | 0.06 | 20.9 | |
| | | | | | | | | | | | 4.67 | 0.737 | 2586 | 0.05 | 20.9 | |
| | | | | | | | | | | | 4.67 | 0.737 | 2582 | 0.06 | 20.8 | 0.037 |
| | | | | | | | | | | 1.008 | 4.67 | 0.737 | 2586 | 0.06 | 20.6 | |
| | | | | | | | | | | | 4.67 | 0.738 | 2591 | 0.06 | 20.6 | |
| | | | | | | | | | | | 4.67 | 0.738 | 2587 | 0.06 | 20.6 | 0.033 |
| | | | | | | | | | | 1.008 | 4.67 | 0.739 | 2586 | 0.06 | 20.6 | |
| | | | | | | | | | | | 4.67 | 0.740 | 2588 | 0.06 | 20.6 | |
| | | | | | | | | | | | 4.67 | 0.741 | 2581 | 0.06 | 20.6 | 0.031 |
| | | | | | | | | | | 1.008 | 4.67 | 0.742 | 2581 | 0.06 | 20.6 | |
| | | | | | | | | | | | 4.67 | 0.742 | 2586 | 0.06 | 20.6 | |
| | | | | | | | | | | | 4.67 | 0.744 | 2583 | 0.06 | 20.6 | 0.027 |
| | | | | | | | | | | 1.008 | 4.67 | 0.746 | 2581 | 0.06 | 20.6 | |
| | | | | | | | | | | | 4.67 | 0.746 | 2596 | 0.06 | 20.8 | |
| 4 | 180.33 | | | | | | | | | | | | | | | |
| | 180.50 | | | | | | | | | | | | | | | |
| | 180.67 | 2.56 | 2.5 | 4.M | 0.804 | 2.56 | 31 | 2.53 | | | | | | | | |
| | 180.83 | | | | | | | | | | | | | | | |
| 4 | 181.00 | | | | | | | | | | | | | | | |
| | 181.17 | 2.56 | 2.48 | 4.M | 0.804 | 2.56 | 31 | 2.55 | | | | | | | | |
| | 181.33 | | | | | | | | | | | | | | | |
| 4 | 181.50 | | | | | | | | | | | | | | | |
| | 181.67 | 2.56 | 2.5 | 4.M | 0.804 | 2.56 | 31 | 2.53 | | | | | | | | |
| | 181.83 | | | | | | | | | | | | | | | |
| 4 | 182.00 | | | | | | | | | | | | | | | |
| | 182.17 | 2.56 | 2.52 | 4.M | 0.804 | 2.56 | 31 | 2.54 | | | | | | | | |
| | 182.33 | | | | | | | | | | | | | | | |
| 4 | 182.50 | | | | | | | | | | | | | | | |
| | 182.67 | 2.573 | 2.47 | 0 | 0.803 | 2.58 | 31 | 2.57 | | | | | | | | |
| | 182.83 | | | | | | | | | | | | | | | |
| 4 | 183.00 | | | | | | | | | | | | | | | |
| | 183.17 | 2.575 | 2.5 | 0 | 0.802 | 2.58 | 31 | 2.58 | | | | | | | | |
| | 183.33 | | | | | | | | | | | | | | | |
| 4 | 183.50 | | | | | | | | | | | | | | | |
| | 183.67 | 2.58 | 2.46 | 4.M | 0.802 | 2.58 | 31 | 2.56 | | | | | | | | |
| | 183.83 | | | | | | | | | | | | | | | |
| 4 | 184.00 | | | | | | | | | | | | | | | |
| | 184.17 | 2.543 | 2.47 | 0 | 0.805 | 2.55 | 31 | 2.54 | | | | | | | | |
| | 184.33 | | | | | | | | | | | | | | | |

| | | | | | | | | | | | | | | | | | |
|---|---|---|---|---|---|---|---|---|---|---|---|---|---|---|---|---|---|
| 4 | 184.50 | | | | | | | | | | | | | | | | |
| 4 | 184.67 | 2.537 | 2.53 | 0 | 0.805 | 2.55 | 31 | 2.54 | | | 4.67 | 0.746 | 2592 | 0.06 | 20.8 | 0.027 |
| | 184.83 | | | | | | | | | | 4.67 | 0.746 | 2595 | 0.06 | 20.7 | |
| | 185.00 | | | | | | | | | 1.008 | 4.67 | 0.747 | 2595 | 0.06 | 20.6 | |
| 4 | 185.17 | 2.57 | 2.45 | 4.M | 0.803 | 2.57 | 31 | 2.55 | | | 4.67 | 0.748 | 2593 | 0.06 | 20.6 | 0.027 |
| | 185.33 | | | | | | | | | | 4.67 | 0.749 | 2596 | 0.06 | 20.6 | |
| | 185.50 | | | | | | | | | 1.008 | 4.67 | 0.749 | 2596 | 0.06 | 20.6 | |
| 4 | 185.67 | 2.546 | 2.48 | 0 | 0.805 | 2.55 | 31 | 2.55 | | | 4.67 | 0.750 | 2592 | 0.06 | 20.6 | 0.026 |
| | 185.83 | | | | | | | | | | 4.67 | 0.751 | 2592 | 0.06 | 20.6 | |
| | 186.00 | | | | | | | | | 1.008 | 4.67 | 0.752 | 2592 | 0.06 | 20.6 | |
| 4 | 186.17 | 2.56 | 2.49 | 4.M | 0.804 | 2.56 | 31 | 2.54 | | | 4.67 | 0.755 | 2595 | 0.06 | 20.9 | 0.027 |
| | 186.33 | | | | | | | | | | 4.67 | 0.756 | 2590 | 0.06 | 21.1 | |
| | 186.50 | | | | | | | | | 1.008 | 4.67 | 0.756 | 2586 | 0.06 | 20.9 | |
| 4 | 186.67 | 2.513 | 2.49 | 0 | 0.807 | 2.55 | 31 | 2.51 | | | 4.67 | 0.757 | 2589 | 0.06 | 20.8 | 0.024 |
| | 186.83 | | | | | | | | | | 4.67 | 0.758 | 2592 | 0.05 | 20.8 | |
| | 187.00 | | | | | | | | | 1.008 | 4.67 | 0.759 | 2593 | 0.06 | 20.7 | |
| 4 | 187.17 | 2.515 | 2.45 | 0 | 0.807 | 2.55 | 31 | 2.52 | | | 4.67 | 0.760 | 2594 | 0.06 | 20.6 | 0.022 |
| | 187.33 | | | | | | | | | | 4.67 | 0.761 | 2587 | 0.06 | 20.8 | |
| | 187.50 | | | | | | | | | 1.008 | 4.67 | 0.763 | 2587 | 0.05 | 20.8 | |
| 4 | 187.67 | 2.505 | 2.45 | 0 | 0.808 | 2.54 | 31 | 2.51 | | | 4.67 | 0.764 | 2585 | 0.05 | 20.8 | 0.02 |
| | 187.83 | | | | | | | | | | 4.67 | 0.766 | 2587 | 0.05 | 20.8 | |
| | 188.00 | | | | | | | | | 1.008 | 4.67 | 0.768 | 2587 | 0.05 | 20.8 | |
| 4 | 188.17 | 2.499 | 2.45 | 0 | 0.808 | 2.55 | 30 | 2.50 | | | 4.67 | 0.770 | 2584 | 0.05 | 21.4 | 0.021 |
| | 188.33 | | | | | | | | | | 4.67 | 0.771 | 2583 | 0.06 | 21.5 | |
| | 188.50 | | | | | | | | | | 4.67 | 0.772 | 2585 | 0.06 | 21.1 | |
| | | | | | | | | | | | 4.67 | 0.774 | 2589 | 0.06 | 20.9 | |

FIG. 8TT

| | | | | | | | | | | | | | | | | | |
|---|---|---|---|---|---|---|---|---|---|---|---|---|---|---|---|---|---|
| 4 | 188.67 | 2.493 | 2.51 | 0 | 0.809 | 2.53 | 31 | 2.49 | 1.007 | 4.67 | 0.774 | 2592 | 0.06 | 20.9 | 0.024 |
| 4 | 188.83 | | | | | | | | | 4.68 | 0.776 | 2586 | 0.06 | 20.9 | |
| 4 | 189.00 | | | | | | | | | 4.68 | 0.777 | 2588 | 0.06 | 20.8 | |
| 4 | 189.17 | 2.504 | 2.42 | 0 | 0.808 | 2.54 | 31 | 2.50 | 1.007 | 4.68 | 0.778 | 2584 | 0.06 | 20.9 | 0.025 |
| 4 | 189.33 | | | | | | | | | 4.67 | 0.781 | 2587 | 0.05 | 21.4 | |
| 4 | 189.50 | | | | | | | | | 4.67 | 0.783 | 2589 | 0.06 | 21.3 | |
| 4 | 189.67 | 2.488 | 2.47 | 0 | 0.809 | 2.52 | 31 | 2.49 | 1.007 | 4.67 | 0.784 | 2589 | 0.06 | 21.3 | 0.046 |
| 4 | 189.83 | | | | | | | | | 4.68 | 0.786 | 2585 | 0.06 | 21.0 | |
| 4 | 190.00 | | | | | | | | | 4.68 | 0.786 | 2585 | 0.06 | 21.0 | |
| 4 | 190.17 | 2.491 | 2.49 | 0 | 0.809 | 2.52 | 31 | 2.49 | 1.007 | 4.67 | 0.788 | 2583 | 0.06 | 21.1 | 0.023 |
| 4 | 190.33 | | | | | | | | | 4.68 | 0.789 | 2584 | 0.06 | 21.1 | |
| 4 | 190.50 | | | | | | | | | 4.68 | 0.790 | 2587 | 0.06 | 21.0 | |
| 4 | 190.67 | 2.482 | 2.41 | 0 | 0.81 | 2.52 | 31 | 2.48 | 1.007 | 4.68 | 0.793 | 2583 | 0.06 | 21.1 | 0.03 |
| 4 | 190.83 | | | | | | | | | 4.67 | 0.794 | 2582 | 0.06 | 21.0 | |
| 4 | 191.00 | | | | | | | | | 4.67 | 0.796 | 2569 | 0.06 | 21.7 | |
| 4 | 191.17 | 2.473 | 2.44 | 0 | 0.81 | 2.54 | 31 | 2.47 | 1.007 | 4.68 | 0.797 | 2592 | 0.06 | 21.6 | 0.046 |
| 4 | 191.33 | | | | | | | | | 4.68 | 0.799 | 2586 | 0.05 | 21.4 | |
| 4 | 191.50 | | | | | | | | | 4.68 | 0.800 | 2591 | 0.06 | 21.1 | |
| 4 | 191.67 | 2.468 | 2.41 | 0 | 0.811 | 2.51 | 31 | 2.47 | 1.007 | 4.68 | 0.801 | 2593 | 0.06 | 21.1 | 0.035 |
| 4 | 191.83 | | | | | | | | | 4.68 | 0.803 | 2592 | 0.06 | 21.1 | |
| 4 | 192.00 | | | | | | | | | 4.68 | 0.804 | 2592 | 0.06 | 21.1 | |
| 4 | 192.17 | 2.458 | 2.39 | 0 | 0.811 | 2.5 | 31 | 2.46 | 1.007 | 4.68 | 0.805 | 2588 | 0.06 | 21.1 | 0.056 |
| 4 | 192.33 | | | | | | | | | 4.68 | 0.806 | 2589 | 0.06 | 21.1 | |
| 4 | 192.50 | | | | | | | | | 4.67 | 0.809 | 2566 | 0.05 | 22.3 | |
| 4 | 192.67 | 2.483 | 2.42 | 0 | 0.809 | 2.52 | 31 | 2.48 | 1.007 | 4.67 | 0.810 | 2569 | 0.05 | 22.5 | 0.053 |

FIG. 8UU

| | | | | | | | | | | | | | | |
|---|---|---|---|---|---|---|---|---|---|---|---|---|---|---|
| 192.83 | | | | | | | | | | | | | | |
| 193.00 | 4 | 2.45 | 2.38 | 0 | 0.812 | 2.52 | 31 | 2.45 | | | 4.68 | 0.810 | 2579 | 0.06 | 21.8 |
| 193.17 | | | | | | | | | | 1.007 | 4.68 | 0.811 | 2585 | 0.06 | 21.1 | 0.031 |
| 193.33 | | | | | | | | | | | 4.68 | 0.811 | 2587 | 0.06 | 21.1 |
| 193.50 | | | | | | | | | | | 4.68 | 0.812 | 2593 | 0.06 | 20.9 |
| 193.67 | 4 | 2.485 | 2.46 | 0 | 0.809 | 2.53 | 31 | 2.49 | | | 4.68 | 0.813 | 2588 | 0.06 | 21.0 |
| 193.83 | | | | | | | | | | 1.007 | 4.68 | 0.813 | 2585 | 0.06 | 21.1 | 0.035 |
| 194.00 | | | | | | | | | | | 4.68 | 0.814 | 2590 | 0.06 | 21.0 |
| 194.17 | 4 | 2.453 | 2.43 | 0 | 0.812 | 2.52 | 30 | 2.45 | | | 4.68 | 0.815 | 2590 | 0.06 | 21.0 |
| 194.33 | | | | | | | | | | 1.007 | 4.67 | 0.817 | 2590 | 0.06 | 21.7 | 0.03 |
| 194.50 | | | | | | | | | | | 4.68 | 0.818 | 2589 | 0.06 | 21.6 |
| 194.67 | 4 | 2.47 | 2.41 | 0 | 0.81 | 2.5 | 31 | 2.47 | | | 4.68 | 0.819 | 2581 | 0.06 | 21.4 |
| 194.83 | | | | | | | | | | 1.007 | 4.68 | 0.819 | 2594 | 0.06 | 21.1 | 0.044 |
| 195.00 | | | | | | | | | | | 4.68 | 0.818 | 2591 | 0.06 | 21.1 |
| 195.17 | 4 | 2.481 | 2.39 | 0 | 0.81 | 2.52 | 31 | 2.48 | | | 4.68 | 0.819 | 2591 | 0.06 | 21.0 |
| 195.33 | | | | | | | | | | 1.007 | 4.68 | 0.819 | 2595 | 0.06 | 20.9 | 0.026 |
| 195.50 | | | | | | | | | | | 4.68 | 0.819 | 2594 | 0.06 | 20.9 |
| 195.67 | 4 | 2.491 | 2.42 | 0 | 0.809 | 2.51 | 31 | 2.49 | | | 4.68 | 0.820 | 2591 | 0.06 | 21.0 |
| 195.83 | | | | | | | | | | 1.007 | 4.68 | 0.821 | 2595 | 0.06 | 20.9 | 0.03 |
| 196.00 | | | | | | | | | | | 4.68 | 0.822 | 2596 | 0.06 | 20.9 |
| 196.17 | 4 | 2.489 | 2.43 | 0 | 0.809 | 2.52 | 31 | 2.49 | | | 4.68 | 0.823 | 2589 | 0.06 | 21.0 |
| 196.33 | | | | | | | | | | 1.007 | 4.68 | 0.824 | 2593 | 0.06 | 21.5 | 0.033 |
| 196.50 | | | | | | | | | | | 4.67 | 0.824 | 2581 | 0.06 | 21.3 |
| 196.67 | 4 | 2.49 | | 0 | 0.809 | 2.53 | 31 | 2.49 | | | 4.68 | 0.824 | 2592 | 0.06 | 21.3 |
| 196.83 | | | | | | | | | | 1.007 | 4.68 | 0.825 | 2593 | 0.06 | 21.1 | 0.032 |

| | Time | | | | | | | | | | | | | | | | |
|---|---|---|---|---|---|---|---|---|---|---|---|---|---|---|---|---|---|
| 4 | 197.00 | | | | | | | | | | | | | | | | |
| 4 | 197.17 | 2.475 | 2.44 | 0 | 0.81 | 2.52 | 31 | 2.48 | | | 4.68 | 0.825 | 2596 | 0.06 | 21.1 | 0.028 |
| | 197.33 | | | | | | | | | | 4.68 | 0.826 | 2594 | 0.05 | 21.1 | |
| | 197.50 | | | | | | | | | 1.007 | 4.68 | 0.827 | 2599 | 0.05 | 20.9 | |
| 4 | 197.67 | 2.501 | 2.46 | 0 | 0.808 | 2.52 | 31 | 2.50 | | | 4.68 | 0.827 | 2599 | 0.05 | 20.9 | 0.029 |
| | 197.83 | | | | | | | | | | 4.68 | 0.829 | 2596 | 0.05 | 20.9 | |
| | 198.00 | | | | | | | | | 1.008 | 4.67 | 0.830 | 2590 | 0.05 | 21.4 | |
| 4 | 198.17 | 2.505 | 2.46 | 0 | 0.808 | 2.54 | 31 | 2.51 | | | 4.68 | 0.831 | 2592 | 0.06 | 21.3 | 0.042 |
| | 198.33 | | | | | | | | | | 4.68 | 0.831 | 2580 | 0.05 | 21.3 | |
| | 198.50 | | | | | | | | | 1.008 | 4.68 | 0.832 | 2595 | 0.05 | 21.0 | |
| 4 | 198.67 | 2.521 | 2.4 | 0 | 0.807 | 2.54 | 31 | 2.52 | | | 4.68 | 0.832 | 2597 | 0.05 | 20.9 | 0.03 |
| | 198.83 | | | | | | | | | | 4.68 | 0.832 | 2595 | 0.06 | 20.9 | |
| | 199.00 | | | | | | | | | 1.008 | 4.68 | 0.833 | 2594 | 0.06 | 20.9 | |
| 4 | 199.17 | 2.527 | 2.39 | 0 | 0.806 | 2.55 | 31 | 2.53 | | | 4.68 | 0.834 | 2595 | 0.06 | 20.9 | 0.035 |
| | 199.33 | | | | | | | | | | 4.68 | 0.834 | 2597 | 0.05 | 20.9 | |
| | 199.50 | | | | | | | | | 1.008 | 4.68 | 0.836 | 2600 | 0.06 | 20.8 | |
| 4 | 199.67 | 2.525 | 2.42 | 0 | 0.806 | 2.54 | 31 | 2.53 | | | 4.67 | 0.836 | 2594 | 0.05 | 21.2 | 0.037 |
| | 199.83 | | | | | | | | | | 4.68 | 0.837 | 2598 | 0.06 | 21.1 | |
| | 200.00 | | | | | | | | | 1.008 | 4.68 | 0.836 | 2607 | 0.06 | 20.9 | |
| 4 | 200.17 | 2.528 | 2.48 | 0 | 0.806 | 2.54 | 31 | 2.53 | | | 4.68 | 0.837 | 2606 | 0.06 | 20.8 | 0.038 |
| | 200.33 | | | | | | | | | | 4.68 | 0.837 | 2604 | 0.06 | 20.8 | |
| | 200.50 | | | | | | | | | 1.008 | 4.68 | 0.838 | 2606 | 0.06 | 20.8 | |
| 4 | 200.67 | 2.538 | 2.44 | 0 | 0.805 | 2.55 | 31 | 2.54 | | | 4.68 | 0.839 | 2605 | 0.06 | 20.8 | 0.036 |
| | 200.83 | | | | | | | | | | 4.68 | 0.839 | 2601 | 0.06 | 20.8 | |
| | 201.00 | | | | | | | | | | 4.68 | 0.841 | 2600 | 0.06 | 20.8 | |

FIG. 8VV

| | | | | | | | | | | | | | | | | | | |
|---|---|---|---|---|---|---|---|---|---|---|---|---|---|---|---|---|---|---|
| 4 | 201.17 | 2.539 | 2.4 | 0 | 0.805 | 2.55 | 31 | 2.54 | | | | | | | | 20.8 | 0.06 | 2601 | 0.842 | 4.68 | | 0.035 |
| | 201.33 | | | | | | | | | | | | | | | 20.7 | 0.06 | 2605 | 0.844 | 4.68 | 1.008 | |
| | 201.50 | | | | | | | | | | | | | | | 20.9 | 0.06 | 2594 | 0.846 | 4.67 | | |
| 4 | 201.67 | 2.52 | | 0 | 0.807 | 2.55 | 31 | 2.52 | | | | | | | | 20.9 | 0.06 | 2594 | 0.847 | 4.67 | 1.008 | 0.037 |
| | 201.83 | | | | | | | | | | | | | | | 20.8 | 0.06 | 2603 | 0.847 | 4.68 | | |
| | 202.00 | | | | | | | | | | | | | | | 20.8 | 0.06 | 2603 | 0.847 | 4.68 | | |
| 4 | 202.17 | 2.529 | -3.2 | 0 | 0.806 | 2.55 | 31 | 2.53 | | | | | | | | 20.8 | 0.06 | 2601 | 0.848 | 4.67 | 1.008 | 0.038 |
| | 202.33 | | | | | | | | | | | | | | | 20.8 | 0.06 | 2599 | 0.849 | 4.68 | | |
| | 202.50 | | | | | | | | | | | | | | | 20.7 | 0.06 | 2603 | 0.850 | 4.67 | | |
| 4 | 202.67 | 2.53 | 2.5 | 0 | 0.806 | 2.54 | 31 | 2.53 | | | | | | | | 20.7 | 0.06 | 2604 | 0.851 | 4.68 | 1.008 | 0.038 |
| | 202.83 | | | | | | | | | | | | | | | 20.9 | 0.06 | 2591 | 0.853 | 4.68 | | |
| | 203.00 | | | | | | | | | | | | | | | 20.9 | 0.06 | 2597 | 0.854 | 4.67 | | |
| 4 | 203.17 | 2.56 | 2.46 | 4.M | 0.804 | 2.56 | 31 | 2.54 | | | | | | | | 20.8 | 0.06 | 2573 | 0.855 | 4.67 | 1.008 | 0.041 |
| | 203.33 | | | | | | | | | | | | | | | 20.7 | 0.06 | 2597 | 0.854 | 4.67 | | |
| | 203.50 | | | | | | | | | | | | | | | 20.6 | 0.05 | 2601 | 0.854 | 4.67 | | |
| 4 | 203.67 | 2.54 | 2.46 | 0 | 0.805 | 2.55 | 30 | 2.54 | | | | | | | | 20.6 | 0.05 | 2600 | 0.854 | 4.67 | 1.008 | 0.042 |
| | 203.83 | | | | | | | | | | | | | | | 20.6 | 0.05 | 2599 | 0.855 | 4.68 | | |
| | 204.00 | | | | | | | | | | | | | | | 20.6 | 0.05 | 2599 | 0.856 | 4.67 | | |
| 4 | 204.17 | 2.57 | 2.54 | 4.M | 0.803 | 2.57 | 31 | 2.55 | | | | | | | | 20.6 | 0.05 | 2601 | 0.857 | 4.67 | 1.008 | 0.046 |
| | 204.33 | | | | | | | | | | | | | | | 20.7 | 0.06 | 2602 | 0.859 | 4.67 | | |
| | 204.50 | | | | | | | | | | | | | | | 20.4 | 0.05 | 2599 | 0.861 | 4.68 | | |
| 4 | 204.67 | 2.57 | 2.45 | 4.M | 0.803 | 2.57 | 31 | 2.54 | | | | | | | | 20.6 | 0.05 | 2595 | 0.861 | 4.67 | 1.008 | 0.04 |
| | 204.83 | | | | | | | | | | | | | | | 20.6 | 0.06 | 2593 | 0.862 | 4.67 | | |
| | 205.00 | | | | | | | | | | | | | | | 20.6 | 0.05 | 2593 | 0.862 | 4.67 | | |
| 4 | 205.17 | 2.561 | 2.49 | 0 | 0.803 | 2.58 | 31 | 2.56 | | | | | | | | 20.6 | 0.05 | 2594 | 0.863 | 4.67 | 1.008 | 0.049 |

FIG. 8WW

| 4 | 205.33 |       |      |     |       |      |    |      | | |       |      |       |      |      |      |       |
|---|--------|-------|------|-----|-------|------|----|------|---|---|-------|------|-------|------|------|------|-------|
|   | 205.50 |       |      |     |       |      |    |      | | |       |      |       |      |      |      |       |
|   | 205.67 | 2.571 | 2.64 | 0   | 0.803 | 2.6  | 31 | 2.57 | | |       | 4.67 | 0.863 | 2593 | 0.05 | 20.6 |       |
|   | 205.83 |       |      |     |       |      |    |      | | |       | 4.67 | 0.863 | 2594 | 0.05 | 20.6 | 0.044 |
|   | 206.00 |       |      |     |       |      |    |      | | | 1.008 | 4.67 | 0.864 | 2591 | 0.05 | 20.6 |       |
| 4 | 206.17 | 2.569 | 2.51 | 0   | 0.803 | 2.6  | 31 | 2.57 | | |       | 4.67 | 0.865 | 2593 | 0.05 | 20.6 |       |
|   | 206.33 |       |      |     |       |      |    |      | | |       | 4.67 | 0.867 | 2594 | 0.05 | 20.6 | 0.047 |
|   | 206.50 |       |      |     |       |      |    |      | | |       | 4.68 | 0.869 | 2593 | 0.06 | 20.3 |       |
| 4 | 206.67 | 2.565 | 2.47 | 0   | 0.803 | 2.59 | 31 | 2.57 | | | 1.008 | 4.67 | 0.870 | 2583 | 0.05 | 20.6 |       |
|   | 206.83 |       |      |     |       |      |    |      | | |       | 4.67 | 0.870 | 2588 | 0.05 | 20.5 | 0.04  |
|   | 207.00 |       |      |     |       |      |    |      | | |       | 4.67 | 0.870 | 2583 | 0.05 | 20.6 |       |
| 4 | 207.17 | 2.563 | 2.51 | 0   | 0.803 | 2.6  | 31 | 2.56 | | |       | 4.67 | 0.871 | 2588 | 0.05 | 20.6 |       |
|   | 207.33 |       |      |     |       |      |    |      | | | 1.008 | 4.67 | 0.871 | 2589 | 0.05 | 20.6 | 0.041 |
|   | 207.50 |       |      |     |       |      |    |      | | |       | 4.67 | 0.872 | 2591 | 0.05 | 20.6 |       |
| 4 | 207.67 | 2.58  | 2.47 | 4.M | 0.802 | 2.58 | 31 | 2.56 | | |       | 4.67 | 0.872 | 2591 | 0.05 | 20.6 |       |
|   | 207.83 |       |      |     |       |      |    |      | | |       | 4.67 | 0.873 | 2592 | 0.05 | 20.6 | 0.042 |
|   | 208.00 |       |      |     |       |      |    |      | | | 1.008 | 4.67 | 0.874 | 2589 | 0.05 | 20.6 |       |
| 4 | 208.17 | 2.58  | 2.47 | 4.M | 0.802 | 2.58 | 31 | 2.56 | | |       | 4.68 | 0.876 | 2586 | 0.05 | 20.1 |       |
|   | 208.33 |       |      |     |       |      |    |      | | |       | 4.67 | 0.877 | 2592 | 0.05 | 20.4 | 0.044 |
|   | 208.50 |       |      |     |       |      |    |      | | |       | 4.67 | 0.880 | 2583 | 0.05 | 20.6 |       |
| 4 | 208.67 | 2.565 | 2.49 | 0   | 0.803 | 2.59 | 31 | 2.57 | | | 1.008 | 4.67 | 0.880 | 2589 | 0.05 | 20.5 |       |
|   | 208.83 |       |      |     |       |      |    |      | | |       | 4.67 | 0.880 | 2579 | 0.05 | 20.6 | 0.043 |
|   | 209.00 |       |      |     |       |      |    |      | | |       | 4.67 | 0.881 | 2582 | 0.05 | 20.6 |       |
| 4 | 209.17 | 2.569 | 2.42 | 0   | 0.803 | 2.6  | 31 | 2.57 | | |       | 4.67 | 0.881 | 2583 | 0.05 | 20.6 |       |
|   | 209.33 |       |      |     |       |      |    |      | | | 1.008 | 4.67 | 0.881 | 2588 | 0.05 | 20.6 | 0.047 |
|   |        |       |      |     |       |      |    |      | | |       | 4.67 | 0.882 | 2590 | 0.05 | 20.6 |       |

FIG. 8XX

| | | | | | | | | | | | | | | | | |
|---|---|---|---|---|---|---|---|---|---|---|---|---|---|---|---|---|
| | 209.50 | | | | | | | | | | | | | | | |
| 4 | 209.67 | 2.562 | 2.49 | 0 | 0.803 | 2.58 | 30 | 2.56 | | | 4.67 | 0.883 | 2590 | 0.05 | 20.6 | 0.044 |
| | 209.83 | | | | | | | | | 1.008 | 4.67 | 0.884 | 2589 | 0.05 | 20.6 | |
| | 210.00 | | | | | | | | | | 4.67 | 0.885 | 2589 | 0.05 | 20.6 | |
| 4 | 210.17 | 2.56 | 2.48 | 4.M | 0.804 | 2.56 | 31 | 2.55 | | | 4.67 | 0.887 | 2590 | 0.05 | 20.6 | 0.033 |
| | 210.33 | | | | | | | | | 1.008 | 4.67 | 0.889 | 2591 | 0.05 | 20.6 | |
| | 210.50 | | | | | | | | | | 4.67 | 0.892 | 2584 | 0.06 | 20.7 | |
| 4 | 210.67 | 2.56 | 2.48 | 4.M | 0.804 | 2.56 | 31 | 2.53 | | | 4.67 | 0.892 | 2574 | 0.05 | 20.8 | 0.036 |
| | 210.83 | | | | | | | | | 1.008 | 4.67 | 0.894 | 2575 | 0.06 | 20.8 | |
| | 211.00 | | | | | | | | | | 4.67 | 0.895 | 2598 | 0.06 | 20.7 | |
| 4 | 211.17 | 2.518 | 2.43 | 0 | 0.807 | 2.52 | 31 | 2.52 | | | 4.67 | 0.896 | 2590 | 0.06 | 20.7 | 0.03 |
| | 211.33 | | | | | | | | | 1.008 | 4.67 | 0.897 | 2592 | 0.06 | 20.7 | |
| | 211.50 | | | | | | | | | | 4.67 | 0.898 | 2587 | 0.06 | 20.7 | |
| 4 | 211.67 | 2.506 | 2.44 | 0 | 0.808 | 2.51 | 31 | 2.51 | | | 4.67 | 0.900 | 2588 | 0.06 | 20.7 | 0.024 |
| | 211.83 | | | | | | | | | 1.008 | 4.67 | 0.901 | 2589 | 0.06 | 20.8 | |
| | 212.00 | | | | | | | | | | 4.67 | 0.903 | 2585 | 0.06 | 20.8 | |
| 4 | 212.17 | 2.482 | 2.43 | 0 | 0.81 | 2.52 | 31 | 2.48 | | | 4.67 | 0.905 | 2586 | 0.06 | 20.8 | 0.044 |
| | 212.33 | | | | | | | | | 1.008 | 4.67 | 0.908 | 2586 | 0.06 | 20.8 | |
| | 212.50 | | | | | | | | | | 4.67 | 0.911 | 2587 | 0.06 | 21.1 | |
| 4 | 212.67 | 2.468 | 2.47 | 0 | 0.811 | 2.5 | 31 | 2.47 | | | 4.67 | 0.911 | 2578 | 0.06 | 21.3 | 0.054 |
| | 212.83 | | | | | | | | | 1.007 | 4.67 | 0.913 | 2581 | 0.05 | 21.2 | |
| | 213.00 | | | | | | | | | | 4.67 | 0.914 | 2593 | 0.06 | 20.9 | |
| 4 | 213.17 | 2.458 | | 0 | 0.811 | 2.49 | 31 | 2.46 | | | 4.67 | 0.915 | 2595 | 0.05 | 20.9 | 0.043 |
| | 213.33 | | | | | | | | | 1.007 | 4.67 | 0.916 | 2594 | 0.05 | 20.9 | |
| | 213.50 | | | | | | | | | | 4.68 | 0.917 | 2586 | 0.06 | 20.9 | |
| | | | | | | | | | | | 4.68 | 0.919 | 2594 | 0.06 | 20.9 | |

FIG. 8YY

| 4 | 213.67 | 2.454 | 2.43 | 0 | 0.812 | 2.5 | 31 | 2.45 | | | 1.007 | 4.68 | 0.921 | 2590 | 0.05 | 20.9 | 0.027 |
|---|---|---|---|---|---|---|---|---|---|---|---|---|---|---|---|---|---|
| | 213.83 | | | | | | | | | | | 4.68 | 0.923 | 2594 | 0.06 | 20.9 | |
| | 214.00 | | | | | | | | | | | 4.67 | 0.926 | 2550 | 0.05 | 21.8 | 0.054 |
| 4 | 214.17 | 2.459 | | 0 | 0.811 | 2.48 | 31 | 2.46 | | | 1.007 | 4.67 | 0.927 | 2555 | 0.05 | 21.8 | |
| | 214.33 | | | | | | | | | | | 4.67 | 0.929 | 2573 | 0.06 | 21.3 | |
| | 214.50 | | | | | | | | | | | 4.68 | 0.930 | 2584 | 0.06 | 21.1 | 0.041 |
| 4 | 214.67 | 2.445 | | 0 | 0.812 | 2.47 | 31 | 2.45 | | | 1.007 | 4.68 | 0.930 | 2589 | 0.06 | 21.0 | |
| | 214.83 | | | | | | | | | | | 4.68 | 0.932 | 2590 | 0.06 | 21.0 | |
| | 215.00 | | | | | | | | | | | 4.68 | 0.933 | 2589 | 0.06 | 20.9 | 0.032 |
| 4 | 215.17 | 2.439 | 2.38 | 0 | 0.813 | 2.46 | 31 | 2.44 | | | 1.007 | 4.68 | 0.935 | 2590 | 0.05 | 21.0 | |
| | 215.33 | | | | | | | | | | | 4.68 | 0.937 | 2592 | 0.05 | 20.9 | |
| | 215.50 | | | | | | | | | | | 4.68 | 0.938 | 2573 | 0.06 | 21.3 | 0.092 |
| 4 | 215.67 | 2.441 | 2.39 | 0 | 0.813 | 2.48 | 31 | 2.44 | | | 1.007 | 4.67 | 0.941 | 2572 | 0.05 | 22.3 | |
| | 215.83 | | | | | | | | | | | 4.67 | 0.942 | 2569 | 0.05 | 21.8 | |
| | 216.00 | | | | | | | | | | | 4.68 | 0.942 | 2582 | 0.05 | 21.4 | 0.041 |
| 4 | 216.17 | 2.452 | 2.48 | 0 | 0.812 | 2.49 | 31 | 2.45 | | | 1.007 | 4.68 | 0.943 | 2577 | 0.05 | 21.4 | |
| | 216.33 | | | | | | | | | | | 4.68 | 0.944 | 2595 | 0.06 | 21.1 | |
| | 216.50 | | | | | | | | | | | 4.68 | 0.945 | 2591 | 0.06 | 21.1 | 0.039 |
| 4 | 216.67 | 2.456 | 2.51 | 0 | 0.812 | 2.52 | 31 | 2.46 | | | 1.007 | 4.68 | 0.946 | 2590 | 0.06 | 21.1 | |
| | 216.83 | | | | | | | | | | | 4.68 | 0.947 | 2593 | 0.06 | 21.0 | |
| | 217.00 | | | | | | | | | | | 4.68 | 0.949 | 2586 | 0.06 | 21.1 | 0.04 |
| 4 | 217.17 | 2.434 | 2.4 | 0 | 0.813 | 2.48 | 31 | 2.43 | | | 1.007 | 4.68 | 0.950 | 2587 | 0.06 | 21.0 | |
| | 217.33 | | | | | | | | | | | 4.68 | 0.951 | 2589 | 0.06 | 21.0 | |
| | 217.50 | | | | | | | | | | | 4.68 | 0.953 | 2588 | 0.06 | 21.0 | |
| 4 | 217.67 | 2.434 | 2.36 | 0 | 0.813 | 2.47 | 31 | 2.43 | | | 1.007 | 4.67 | 0.955 | 2558 | 0.06 | 22.3 | 0.103 |

| | Time | | | | | | | | | | | | | | | | |
|---|---|---|---|---|---|---|---|---|---|---|---|---|---|---|---|---|---|
| | 217.83 | | | | | | | | | | | | | | | | |
| | 218.00 | | | | | | | | | | | 4.67 | 0.956 | 2565 | 0.06 | 21.6 | |
| 4 | 218.17 | 2.429 | 2.36 | 0 | 0.814 | 2.46 | 31 | 2.43 | | | 1.007 | 4.68 | 0.956 | 2571 | 0.06 | 21.6 | 0.035 |
| | 218.33 | | | | | | | | | | | 4.68 | 0.957 | 2581 | 0.06 | 21.4 | |
| | 218.50 | | | | | | | | | | | 4.68 | 0.957 | 2593 | 0.06 | 21.1 | |
| 4 | 218.67 | 2.436 | 2.35 | 0 | 0.813 | 2.46 | 31 | 2.44 | | | 1.007 | 4.68 | 0.958 | 2591 | 0.06 | 21.1 | 0.038 |
| | 218.83 | | | | | | | | | | | 4.68 | 0.958 | 2587 | 0.06 | 21.1 | |
| | 219.00 | | | | | | | | | | | 4.68 | 0.959 | 2594 | 0.06 | 21.0 | |
| 4 | 219.17 | 2.436 | 2.36 | 0 | 0.813 | 2.46 | 30 | 2.44 | | | 1.007 | 4.68 | 0.960 | 2588 | 0.06 | 21.0 | 0.03 |
| | 219.33 | | | | | | | | | | | 4.68 | 0.960 | 2587 | 0.06 | 21.0 | |
| | 219.50 | | | | | | | | | | | 4.67 | 0.961 | 2587 | 0.06 | 21.0 | |
| 4 | 219.67 | 2.443 | 2.39 | 0 | 0.813 | 2.47 | 31 | 2.44 | | | 1.007 | 4.68 | 0.962 | 2588 | 0.05 | 21.0 | 0.034 |
| | 219.83 | | | | | | | | | | | 4.68 | 0.963 | 2580 | 0.05 | 21.6 | |
| | 220.00 | | | | | | | | | | | 4.68 | 0.963 | 2572 | 0.05 | 21.6 | |
| 4 | 220.17 | 2.445 | 2.37 | 0 | 0.812 | 2.46 | 31 | 2.45 | | | 1.007 | 4.67 | 0.963 | 2588 | 0.06 | 21.3 | 0.031 |
| | 220.33 | | | | | | | | | | | 4.68 | 0.964 | 2588 | 0.05 | 21.3 | |
| | 220.50 | | | | | | | | | | | 4.68 | 0.964 | 2597 | 0.05 | 21.1 | |
| 4 | 220.67 | 2.445 | 2.36 | 0 | 0.812 | 2.46 | 31 | 2.45 | | | 1.007 | 4.68 | 0.965 | 2599 | 0.05 | 21.0 | 0.033 |
| | 220.83 | | | | | | | | | | | 4.68 | 0.965 | 2572 | 0.05 | 21.5 | |
| | 221.00 | | | | | | | | | | | 4.67 | 0.966 | 2569 | 0.05 | 21.3 | |
| 4 | 221.17 | 2.453 | 2.35 | 0 | 0.812 | 2.48 | 31 | 2.45 | | | 1.007 | 4.68 | 0.966 | 2583 | 0.05 | 21.1 | 0.038 |
| | 221.33 | | | | | | | | | | | 4.68 | 0.967 | 2573 | 0.05 | 21.3 | |
| | 221.50 | | | | | | | | | | | 4.68 | 0.968 | 2589 | 0.05 | 21.1 | |
| 4 | 221.67 | 2.469 | 2.34 | 0 | 0.811 | 2.48 | 31 | 2.47 | | | 1.007 | 4.68 | 0.969 | 2580 | 0.05 | 21.3 | 0.035 |
| | 221.83 | | | | | | | | | | | 4.68 | 0.970 | 2590 | 0.05 | 21.1 | |
| | | | | | | | | | | | | | | 2588 | 0.05 | 21.0 | |

FIG. 8BBB

| | | | | | | | | | | | | | | | | | |
|---|---|---|---|---|---|---|---|---|---|---|---|---|---|---|---|---|---|
| 4 | 222.00 | | | | | | | | | | | | | | | | |
| | 222.17 | 2.47 | 2.4 | 0 | 0.81 | 2.49 | 31 | 2.47 | | 1.007 | 4.68 | 0.971 | 2592 | 0.05 | 20.9 | 0.037 |
| | 222.33 | | | | | | | | | | 4.68 | 0.971 | 2589 | 0.05 | 20.9 | |
| | 222.50 | | | | | | | | | | 4.68 | 0.972 | 2591 | 0.06 | 20.9 | |
| 4 | 222.67 | 2.467 | 2.39 | 0 | 0.811 | 2.49 | 31 | 2.47 | | 1.007 | 4.68 | 0.973 | 2593 | 0.06 | 20.9 | 0.032 |
| | 222.83 | | | | | | | | | | 4.67 | 0.975 | 2582 | 0.05 | 21.4 | |
| | 223.00 | | | | | | | | | | 4.68 | 0.975 | 2572 | 0.06 | 21.3 | |
| 4 | 223.17 | 2.479 | 2.51 | 0 | 0.81 | 2.49 | 31 | 2.48 | | 1.008 | 4.68 | 0.975 | 2575 | 0.05 | 21.2 | 0.037 |
| | 223.33 | | | | | | | | | | 4.68 | 0.975 | 2575 | 0.06 | 21.2 | |
| | 223.50 | | | | | | | | | | 4.68 | 0.975 | 2589 | 0.06 | 20.9 | |
| 4 | 223.67 | 2.486 | 2.57 | 0 | 0.809 | 2.5 | 31 | 2.49 | | 1.008 | 4.68 | 0.975 | 2594 | 0.06 | 20.9 | 0.039 |
| | 223.85 | | | | | | | | | | 4.68 | 0.975 | 2589 | 0.06 | 20.9 | |
| | 224.02 | | | | | | | | | | 4.68 | 0.976 | 2595 | 0.06 | 20.8 | |
| 4 | 224.18 | 2.484 | 2.44 | 0 | 0.809 | 2.5 | 31 | 2.48 | | 1.008 | 4.68 | 0.976 | 2591 | 0.06 | 20.8 | 0.038 |
| | 224.35 | | | | | | | | | | 4.68 | 0.977 | 2583 | 0.06 | 20.9 | |
| | 224.52 | | | | | | | | | | 4.68 | 0.977 | 2592 | 0.06 | 20.8 | |
| 4 | 224.68 | 2.494 | 2.37 | 0 | 0.809 | 2.52 | 31 | 2.49 | | 1.008 | 4.68 | 0.979 | 2578 | 0.06 | 20.8 | 0.043 |
| | 224.85 | | | | | | | | | | 4.68 | 0.980 | 2583 | 0.06 | 20.8 | |
| | 225.02 | | | | | | | | | | 4.67 | 0.981 | 2584 | 0.05 | 20.9 | |
| 4 | 225.18 | 2.493 | 2.38 | 0 | 0.809 | 2.51 | 30 | 2.49 | | 1.008 | 4.68 | 0.983 | 2581 | 0.05 | 20.8 | 0.039 |
| | 225.35 | | | | | | | | | | 4.68 | 0.983 | 2585 | 0.06 | 20.8 | |
| | 225.52 | | | | | | | | | | 4.68 | 0.983 | 2581 | 0.05 | 20.8 | |
| 4 | 225.68 | 2.493 | | 0 | 0.809 | 2.51 | 31 | 2.49 | | 1.008 | 4.68 | 0.984 | 2588 | 0.06 | 20.8 | 0.04 |
| | 225.85 | | | | | | | | | | 4.67 | 0.985 | 2588 | 0.05 | 20.8 | |
| | 226.02 | | | | | | | | | | 4.68 | 0.986 | 2593 | 0.05 | 20.8 | |

FIG. 8CCC

| | | | | | | | | | | | | | | | | | | | |
|---|---|---|---|---|---|---|---|---|---|---|---|---|---|---|---|---|---|---|---|
| 4 | 226.18 | 2.492 | 2.44 | 0 | 0.809 | 2.52 | 31 | 2.49 | | | 1.008 | 4.68 | 0.986 | 2596 | 0.05 | 20.8 | 0.045 |
| | 226.35 | 2.488 | | | | | | | | | | 4.67 | 0.987 | 2596 | 0.05 | 20.8 | |
| | 226.52 | | | | | | | | | | | 4.68 | 0.989 | 2596 | 0.05 | 20.8 | |
| 4 | 226.68 | 2.488 | 2.39 | 0 | 0.809 | 2.51 | 31 | 2.49 | | | 1.008 | 4.67 | 0.989 | 2592 | 0.05 | 20.8 | 0.044 |
| | 226.85 | | | | | | | | | | | 4.67 | 0.990 | 2591 | 0.05 | 20.8 | |
| | 227.02 | | | | | | | | | | | 4.67 | 0.991 | 2592 | 0.05 | 20.8 | |
| 4 | 227.18 | 2.477 | 2.42 | 0 | 0.81 | 2.5 | 31 | 2.48 | | | 1.008 | 4.68 | 0.994 | 2596 | 0.05 | 20.4 | 0.043 |
| | 227.35 | | | | | | | | | | | 4.68 | 0.994 | 2600 | 0.06 | 20.7 | |
| | 227.52 | | | | | | | | | | | 4.68 | 0.994 | 2587 | 0.05 | 20.6 | |
| 4 | 227.68 | 2.485 | 2.39 | 0 | 0.809 | 2.52 | 31 | 2.49 | | | 1.008 | 4.67 | 0.994 | 2591 | 0.06 | 20.7 | 0.047 |
| | 227.85 | | | | | | | | | | | 4.67 | 0.995 | 2599 | 0.05 | 20.6 | |
| | 228.02 | | | | | | | | | | | 4.67 | 0.995 | 2601 | 0.06 | 20.7 | |
| 4 | 228.18 | 2.486 | 2.38 | 0 | 0.809 | 2.51 | 31 | 2.49 | | | 1.008 | 4.67 | 0.996 | 2603 | 0.06 | 20.7 | 0.046 |
| | 228.35 | | | | | | | | | | | 4.67 | 0.997 | 2592 | 0.06 | 20.7 | |
| | 228.52 | | | | | | | | | | | 4.67 | 0.998 | 2599 | 0.06 | 20.7 | |
| 4 | 228.68 | 2.488 | 2.43 | 0 | 0.809 | 2.51 | 31 | 2.49 | | | 1.008 | 4.67 | 0.999 | 2603 | 0.05 | 20.6 | 0.04 |
| | 228.85 | | | | | | | | | | | 4.67 | 1.002 | 2597 | 0.05 | 20.6 | |
| | 229.02 | | | | | | | | | | | 4.67 | 1.002 | 2593 | 0.06 | 20.7 | |
| 4 | 229.18 | 2.493 | 2.45 | 0 | 0.809 | 2.52 | 31 | 2.49 | | | 1.008 | 4.67 | 1.002 | 2595 | 0.05 | 20.6 | 0.053 |
| | 229.35 | | | | | | | | | | | 4.67 | 1.003 | 2597 | 0.05 | 20.6 | |
| | 229.52 | | | | | | | | | | | 4.67 | 1.003 | 2597 | 0.05 | 20.6 | |
| 4 | 229.68 | 2.511 | 2.44 | 0 | 0.807 | 2.53 | 31 | 2.51 | | | 1.008 | 4.67 | 1.004 | 2601 | 0.05 | 20.6 | 0.05 |
| | 229.85 | | | | | | | | | | | 4.67 | 1.004 | 2599 | 0.06 | 20.7 | |
| | 230.02 | | | | | | | | | | | 4.67 | 1.004 | 2604 | 0.05 | 20.6 | |
| 4 | 230.18 | 2.506 | 2.44 | 0 | 0.808 | 2.53 | 31 | 2.51 | | | 1.008 | 4.67 | 1.005 | 2601 | 0.06 | 20.7 | 0.047 |

FIG. 8DDD

| | | | | | | | | | | | | | | | |
|---|---|---|---|---|---|---|---|---|---|---|---|---|---|---|---|
| 230.35 | | | | | | | | | | | | | | | |
| 230.52 | 4 | 2.507 | 2.46 | | | | | | | | | | | | |
| 230.68 | | | | 0 | 0.808 | 2.53 | 31 | 2.51 | 1.008 | 4.67 | 1.007 | 2605 | 0.06 | 20.7 | 0.047 |
| 230.85 | | | | | | | | | | 4.67 | 1.009 | 2609 | 0.05 | 20.6 | |
| 231.02 | | | | | | | | | | 4.67 | 1.010 | 2606 | 0.05 | 20.7 | |
| 231.18 | 4 | 2.515 | 2.48 | 0 | 0.807 | 2.53 | 30 | 2.52 | 1.008 | 4.67 | 1.011 | 2606 | 0.05 | 20.7 | 0.054 |
| 231.35 | | | | | | | | | | 4.67 | 1.012 | 2591 | 0.05 | 20.6 | |
| 231.52 | | | | | | | | | | 4.67 | 1.013 | 2597 | 0.05 | 20.6 | |
| 231.68 | 4 | 2.507 | 2.48 | 0 | 0.808 | 2.53 | 31 | 2.51 | 1.008 | 4.67 | 1.013 | 2592 | 0.06 | 20.6 | 0.044 |
| 231.85 | | | | | | | | | | 4.67 | 1.014 | 2598 | 0.06 | 20.6 | |
| 232.02 | | | | | | | | | | 4.67 | 1.014 | 2597 | 0.05 | 20.6 | |
| 232.18 | 4 | 2.498 | 2.45 | 0 | 0.808 | 2.53 | 31 | 2.50 | 1.008 | 4.67 | 1.015 | 2604 | 0.05 | 20.6 | 0.047 |
| 232.35 | | | | | | | | | | 4.67 | 1.015 | 2605 | 0.05 | 20.6 | |
| 232.52 | | | | | | | | | | 4.67 | 1.016 | 2604 | 0.05 | 20.6 | |
| 232.68 | 4 | 2.504 | 2.39 | 0 | 0.808 | 2.54 | 31 | 2.50 | 1.008 | 4.67 | 1.017 | 2606 | 0.05 | 20.6 | 0.052 |
| 232.85 | | | | | | | | | | 4.67 | 1.018 | 2604 | 0.06 | 20.4 | |
| 233.02 | | | | | | | | | | 4.67 | 1.020 | 2610 | 0.06 | 20.4 | |
| 233.18 | 4 | 2.489 | 2.44 | 0 | 0.809 | 2.51 | 31 | 2.49 | 1.008 | 4.67 | 1.020 | 2606 | 0.06 | 20.3 | 0.051 |
| 233.35 | | | | | | | | | | 4.67 | 1.020 | 2580 | 0.05 | 20.4 | |
| 233.52 | | | | | | | | | | 4.67 | 1.020 | 2598 | 0.05 | 20.6 | |
| 233.68 | 4 | 2.509 | 2.45 | 0 | 0.807 | 2.54 | 31 | 2.51 | 1.008 | 4.67 | 1.021 | 2589 | 0.05 | 20.6 | 0.053 |
| 233.85 | | | | | | | | | | 4.67 | 1.021 | 2607 | 0.05 | 20.6 | |
| 234.02 | | | | | | | | | | 4.67 | 1.022 | 2605 | 0.05 | 20.6 | |
| 234.18 | 4 | 2.499 | 2.38 | 0 | 0.808 | 2.52 | 31 | 2.50 | 1.008 | 4.67 | 1.024 | 2599 | 0.05 | 20.6 | 0.044 |
| 234.35 | | | | | | | | | | 4.67 | 1.025 | 2600 | 0.05 | 20.6 | |
| | | | | | | | | | | | | 2598 | | | |

FIG. 8EEE

| | | | | | | | | | | | | | | | | | |
|---|---|---|---|---|---|---|---|---|---|---|---|---|---|---|---|---|---|
| | 234.52 | | | | | | | | | | | | | | | | |
| 4 | 234.68 | 2.482 | 2.41 | 0 | 0.81 | 2.52 | 31 | 2.48 | | 1.008 | 4.67 | 1.027 | 2602 | 0.05 | 20.6 | 0.033 |
| | 234.85 | | | | | | | | | | 4.67 | 1.029 | 2604 | 0.05 | 20.6 | |
| | 235.02 | | | | | | | | | | 4.67 | 1.031 | 2602 | 0.05 | 20.6 | |
| 4 | 235.18 | 2.474 | 2.4 | 0 | 0.81 | 2.51 | 31 | 2.47 | | 1.008 | 4.67 | 1.031 | 2596 | 0.05 | 20.6 | 0.042 |
| | 235.35 | | | | | | | | | | 4.67 | 1.032 | 2583 | 0.06 | 20.7 | |
| | 235.52 | | | | | | | | | | 4.67 | 1.033 | 2583 | 0.05 | 20.6 | |
| 4 | 235.68 | 2.469 | 2.37 | 0 | 0.811 | 2.48 | 31 | 2.47 | | 1.008 | 4.67 | 1.034 | 2585 | 0.05 | 20.6 | 0.031 |
| | 235.85 | | | | | | | | | | 4.67 | 1.035 | 2585 | 0.05 | 20.6 | |
| | 236.02 | | | | | | | | | | 4.67 | 1.037 | 2589 | 0.05 | 20.7 | |
| 4 | 236.18 | 2.457 | 2.47 | 0 | 0.811 | 2.46 | 31 | 2.46 | | 1.008 | 4.67 | 1.038 | 2589 | 0.05 | 20.7 | 0.028 |
| | 236.35 | | | | | | | | | | 4.67 | 1.039 | 2591 | 0.06 | 20.7 | |
| | 236.52 | | | | | | | | | | 4.67 | 1.041 | 2594 | 0.06 | 20.7 | |
| 4 | 236.68 | 2.445 | 2.42 | 0 | 0.812 | 2.45 | 31 | 2.45 | | 1.007 | 4.67 | 1.042 | 2594 | 0.06 | 20.8 | 0.036 |
| | 236.85 | | | | | | | | | | 4.67 | 1.044 | 2593 | 0.06 | 20.8 | |
| | 237.02 | | | | | | | | | | 4.67 | 1.045 | 2595 | 0.06 | 21.1 | |
| 4 | 237.18 | 2.43 | 2.42 | 0 | 0.814 | 2.46 | 31 | 2.43 | | 1.007 | 4.67 | 1.049 | 2578 | 0.06 | 21.1 | 0.025 |
| | 237.35 | | | | | | | | | | 4.67 | 1.050 | 2580 | 0.06 | 21.1 | |
| | 237.52 | | | | | | | | | | 4.67 | 1.051 | 2580 | 0.06 | 20.9 | |
| 4 | 237.68 | 2.43 | 2.35 | 0 | 0.814 | 2.44 | 31 | 2.43 | | 1.007 | 4.67 | 1.051 | 2585 | 0.06 | 20.8 | 0.027 |
| | 237.85 | | | | | | | | | | 4.67 | 1.053 | 2593 | 0.06 | 20.8 | |
| | 238.02 | | | | | | | | | | 4.67 | 1.054 | 2600 | 0.06 | 20.8 | |
| 4 | 238.18 | 2.432 | 2.32 | 0 | 0.813 | 2.44 | 31 | 2.43 | | 1.007 | 4.67 | 1.054 | 2598 | 0.06 | 20.8 | 0.031 |
| | 238.35 | | | | | | | | | | 4.67 | 1.055 | 2600 | 0.05 | 20.8 | |
| | 238.52 | | | | | | | | | | 4.67 | 1.057 | 2601 | 0.06 | 20.8 | |

FIG. 8FFF

| | | | | | | | | | | | | | | | | |
|---|---|---|---|---|---|---|---|---|---|---|---|---|---|---|---|---|
| 4 | 238.68 | 2.412 | 2.35 | 0 | 0.815 | 2.44 | 31 | 2.41 | | 1.007 | 4.67 | 1.058 | 2599 | 0.06 | 20.8 | 0.035 |
| | 238.85 | | | | | | | | | | 4.68 | 1.059 | 2603 | 0.05 | 20.8 | |
| | 239.02 | | | | | | | | | | 4.67 | 1.060 | 2601 | 0.06 | 20.8 | |
| 4 | 239.18 | 2.428 | 2.35 | 0 | 0.814 | 2.43 | 31 | 2.43 | | 1.007 | 4.67 | 1.109 | 2609 | 0.05 | 21.8 | 0.033 |
| | 239.35 | | | | | | | | | | 4.66 | 1.142 | 2605 | 0.05 | 22.6 | |
| | 239.52 | | | | | | | | | | 4.65 | 1.166 | 2608 | 0.05 | 23.0 | |
| 4 | 239.68 | 2.433 | 2.33 | 0 | 0.813 | 2.46 | 31 | 2.43 | | 1.007 | 4.66 | 1.171 | 2612 | 0.05 | 22.6 | 0.039 |
| | 239.85 | | | | | | | | | | 4.65 | 1.192 | 2610 | 0.05 | 23.4 | |
| | 240.02 | | | | | | | | | | 4.65 | 1.211 | 2607 | 0.05 | 23.9 | |
| 4 | 240.18 | 2.421 | 2.33 | 0 | 0.814 | 2.45 | 31 | 2.42 | | 1.007 | 4.65 | 1.209 | 2607 | 0.05 | 23.2 | 0.039 |
| | 240.35 | | | | | | | | | | 4.64 | 1.229 | 2610 | 0.05 | 23.9 | |
| | 240.52 | | | | | | | | | | 4.64 | 1.244 | 2613 | 0.05 | 24.3 | |
| 4 | 240.68 | 2.416 | 2.36 | 0 | 0.815 | 2.44 | 31 | 2.42 | | 1.007 | 4.65 | 1.225 | 2612 | 0.05 | 23.4 | 0.041 |
| | 240.85 | | | | | | | | | | 4.64 | 1.246 | 2616 | 0.05 | 24.1 | |
| | 241.02 | | | | | | | | | | 4.64 | 1.260 | 2609 | 0.05 | 24.4 | |
| 4 | 241.18 | 2.411 | 2.32 | 0 | 0.815 | 2.43 | 31 | 2.41 | | 1.007 | 4.65 | 1.254 | 2616 | 0.05 | 23.3 | 0.042 |
| | 241.35 | | | | | | | | | | 4.64 | 1.267 | 2615 | 0.05 | 24.2 | |
| | 241.52 | | | | | | | | | | 4.64 | 1.274 | 2612 | 0.05 | 24.4 | |
| 4 | 241.68 | 2.407 | 2.31 | 0 | 0.815 | 2.44 | 31 | 2.41 | | 1.007 | 4.65 | 1.267 | 2612 | 0.05 | 23.3 | 0.041 |
| | 241.85 | | | | | | | | | | 4.64 | 1.272 | 2615 | 0.05 | 24.1 | |
| | 242.02 | | | | | | | | | | 4.64 | 1.280 | 2610 | 0.05 | 24.4 | |
| 4 | 242.18 | 2.405 | 2.33 | 0 | 0.815 | 2.45 | 31 | 2.41 | | 1.007 | 4.65 | 1.271 | 2611 | 0.05 | 23.2 | 0.046 |
| | 242.35 | | | | | | | | | | 4.64 | 1.278 | 2615 | 0.05 | 24.0 | |
| | 242.52 | | | | | | | | | | 4.64 | 1.278 | 2610 | 0.05 | 24.3 | |
| 4 | 242.68 | 2.405 | 2.35 | 0 | 0.815 | 2.43 | 31 | 2.41 | | 1.007 | 4.65 | 1.272 | 2610 | 0.05 | 23.0 | 0.046 |

| | | | | | | | | | | | | | | | | | |
|---|---|---|---|---|---|---|---|---|---|---|---|---|---|---|---|---|---|
| 242.85 | | | | | | | | | | | | 4.65 | 1.275 | 2615 | 0.05 | 23.8 | |
| 243.02 | | | | | | | | | | | | 4.64 | 1.275 | 2609 | 0.05 | 24.1 | |
| 243.18 | 4 | 2.405 | 2.31 | 0 | 0.815 | 2.43 | 31 | 2.41 | | | 1.007 | 4.66 | 1.266 | 2607 | 0.05 | 22.8 | 0.048 |
| 243.35 | | | | | | | | | | | | 4.65 | 1.268 | 2614 | 0.05 | 23.6 | |
| 243.52 | | | | | | | | | | | | 4.65 | 1.267 | 2609 | 0.05 | 23.8 | |
| 243.68 | 4 | 2.397 | 2.34 | 0 | 0.816 | 2.44 | 31 | 2.40 | | | 1.007 | 4.66 | 1.261 | 2605 | 0.05 | 22.6 | 0.05 |
| 243.85 | | | | | | | | | | | | 4.65 | 1.262 | 2611 | 0.05 | 23.4 | |

FIG. 8GGG

DEVICES AND METHODS FOR MONITORING

INCORPORATION BY REFERENCE

This application claims benefit to U.S. Provisional Application No. 63/153,177, filed Feb. 24, 2021. This application is also related to U.S. Patent Publication No. 2019/0093065 titled "Methods, Devices, And Computer Program Products For Yeast Performance Monitoring In Fermentation Systems". These applications are incorporated herein by reference in their entirety, except to the extent that the incorporated material is inconsistent with the express disclosure herein, in which case the language in this disclosure controls.

BRIEF DESCRIPTION OF DRAWINGS

This application/patent contains at least one drawing executed in color.

The foregoing summary and the following detailed description are better understood when read in conjunction with the appended drawings. Example embodiments are shown in the drawings; however, it is understood that the embodiments are not limited to the specific structures depicted herein. In the drawings:

FIGS. 4A and 4B show an example sensor manifolds of a device for continuous fermentation monitoring, according to an example embodiment of the present disclosure.

FIGS. 5A and 5B show an example density sensor manifold of a device for continuous fermentation monitoring, according to an example embodiment of the present disclosure.

FIG. 7A shows a graph of un-optimized gravity in Example 1, according to an example embodiment of the present disclosure.

FIG. 7K is a plot showing filter range for optimization as determined by the standard deviation of optimized gravity for prior fermentations of the same beer style, according to an example embodiment of the present disclosure.

FIG. 7L shows an example rule that can apply in phase 0 (and only in phase 0, in some aspects of the disclosure), according to an example embodiment of the present disclosure.

FIG. 7N shows an example rule that can apply in phase 1, according to an example embodiment of the present disclosure.

FIG. 7O is a plot of the available data points and resulting optimized value around this time point for the fermentation; mode is the mode of the pump on values, according to an example embodiment of the present disclosure.

FIG. 7P shows an example rule that can apply in phase 2, according to an example embodiment of the present disclosure.

FIG. 7R shows an example rule that can apply in phase 3, according to an example embodiment of the present disclosure.

FIG. 7U is a plot of the available data points and resulting optimized value around this time point for the fermentation; mode is the mode of the pump on values, according to an example embodiment of the present disclosure.

FIGS. 8A, 8B, 8C, 8D, 8E, 8F, 8G, 8H, 8I, 8J, 8K, 8L, 8M, 8N, 8O, 8P, 8Q, 8R, 8S, 8T, 8U, 8V, 8W, 8X, 8Y, 8Z, 8AA, 8BB, 8CC, 8DD, 8EE, 8FF, 8GG, 8HH, 8II, 8JJ, 8KK, 8LL, 8MM, 8NN, 8OO, 8PP, 8QQ, 8RR, 8SS, 8TT, 8UU, 8VV, 8WW, 8XX, 8YY, 8ZZ, 8AAA, 8BBB, 8CCC, 8DDD, 8EEE, 8FFF, and 8GGG, are, collectively, an example spreadsheet of the algorithmic detailed results of the graph of example 1 in FIGS. 7A to 7U, according to an example embodiment of the present disclosure.

DETAILED DESCRIPTION OF ASPECTS OF THE DISCLOSURE

Figure 1:
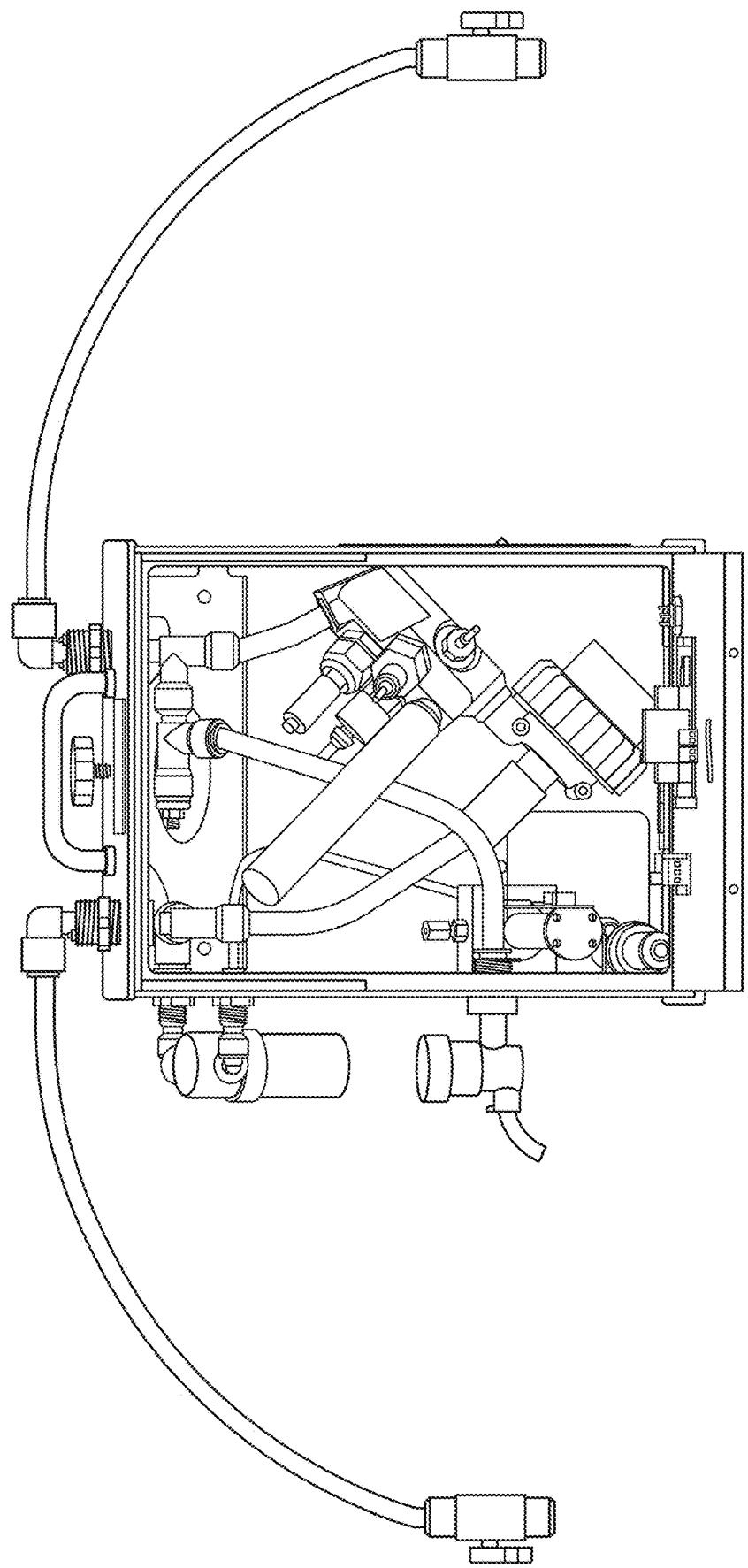
FIG. 1 shows an example device for continuous fermentation monitoring, according to an example embodiment of the present disclosure.

The terminology used in the present disclosure is for the purpose of describing particular example embodiments only and is not intended to be limiting. As used in the description of the embodiments of the disclosure and the appended claims, the singular forms "a," "an," and "the" are intended to include the plural forms as well, unless the context clearly indicates otherwise.

The term "and/or," as used herein, refers to and encompasses any and all possible combinations of one or more of the associated listed items.

The term "about," as used herein when referring to a measurable value such as an amount of a component, time, temperature, and the like, is meant to encompass variations of 20%, 10%, 5%, 1%, 0.5%, or even 0.1% of the specified amount. Unless otherwise defined, all terms, including technical and scientific terms used in the description, have the same meaning as commonly understood by one of ordinary skill in the art to which this disclosure belongs.

Example Device for Fermentation Monitoring and Method of Using

As used herein, "fermentation" refers to a chemical transformation of a substance by a microorganism. Microorganisms for fermentation may include, but are not limited to, fungi (e.g., yeast), bacteria, and/or algae (e.g., microalgae). In some embodiments of the present disclosure, a fermentation organism may be a fungus. In some embodiments, the fungus can be a yeast. Example types of yeast that may be analyzed include, but are not limited to, *Saccharomyces cerevisiae, Saccharomyces pastorianus, Saccharomyces bayanus, Brettanomyces Bruxellensis, Brettanomyces Lambicus, Kluyveromyces lactis, Yarrowia lipolytica*, or any combination thereof.

Processes that depend on fermentation, for example, modern brewing processes, can utilize yeast and can suffer from instances of variability, where the same or similar inputs yield differing results. Fermentation is a biological process that can be affected by a variety of factors, for example, operating conditions, yeast health, fermentation medium ingredients, and environmental contaminants. Because of the wide variety of factors that can influence fermentation performance, achieving consistent results in repeated fermentations can be improved or facilitated by continuous fermentation process monitoring. However, there are challenges for achieving effective continuous fermentation process monitoring, including that there can be a large variety of parameters or characteristics that are monitored, for example, concentration of sugar and fermentation by-products (e.g., ethanol, $CO_2$) in the medium, operating conditions (e.g., temperature, pressure), viable yeast cell concentration, pH, among others. Introduction of dissolved gases and particulates into the fermentation material can hinder accurate measurement of the fermentation process. In addition, equipment may need to be sanitized without impacting ability to monitor the fermentation process. In some aspects of the disclosure, a continuous fermentation monitoring system, device and method can be provided. In one embodiment, the device can be portable or capable of being removably coupled to a fermentation vessel, that can be moved from one fermentation vessel to another in a sanitary manner, e.g., without introducing biological or chemical contamination to the fermenting material or fluid.

The present disclosure relates to devices and methods for continuous monitoring of fermentation. In one embodiment, the fermentation can comprise ethanol or alcoholic fermentation, for example fermentation by any species of yeast. In one embodiment, fermentation can comprise fermentation of a carbohydrate containing solution to carbon dioxide one of the following alcohols or organic acids: ethanol, butanol, methanol, acetic acid, or lactic acid. The devices and methods provided herein can allow for real-time or near real-time monitoring of two or more characteristics of the fluid being fermented at varying times. The real-time or near real-time monitoring of two or more characteristics of the fluid at varying times, as further described herein, can allow for a more accurate representation of the level of fermentation of the fluid.

The present disclosure can comprise (i) fluid path design, which can allow for periodic extraction of fermenting material from fermentation vessels, can measure two or more characteristics of the fluid, and can return the fluid to the fermentation vessel, (ii) sensor selection, which can allow for measurement of fluid attributes or characteristics that may be relevant to the assessment of biological processes of fermentation and can be taken frequently enough and with sufficient accuracy to allow the calculation of specific gravity, (iii) measurement strategy, which can balance multiple factors that play a role in measuring fluid that is being pumped through a device and contains dissolved gases, which gases can escape the solution during periods of activity and can affect the quality of the measurement, and (iv) use of mathematical and statistical methods with models of biological fermentation progress to assess raw measurement results and achieve accurate assessments of gravity.

FIG. 1 shows an example device for continuous fermentation monitoring, according to an example embodiment of the present disclosure. The device can comprise an inlet and an outlet. The device can comprise one or more pumps. A first fluid path can be connected to the inlet, a sensor manifold, and the outlet. A second fluid path can be connected to the inlet, a second sensor component, and the outlet. In one embodiment, a first fluid path can be connected to the inlet, a sensor manifold, and the outlet, as well as to a second sensor component without the need for a second fluid path. Fermentation material or fluid to be measured can be pumped into the device from a fermentation vessel via the inlet and can be pumped from the device to the fermentation vessel via the outlet. From the inlet, the fluid can be pumped to the first fluid path, the second fluid path or the first and second fluid paths.

The sensor manifold can comprise two or more sensors for sensing two or more characteristics of a fluid. The two or more characteristics can comprise two or more of pH, fluid temperature, ambient temperature, fluid pressure, fluid conductivity and dissolved oxygen, cell counts, cell viability, turbidity, capacitance, concentration of organic compounds, $CO_2$ concentration, etc. The second sensor component can comprise a density sensor for sensing the density of the fluid. The inlet can allow fluid to enter, or be pumped into, the device and the outlet can allow fluid to exit the device. From the inlet, the fluid can be pumped to the first fluid path, the second fluid path, or both the first and second fluid paths. From the first and/or second fluid paths, the fluid can be pumped out of the device via the outlet. In one embodiment, the fluid can be pumped to the first fluid path, the first fluid path being connected to the inlet, a sensor manifold, and the outlet, as well as to a second sensor component without the need for a second fluid path. The device can be removably coupled to a fermentation vessel, for example, can be portable or capable of being moved from one fermentation vessel to another.

Also provided herein is a system for continuous monitoring of fermentation, comprising the device for continuous fermentation monitoring as described herein and one or more fermentation vessels. The device can be removably coupled to one or more of the fermentation vessels.

Figure 2A:
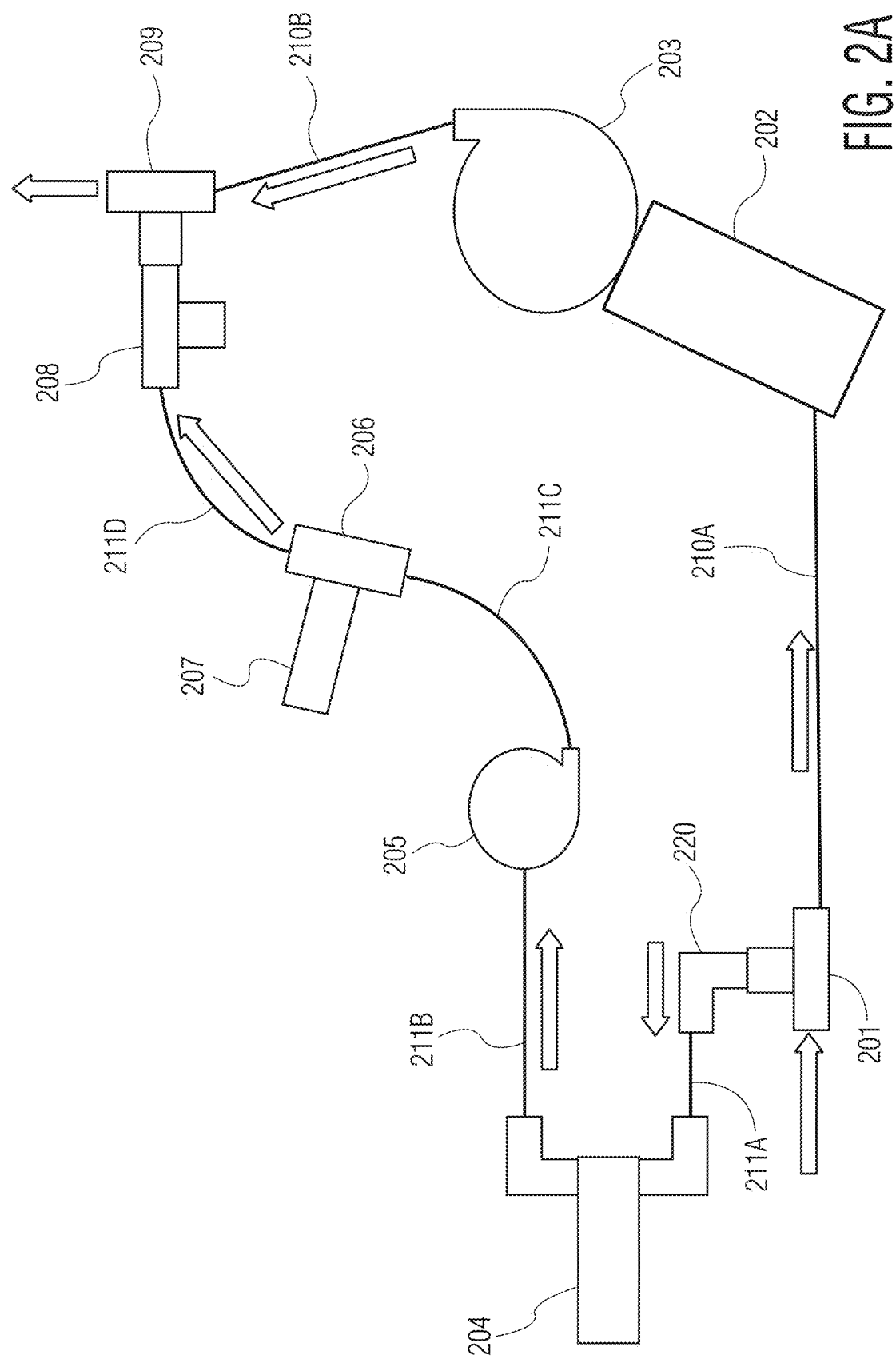
FIG. 2A shows an example flow chart showing fluid pathways in a device for continuous fermentation monitoring, according to an example embodiment of the present disclosure.

FIG. 2A shows an example flow chart showing fluid pathways in a device for continuous fermentation monitoring, according to an embodiment of the present disclosure. In one embodiment, a device can comprise a first fluid path (210), a second fluid path (211), an inlet tee (201), a sensor manifold (202), a main pump (203), a density filter (204), a density pump (205), a density manifold (206), a density sensor (207), a reducer tee (208) and an outlet tee (209). The device can also comprise a reducer elbow or similar structure (220). The device can also comprise a sample valve, which can be closed during normal operation and can be open during measurement periods. The arrows in FIG. 2 show the path(s) of fermentation material or fluid through the device. The first and second fluid paths can comprise one or more pipes or similar structures for moving fluid or material through the device.

Various parts of the first fluid path (210) and/or second fluid path (211) can comprise a pipe, coil or similar structure of the same or varying outside diameters (OD), as appropriate. Various parts of the first and/or second fluid paths can comprise a pipe, coil or similar structure of the same or varying lengths, as appropriate. For example, in one embodiment, first fluid path (210A) can comprise a pipe, coil or similar structure having a dimension of ½"OD×8" or any appropriate dimension. In one embodiment, first fluid path (210B) can comprise a pipe, coil or similar structure having a dimension of ½"OD×3," or any appropriate dimension. In one embodiment, second fluid path (211A) can comprise a pipe, coil or similar structure having a dimension of ¼"OD, or any appropriate dimension. In one embodiment, second fluid path (211B) can comprise a pipe, coil or similar structure having a dimension of ¼"OD, or any appropriate dimension. In one embodiment, second fluid path (211C) can comprise a pipe, coil or similar structure having a dimension ¼'OD×20" coil, or any appropriate dimension. In one embodiment, second fluid path (211D) can comprise a pipe, coil or similar structure having a dimension of ⅛"OD×58" coil, or any appropriate dimension.

In one embodiment, fermentation material or fluid from a fermentation vessel can be pumped into or provided to the device via inlet tee (201). From the inlet tee (201), the material or fluid can be pumped or provided to the sensor manifold (202) via the first fluid path (210) and main pump (203) and/or to the density filter (204) via reducer tee (208) and the second fluid path (211). The density filter (204) can be used to filter or remove particles that may impact the fluid density. The material or fluid can be pumped or provided from the sensor manifold (202) to the outlet tee (209) via the main pump (203) and the first fluid path (210). The material or fluid can be pumped or provided from the density filter (204) to the density pump (205) and from the density pump (205) to the density manifold (206). The density manifold (206) can comprise the density sensor (207). The material or fluid can be pumped or provided from the density manifold (206) to the reducer tee (208) and the outlet tee (209). The reducer tee (208) can be used to combine fluid paths of differing diameters or dimensions. The material or fluid can be pumped or provided back to the fermentation vessel via outlet tee (209).

Figure 2B:
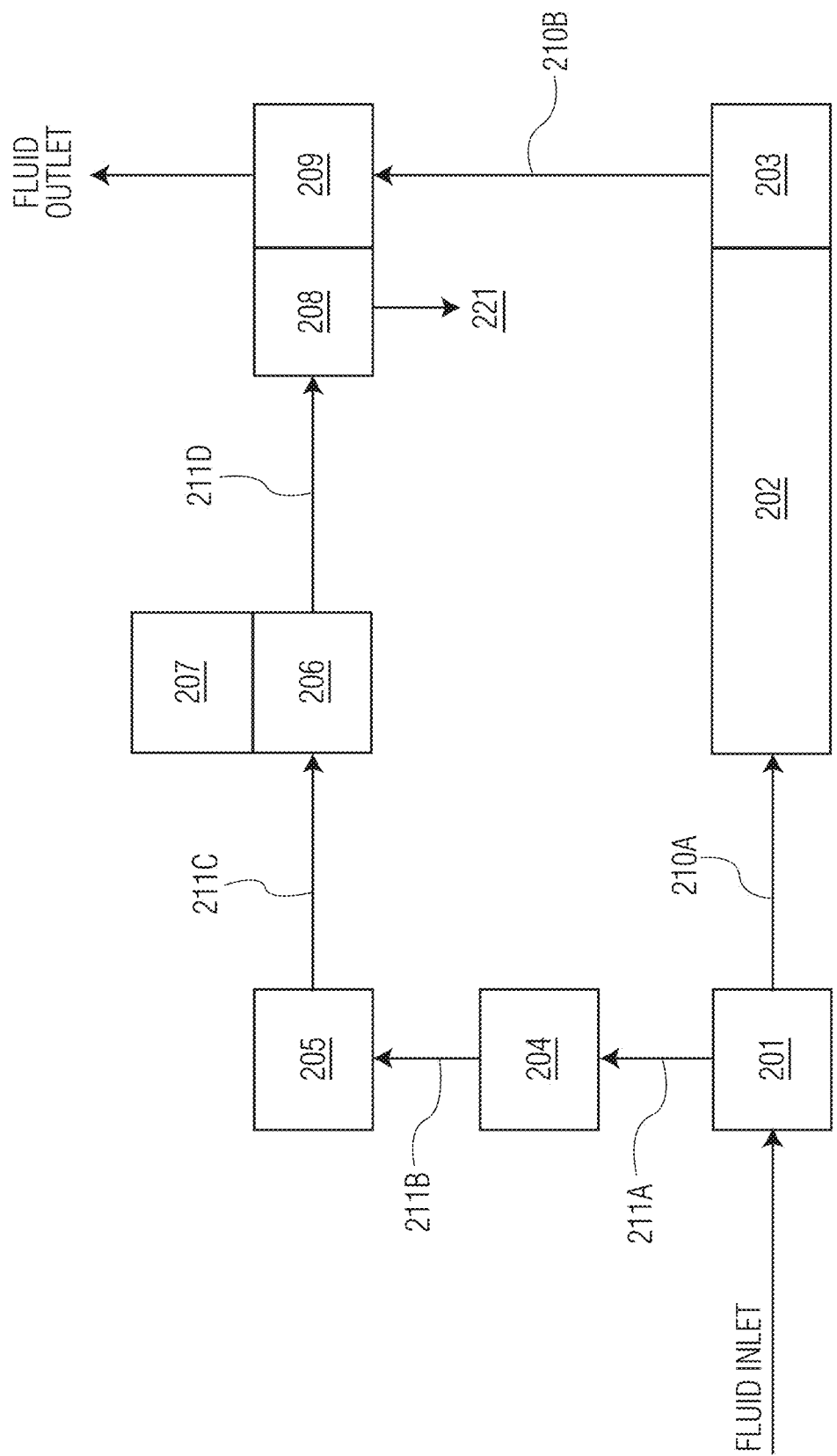
FIG. 2B shows an example flow chart showing fluid pathways in a device for continuous fermentation monitoring, according to an example embodiment of the present disclosure.

FIG. 2B shows an example flow chart showing fluid pathways in a device for continuous fermentation monitoring, according to an embodiment of the present disclosure. In one embodiment, a device can comprise a first fluid path (210), a second fluid path (211), an inlet manifold (201), a sensor manifold (202), a main pump (203), a density filter (204), a density pump (205), a density manifold (206), a density sensor (207), distribution manifold (208) and an outlet manifold (209). The device can also comprise a sample valve (221), which can be closed during normal operation and can be open during measurement periods. The arrows in FIG. 2B show the path(s) of fermentation material or fluid through the device. The first (210) and second (211) fluid paths can comprise one or more pipes or similar structures for moving fluid or material through the device. Various parts of the first fluid path (210) and/or second fluid path (211) can comprise a pipe, coil or similar structure of the same or varying outside diameters (OD), as appropriate. For example, in one embodiment, first fluid path (210A) can comprise a pipe, coil or similar structure having a dimension of ½"OD×8", or any appropriate dimension. In one embodiment, first fluid path (210B) can comprise a pipe, coil or similar structure having a dimension of ½"OD×3", or any appropriate dimension. In one embodiment, second fluid path (211A) can comprise a pipe, coil or similar structure having a dimension of ¼"OD, or any appropriate dimension. In one embodiment, second fluid path (211B) can comprise a pipe, coil or similar structure having a dimension of ¼"OD, or any appropriate dimension. In one embodiment, second fluid path (211C) can comprise a pipe, coil or similar structure having a dimension ¼"OD×20" coil, or any appropriate dimension. In one embodiment, second fluid path (211D) can comprise a pipe, coil or similar structure having a dimension of ⅛"OD×58" coil, or any appropriate dimension.

In one embodiment, fermentation material or fluid from a fermentation vessel can be pumped into or provided to the device via inlet manifold (201). From the inlet manifold (201), the material or fluid can be pumped or provided to the sensor manifold (202) via the first fluid path (210) and main pump (203) and/or to the density filter (204), and density manifold (206) via the second fluid path (211) and density pump (205). The material or fluid can be pumped or provided from the sensor manifold (202) to the outlet manifold (209) via the main pump (203) and the first fluid path (210). The material or fluid can be pumped or provided from the density filter (204) to the density pump (205) and from the density pump (205) to the density manifold (206). The density manifold (206) provides fermentation material or fluid to the density sensor (207). The material or fluid can be pumped or provided from the density manifold (206) to the distribution manifold (208) and the outlet manifold (209). The material or fluid can be pumped or provided back to the fermentation vessel via outlet tee (209).

Figure 3:
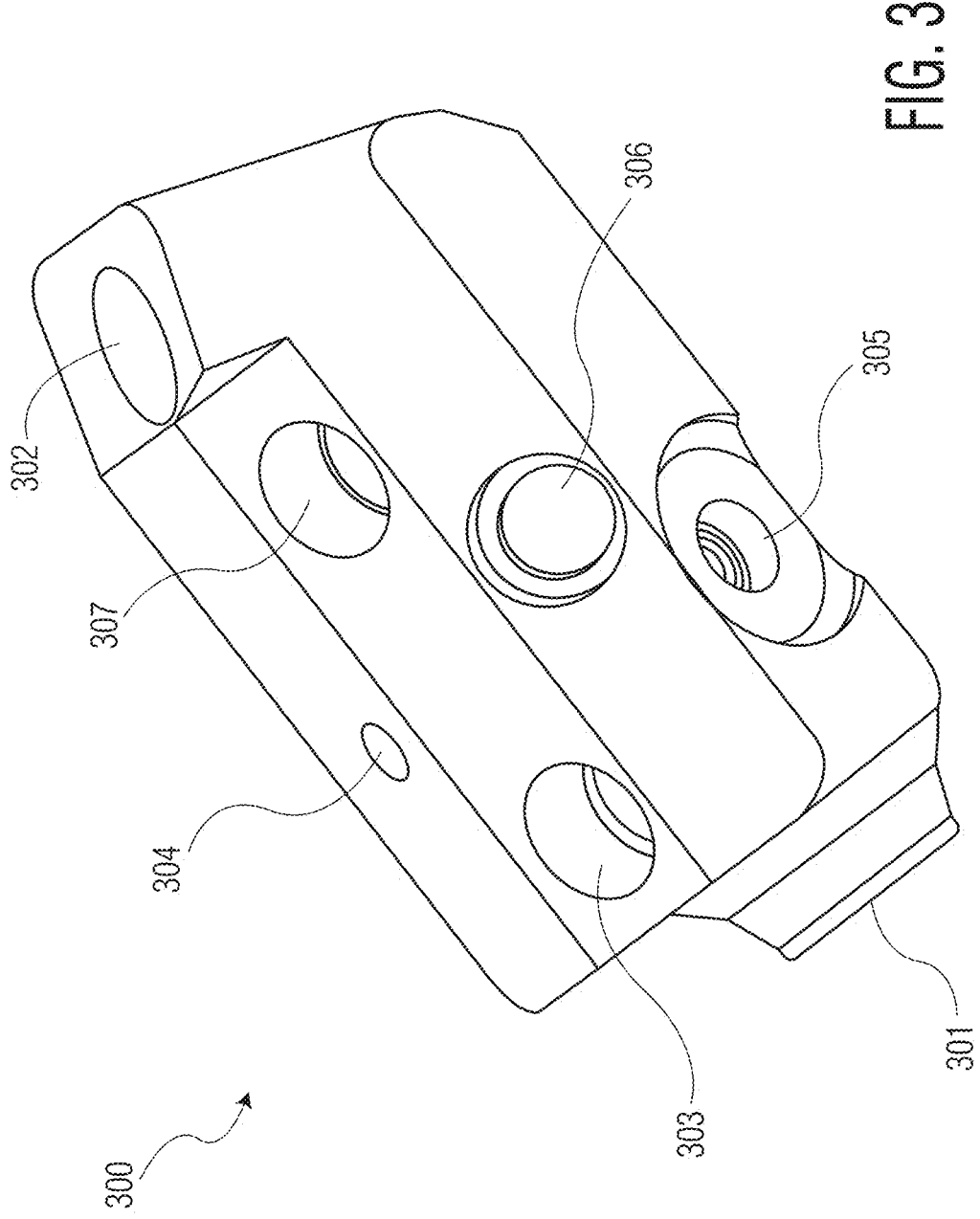
FIG. 3 shows an example sensor manifolds of a device for continuous fermentation monitoring, according to an example embodiment of the present disclosure.

FIG. 3 shows an example sensor manifold (300) of a device for continuous fermentation monitoring, according to an example embodiment of the present disclosure. Sensor manifold (300) can be part of a device for continuous fermentation monitoring described herein (but not shown here). Sensor manifold (300) can comprise two or more sensors for sensing two or more characteristics of a fluid. In one embodiment, sensor manifold (300) can comprise a pump or fluid inlet connection (301) and an outlet or fluid outlet or return connection (302). The material or fluid can enter the sensor manifold (300) from a first fluid path of the device via the pump or fluid inlet connection (301). The material or fluid can exit the sensor manifold (300) to a first fluid path of the device via the outlet or fluid outlet or return connection (302).

The sensor manifold (300) can comprise a pH sensor (303), for example a pH probe. The sensor manifold can comprise a pressure sensor (304), for example any appropriate sensor for sending pressure of a fluid or material. The sensor manifold can comprise a fluid or material temperature sensor (305), for example a fluid or material thermometer. The sensor manifold (300) can comprise a sensor for sensing conductivity of the fluid or material (306), for example a conductivity probe. The sensor manifold (300) can comprise a sensor for sensing level of dissolved oxygen in the fluid or material (307), for example a DO probe. The sensor manifold (300) can also comprise a sensor for measuring one or more of cell counts, cell viability, turbidity, capacitance, concentration of organic compounds, $CO_2$ concentration, etc. (not shown).

In one embodiment, fluid or material can be pumped or provided to the sensor manifold (300) and two or more characteristics of the fluid or material can be sensed by two or more of the following: pH sensor (303), pressure sensor (304), temperature sensor (305), conductivity sensor (306) and DO probe (307). The measurements or information sensed by the pH sensor (303), pressure sensor (304), temperature sensor (305), conductivity sensor (306) and/or DO probe (307) can be provided on a real-time or near real-time basis.

Figure 4B:
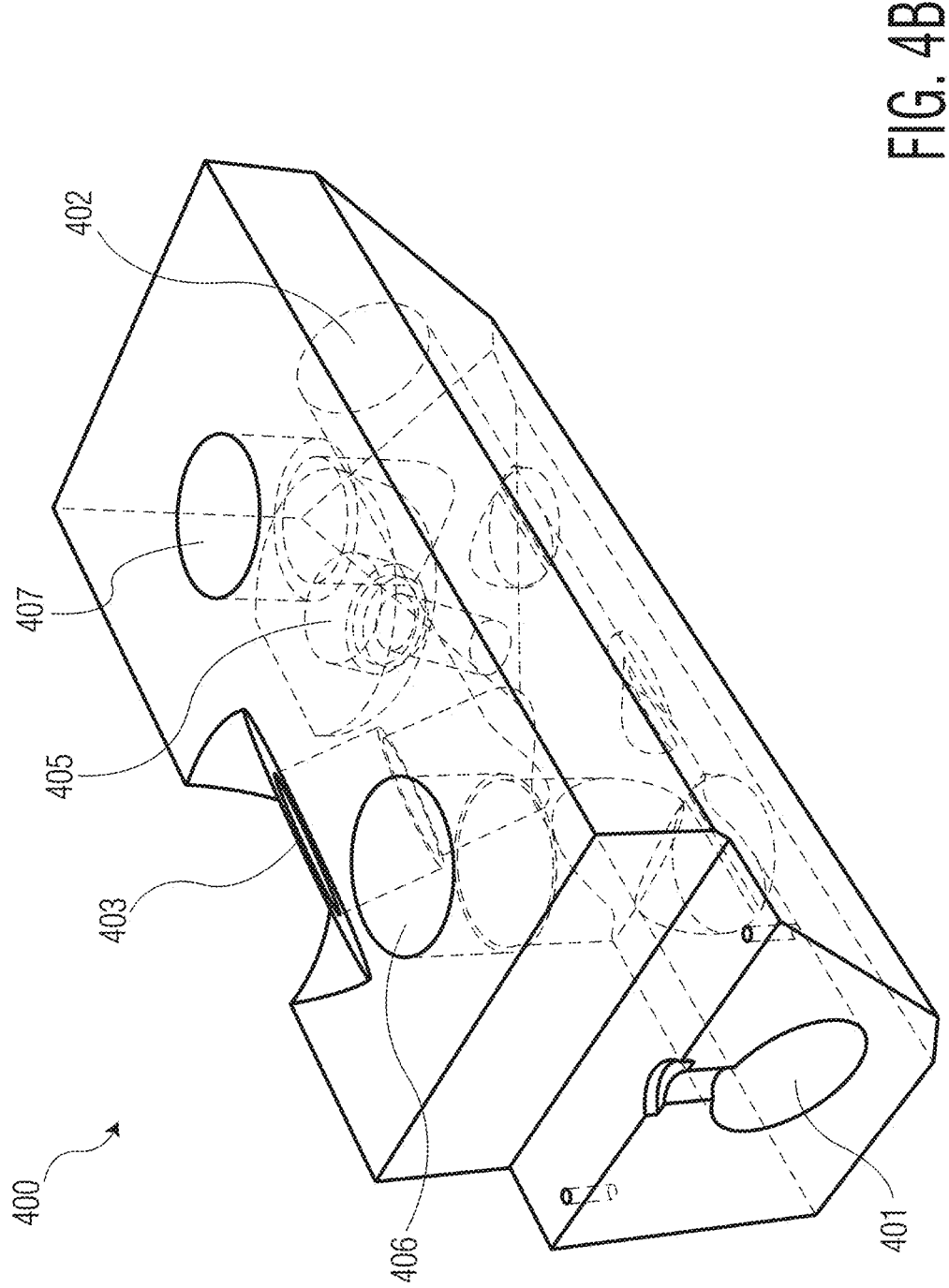

FIGS. 4A and 4B show an example sensor manifold (400) of a device for continuous fermentation monitoring, according to an example embodiment of the present disclosure. Sensor manifold (400) can be part of a device for continuous fermentation monitoring described herein (but not shown here). Sensor manifold (400) can comprise two or more sensors for sensing two or more characteristics of a fluid. In one embodiment, sensor manifold (400) can comprise a pump or fluid inlet connection (401) and an outlet or fluid outlet or return connection (402). The material or fluid can enter the sensor manifold (400) from a first fluid path of the device via the pump or fluid inlet connection (401). The material or fluid can exit the sensor manifold (400) to a first fluid path of the device via the outlet or fluid outlet or return connection (402).

The sensor manifold (400) can comprise a pH sensor (403), for example a pH probe. The sensor manifold can comprise a fluid or material temperature sensor (405), for example a fluid or material thermometer. The sensor manifold (400) can comprise a sensor for sensing conductivity of the fluid or material (406), for example a conductivity probe. The sensor manifold (400) can comprise a sensor for sensing level of dissolved oxygen in the fluid or material (407), for example a DO probe. The sensor manifold (400) can also comprise a sensor for measuring one or more of pressure, cell counts, cell viability, turbidity, capacitance, concentration of organic compounds, $CO_2$ concentration, etc. (not shown). In one embodiment, one or more sensors, for example, sensor for measuring pressure, pH, temperature, conductivity, dissolved oxygen (DO) level, cell counts, cell viability, turbidity, capacitance, concentration of organic compounds, and/or $CO_2$ concentration can be on a separate or second manifold. For example, a pressure sensor can be located on a separate or second manifold.

In one embodiment, fluid or material can be pumped or provided to the sensor manifold (400) and two or more characteristics of the fluid or material can be sensed by two or more of the following: pH sensor (403), temperature sensor (405), conductivity sensor (406) and DO probe (407). The measurements or information sensed by the pH sensor (403), temperature sensor (405), conductivity sensor (406) and/or DO probe (407) can be provided on a real-time or near real-time basis.

FIGS. 5A and 5B show an example density sensor manifold (500) of a device for continuous fermentation monitoring, according to an example embodiment of the present disclosure. FIG. 5A shows the outside of an example density sensor manifold (500) and FIG. 5B shows the inside of an example density sensor manifold (500) of a device for continuous fermentation monitoring, according to an example embodiment of the present disclosure. In one embodiment, density sensor manifold (500) can comprise a fluid intake manifold (501) and a fluid output manifold (502). The density sensor manifold (500) can comprise one or more bracket mounts (503), which can allow the density sensor manifold (500) to be removably or non-removably connected to the device (not shown). The density sensor manifold (500) can comprise a fluid outflow (504) to a density sensor (not shown) and a fluid return (505) from density sensor (not shown). The density sensor (not shown) can be any appropriate density sensor, for example, the Anton Parr density sensor. The density sensor (not shown) can be removably or non-removably attached to the density manifold (500) via one or more density sensor attach points (506), for example, four (4) attach points.

In one embodiment, fluid or material can be provided or pumped to the density sensor manifold (500) via the second fluid path (not shown) and the fluid intake manifold (501). The fluid or material can be pumped or provided from the fluid intake manifold (501) to the density sensor and then returned via the fluid outflow (504). The density sensor (not shown) can sense and/or measure the density of the fluid or material and can provide the measurements on a real-time or near real-time basis. The fluid or material can be pumped or provided from the density sensor to the density sensor manifold (500) via the fluid return (505). The fluid or material can exit the density manifold (500) via the fluid output manifold (502). The fluid or material can be pumped or provided back to the fermentation vessel from the density manifold (500) via one or more second fluid paths (not shown).

Provided herein are methods for continuous monitoring of fermentation. In one embodiment, a method for continuous fermentation monitoring can comprise providing a device as described herein, removably coupling the device to a fermentation vessel, pumping the fluid from the fermentation vessel to the device via the inlet, pumping the fluid from the inlet to the sensor manifold via the first fluid path, measuring two or more of characteristics of the fluid via the two or more sensors of the sensor manifold, pumping the fluid from the sensor manifold to the outlet via the first fluid path, pumping the fluid from the inlet to the density sensor via the second fluid path, measuring the density of the fluid via the density sensor, pumping the fluid from the density sensor to the outlet via the second fluid path, retuning the fluid to the fermentation vessel via the outlet, and varying timing of the pumping steps and the measuring steps to monitor a level of fermentation in the fluid. In one embodiment, the method can further comprise de-coupling the device from the fermentation vessel and removably coupling the device to another fermentation vessel. In an embodiment, the pumping steps can occur concurrently or consecutively. In one embodiment, the method can further comprise receiving measurements measured by the one or more sensors of the sensor manifold in real-time or near real-time, receiving measurements measured by the density sensor in real-time or near real-time, and calculating specific gravity of the fluid via the received measurements.

In one embodiment, the varying timing of the pumping steps and the measuring steps can allow for some measurement to be performed during fluid movement, and some measurement is performed when fluid is at rest, can comprise identifying a level of dissolved or escaped gas in the fluid during one or more periods, identifying which of the one or more periods allow for more accurate measurements of the one or more characteristic by the sensor manifold, identifying which of the one or more periods allow for more accurate measurement of fluid density by the density sensor, pumping the fluid to the sensor manifold via the first fluid path and measuring one or more fluid characteristics during an identified period, pumping the fluid to the density sensor via the second fluid path and measuring the fluid density during an identified period. In an embodiment, the periods that include a lower level of escaped gas may be more accurate than periods that include a higher level of escaped gas.

In one embodiment, the methods can comprise a measurement strategy for measuring and/or sensing the two or more characteristics of the fluid or material. The measurement strategy can comprise measuring the one or more characteristics of the fluid via the two or more sensors of the sensor manifold at a rate of about every 5 to about every 15 minutes or about every 10 minutes. The measurement strategy can comprise measuring the density of the fluid via the density sensor at a rate of about every 5 minutes to about every 6 hours, for example about every 20-40 minutes, about every 30 minutes, about every hour, about every 90 minutes, about every two (2) hours, about every two and a half (2.5) hours, about every three (3) hours, about every three and a half (3.5) hours, about every four (4) hours, about every four and a half (4.5) hours, about every five (5) hours, about every five and a half (5.5) hours, or about every 6 hours. In one embodiment, the measurement strategy can comprise measuring the density of the fluid via the density sensor at a rate of about every 20 to about every 40 minutes or about every 30 minutes.

In one embodiment, the measurement strategy can comprise relating the timing of the pump operation in the first fluid path, the pump operation in the second fluid path, readings from the sensor manifold and readings from the density sensor manifold and identifying a strategy for timing the pumping of fluid to the sensor manifold via the first fluid path and the pumping of fluid to the density sensor manifold via the second fluid path in a manner that provides better or more accurate readings for the determination of fermentation progress. In one embodiment, the determination of fermentation progress can be based on a calculation of specific gravity. The calculation of specific gravity can be based on the measurement readings from the density sensor. In one embodiment, the measurement strategy can improve the accuracy of the determination of fermentation progress by identifying measurements that are inaccurate based on the level of dissolved gas in the fluid or escaped gas (for example, dissolved oxygen, $CO_2$). These inaccurate measurements can be avoided during the calculation of specific gravity. In an embodiment, the timing of the pumping and measuring steps can be adjusted based on the degree of escaped gas present in the fluid.

Example Software for Fermentation Monitoring and Method of Use

A computerized system and method for continuous monitoring of fermentation is described herein. The computerized system can comprise: an inlet allowing fluid to enter the device; and an outlet allowing fluid to exit the device. A first fluid path can be connected to the inlet, the sensor manifold, and the outlet. The sensor manifold can comprise two or more sensors for sensing two or more characteristics of a fluid. A second fluid path can be connected to the inlet, the second sensor component, and the outlet. In one embodiment, a first fluid path can be connected to the inlet, a sensor manifold, and the outlet, as well as to a second sensor component without the need for a second fluid path. The second sensor component can comprise a density sensor for sensing the density of the fluid. In some aspects of the disclosure, a gravity measurement module can determine a change in the gravity of the fluid using the density of the fluid by varying timing of pumping and measuring to increase the accuracy of density measurement (and therefore calculated gravity) in order to determine the current level of fermentation in the fluid.

The two or more characteristics that are sensed can comprise any combination of: pH, fluid temperature, ambient temperature, fluid pressure, fluid conductivity, dissolved oxygen, cell counts, cell viability, turbidity, capacitance, concentration of organic compounds, and $CO_2$ concentration. The two or more sensors can comprise any combination of: a pH sensor, an ambient temperature sensor, a fluid temperature sensor, a fluid pressure sensor, a fluid conductivity sensor, a dissolved oxygen sensor, a sensor for measuring cell counts, cell viability, turbidity, capacitance, concentration of organic compounds, and $CO_2$ concentration.

Measurements measured by the one or more sensors of the sensor manifold can be received in real-time or near real-time. Measurements measured by the density sensor can be received in real-time or near real-time. The gravity of the fluid can be calculated via the received measurements.

One or more characteristics of the fluid can be measured via the one or more sensors of the sensor manifold at a rate of approximately 5 to 15 minutes (e.g., approximately every 10 minutes in some aspects of the disclosure). The density of the fluid can be reported at a rate of approximately 20-40 minutes (e.g., approximately every 30 minutes in some aspects of the disclosure) based on calculations from measurements taken continuously during that period.

The varying of the timing of the pumping and the measuring can be determined. A level of dissolved or escaped gas in the fluid during one or more periods can be identified. In an embodiment, periods that include a lower level of escaped gas can be more accurate than periods that include a higher level of escaped gas. Which of the measurements during a period before pumping, during pumping, and after pumping (or any combination of: before pumping, during pumping and after pumping) that represents the most accurate measurements of the one or more characteristics by the sensor manifold can be identified. Which of the measurements during a period before pumping, during pumping, and after pumping (or any combination of: before pumping, during pumping, and after pumping) that represents the most accurate measurement of fluid density by the density sensor can be identified. The fluid can be pumped to the sensor manifold via the first fluid path and one or more fluid characteristics can be measured during an identified period. The fluid can be pumped to the density sensor via the second fluid path and measuring the fluid density during an identified period. Data can be obtained while the fluid is in motion and/or at rest. Density observations can then be obtained. Multiple measurements can be taken and analyzed while the fluid is at motion and/or at rest within a defined period in order to calculate an estimated gravity value. Statistics can be calculated for multiple density observations using the fluid at rest observations and the fluid in motion observations. A rule set to use can be determined from a predetermined group of rule sets using the calculated statistics. The rule set can be used to define an estimated value of gravity of the fluid based on the phase of the fermentation. It can then be determined whether the measured value of gravity is within a predetermined range of the estimated value of gravity.

Effect of Gas on Continuous Gravity Measurement

The basis of measuring gravity (representing the amount of sugar available in a fermentable material) can be through fluid density. Accurate measurement of fluid density may require a sample volume with ideally zero escaped gas (e.g., bubbles). One of the challenges of measuring gravity in a continuous flow system can be how to ensure that density readings are taken when there is no escaped gas in the sample. Avoiding escaped gas is made more difficult when agitation is introduced, e.g. by pumping.

During periods where fluid is at rest, gas may escape a sample volume due to the lower density of the gas compared to the fluid; gas bubbles will often migrate vertically, when possible, based on the construction of the container holding the volume. This migration of escaped gas can permit a measurement chamber to decrease the amount of escaped gas over time when fluid is at rest.

When high volumes of gas are present, for example, enough to create pockets of foam, adding pressure to the sample volume may result in more accurate measurements of density. The degree to which fermenting fluid produces escaped gas changes over the course of the fermentation due to activity of the fermenting organism and can vary based on the chemical composition of the fermenting fluid. As a result of these factors that create variation in the presence of escaped gas, the optimization algorithm described here can include varying the length and frequency of periods when one or more pumps are operating to maximize the potential of measuring fluid with little to no escaped gas.

The statistics can comprise any combination of: a number of observations within the current filter range; a maximum observed fluid in motion data value; a 2nd largest fluid in motion data value; a mean fluid in motion data value; a mode of fluid in motion data values; a standard deviation of fluid in motion data value; and a maximum fluid at rest data value that occurs at a pre-determined frequency (e.g., of 3 or higher) during a pre-determined time frame (e.g., in the prior 15 minutes).

In an embodiment, the present disclosure relates to systems and methods of continuous fermentation monitoring. The monitoring systems and methods can provide visibility and control of active fermentations. For example, the monitoring devices, systems and methods of this disclosure can enable fermented product manufacturers to consistently produce high quality products at lower costs, improve operational efficiency, or reduce or eliminate avoidable water and ingredient waste, and any combination thereof.

Gene Expression

Gravity describes the current state of the carbohydrate containing solution. The rate of change of gravity is impacted directly by the consumption of those carbohydrates by the fermenting microorganisms and their conversion of the carbohydrate to intermediates and then final products (alcohols or organic acids). These conversions are performed by enzymes whose level and activity are controlled by gene expression. The gene expression status of a microorganism population provides insight into the health of the microorganisms and can be measured indirectly by the fermentation activity of the microorganism population. Gene regulatory networks in healthy cells and/or good conditions promote high levels of conversion by fermenting enzymes, while other factors that promote cell proliferation, health, and efficiency are activated and maintained. In unhealthy cells and/or poor environmental conditions, due to the activity of gene regulatory networks, these enzymes are present in lower concentrations and/or are inhibited by stress-management pathways. By measuring the rate of change of gravity during a fermentation, key signals of overall microorganism health can be determined by observing whether a population of cells is efficiently fermenting the carbohydrate solution.

In cells known to be healthy, tasked with fermentation of a rich carbohydrate solution, the gravity rate of change can be used to observe the health and phasing of the organism by inferring the cell gene-expression state. Cells can be divided into phases of gene-expression programs that impact the rate of fermentation. Cells can adapt to the fermentation conditions, can proliferate (e.g., add biomass), can convert the bulk of the carbohydrate solution into product, and can enter a terminal phase where efficient fermentation is no longer possible. All of these phases can be reflected in the relative rate of change for gravity observed during fermentation.

In healthy cells at the onset of fermentation, there can be a phase with little to no change in gravity while the cells express a gene-expression suite that can generate proteins and enzymes that can allow for adaptation to the new conditions and for cells to "remodel" the fermentation solution to their own needs. Cells can utilize the rich carbohydrate solution at a faster rate but may not utilize the solution at a maximal rate. Cells can suppress the adaptation genes and turn on genes for factors required for cell division and proliferation. This can allow the population to grow and form a significant amount of the biomass in the fermentation solution. Once cells reach a particular cell population (which can vary for each organism/solution combination), the cell gene expression promoting proliferation can shut off and the cells in the population can increase the rate of gravity change by expressing the genes that produce enzymes to convert the carbohydrate solution to the fermentation products. This is the production phase. Finally, cells can experience conditions that are no longer optimal for fermentation, during this phase, the rate of gravity change can slow. Cells can repress the genes responsible for fermentation while activating stress management and survival gene programs impacting their ability to convert the carbohydrates into products. Some of the cells can die at the end of fermentation, further impeding the fermentation rate. In this way, gravity can be a good indicator of the cell-states and the genes responsible for those states, throughout a fermentation.

Anchor and Gravity Estimation

During periods of the most active fermentation, it may not be possible to obtain measurements that consist of fluid with no escaped gas. During such periods, it may be possible to estimate the gravity value based on a variety of factors including the trends of prior gravity readings, readings at the same time point in prior fermentations of the same recipe, and other factors.

Points at which no estimates are required due to confidence in the available measured values may be referred to as anchors. When estimation is required due to limited or no availability of valid readings, estimated values may be re-estimated when a new anchor point is encountered. At the time a new reading is identified as an anchor, the optimization algorithm may re-evaluate any estimated points between the last anchor and the current one, updating the estimates based on models of the expected pattern of change in gravity between the two points compared to prior fermentations of the same brand or of the same style. The current point in time may be useful for decisions based on the most current data. For retroactive analysis and comparison against prior or future fermentation, the entire series can be useful. The algorithm disclosed herein can be used to serve both situations (e.g., for current point in time analysis and for retroactive analysis and comparison against prior or future fermentation).

In some aspects of the disclosure, the optimized measurements can be used to give insight into the state of the fermentation (e.g., expected time to completion, possible interventions to improve the fermentation, etc.) Varying the timing can allow for the measurement of one or more sensors to be made at different times relative to when the pump (or pumps) is causing fluid to flow past that sensor, e.g. readings can be taken for a spectrum of different states including with the pump off (fluid at rest) and pump on (fluid in motion) and variations there, such as the pump has been recently turned on/off (e.g. within a predetermined time period) during which the measurements are taken, or not recently been turned on/off. The length of time the pump is in operation can also be varied. This allows the sensors to take readings under a variety of fluid conditions which may affect how accurately the sensor can measure the underlying parameter. It has been found that this additional information then allows various statistical processing of the data to identify accurate readings and/or make more accurate estimates of the parameter being sensed from the readings. In an embodiment, hundreds of individual measurements may be taken during the predetermined time period to provide a single estimate for the predetermined time period.

This may be used for any reading, but may be useful with the density sensor reading, which can give an indication of specific gravity of the fermentation liquid and can thus be correlated with the progression of the fermentation (as will be understood, as fermentation proceeds, sugars are converted by the metabolism of the fermentation organism from an initial level as determined by the fermentation "recipe" to a completed level, for which the specific gravity reading gives an indication). In particular, carbon dioxide ($CO_2$) bubbles in the liquid can be a problem in obtaining accurate readings, or more specifically carbon dioxide that has come out of solution has formed bubbles in the fluid. By changing the timing of the measurements, it may more likely that measurements will be taken at points where there is less bubbles formed, where readings can be assumed to be more accurate, and so inaccurate readings are discarded by the statistical techniques. Alternatively, or additionally, another sensor may detect $CO_2$ readings in the liquid, and thus can be used to directly give an indication of the current state of $CO_2$ which correlates with sensor accuracy, which can be used to determine which sensor readings (e.g., density readings), are most reliable.

In some aspects of the disclosure, the sensors may be in the same fluid path. However, in some embodiments, it has been found that having separate paths for some sensors is useful. For example, the density sensor may be in a different fluid path from one or all other sensors. The paths may have different pumps, allowing fluid flow to be individually controlled to the different paths. This again may be useful in allowing the statistical techniques to more accurately obtain measurements of the fermentation fluid based on the sensor readings.

Various statistical techniques can be used, such as comparing each sensor value with a trend established by previous sensor readings to see if it is within an expected bound. Measurements outside a range may be discarded and optimally replaced by estimated values based on an identified trend, e.g. slope. Alternatively average values (mode, median or mean) or maximum or minimum values or "nth most" maximum or minimum values (e.g. 2nd largest) may be identified over a measurement time period and used to optimize the reading. A set of rules may be applied in order to obtain an estimated value at a given time based on a sensor reading and optionally the recent history of sensor readings. In embodiments, the rules used may depend on the stage of the fermentation. For instance, early in the fermentation process after yeast has been added, the sugar metabolic processes of the yeast may still be at a low level compared with later in the fermentation process where the yeast has reached peak activity, and thus the levels of $CO_2$ can be expected to be different which affects the accuracy of the sensor readings during this period in a particular way. Different rules and statistical processes may be best suited at each state of the fermentation. These may be learned by training on the data of past fermentations or manually set. The stage of the fermentation may be determined based on time measurements, e.g. each stage corresponding to a time period relative to the yeast being pitched or some other useful marker. Alternatively, or additionally, the stage of fermentation may be based on the density reading which correlates with how far fermentation has progressed. In some embodiments, the calculation of the stage of fermentation may be based on other sensor readings, which as a group correlate with stages of fermentation. and may allow further insight into the biological state of the yeast and the genetic regulatory networks controlling its metabolism and cellular processes at that time leading to particular chemical changes in the fermentation liquid at that time. Optionally, this may be used with the techniques in U.S. Patent Publication No. 2019/0093065, which discusses gaining insight into the state of a fermentation organism based on using sensor readings as a proxy.

Further techniques may be used to improve the accuracy of measurements. For instance, in an embodiment, other sensor readings may be used to look for possible external "interventions", e.g. the operator changing a fermentation condition, which may cause a spike or other deviation from the underlying trend. For instance, adding additives may cause a sudden change in gravity readings. The statistical techniques should recognize that this sudden change is "valid" rather than an anomalous reading. By looking at other sensor values in combination, it may be determined that an intervention has taken place. For instance, a sudden change in value or rate of (say) a density reading may be determined to be valid if accompanied by a simultaneous sudden change in (say) pH, and/or change in rate of increase of (say) temperature or any combination thereof, which as a set is indicative of a particular intervention, e.g. the operator adding sugar to the liquid. Otherwise, the reading may be discarded as an outlier in favor of an estimated value.

In an embodiment, a technique is to compare sensor values against sensor values for prior fermentations which have been monitored by the system and recorded in a database. These may be for instance recorded for other fermentations in the same fermentation vessel, for fermentations of the same recipe, for fermentations of the same operator, for a fermentations of a similar type (e.g. in terms of end product: beer, cider, etc). This can be processed to establish ranges of expected values for measurements at different points during the fermentation. New values falling outside the ranges may be discarded and estimated values used in their place.

The statistical techniques may establish a trend in the measured values. Where a new measurement is established to be inaccurate, an estimated value may be used in its place, e.g. by extrapolating the trend. Where later on further values are measured that are determined to be accurate (named "anchor" points in this disclosure), any estimated values between this anchor point and the previous anchor point may be re-estimated in the light of the new anchor value, e.g. an the trend can be updated and the estimated values interpolated.

The result may be more accurate and reliable readings for various parameter giving improved insight into the state of a fermentation, which can be used in many ways to control the progress of the ongoing fermentation, either automatically or manually by presenting the operator with information. The overall time series of measurements for a fermentation may be stored in a database and used off-line for comparison with other fermentations, for diagnostics and to gain insights. In particular, they can be used to establish normal ranges of measured parameters for fermentations at different time points during the fermentation which can be used for real time fermentation in optimizing measured values as discussed herein.

Figure 6:
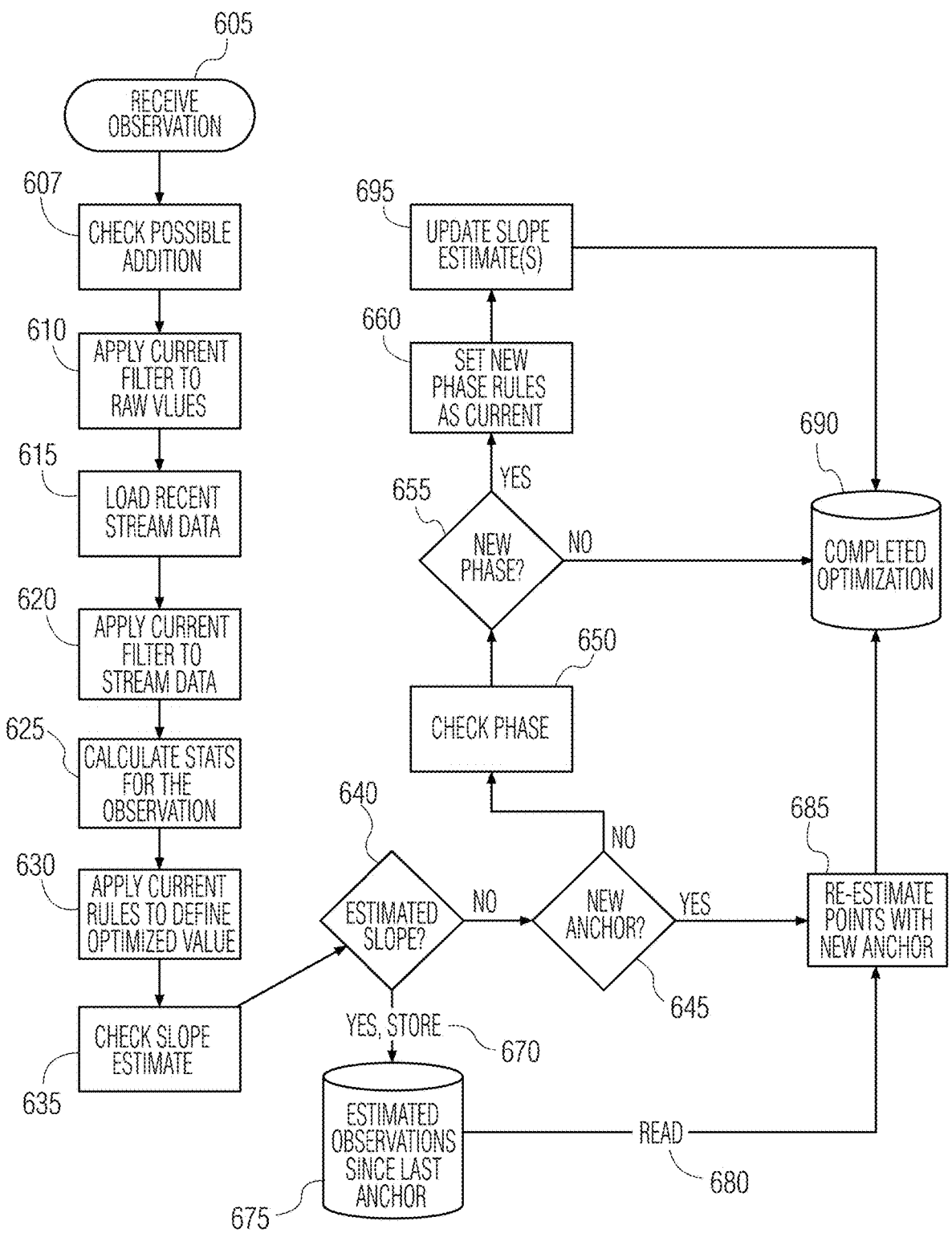
FIG. 6 shows an example optimization flowchart, according to an example embodiment of the present disclosure.

FIG. 6 is an example optimization flowchart, according to aspects of the disclosure. In 605, an observation can be received. In 610, a current filter can be applied to raw values. In 615, recent stream data can be loaded. In 620, current filter can be applied to the stream data. In 625, stats can be calculated for the observation. In 630, current rules can be applied to define the optimized value. In 635, slope estimates can be checked. In 640, it can be determined if the slope is estimated. If yes, in 670, the slope can be stored. In 675, the observations since a last anchor can be estimated. In 680, they can be read. In 685, points can be re-estimated with a new anchor.

If in 640, if the slope is not estimated, in 645 it can be determined if there is a new anchor. If yes, in 685 points can be re-estimated with a new anchor. In 690, the optimization can be completed. In 695, the slope estimate can be updated. If in 645, it is determined there is not a new anchor, in 650, the phase can be checked. In 655, it can be determined whether there is a new phase. If yes, in 660, the new phase rules can be set as the current rules. If no, in 690, the optimization can be completed. In 695, the slope estimate can be updated.

FIG. 7 illustrates an example algorithmic description with example pseudo-code for steps depicted in the flowchart of FIG. 6.

Examples of Optimization

Figure 7A:
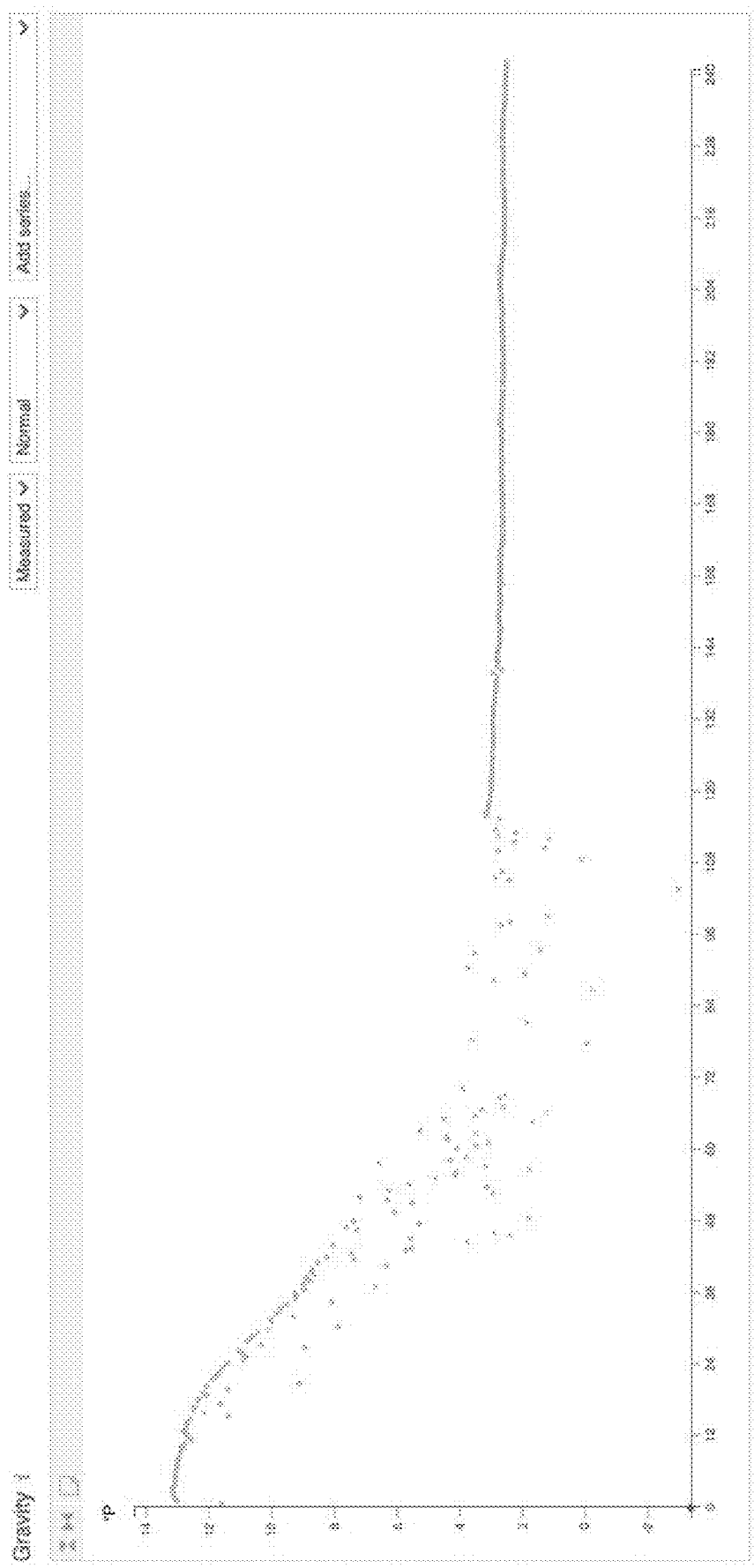
FIGS. 7A-7U illustrate an example algorithmic description with example pseudo-code for steps depicted in the flowchart of FIG. 6, according to an example embodiment of the present disclosure.
Figure 7B:
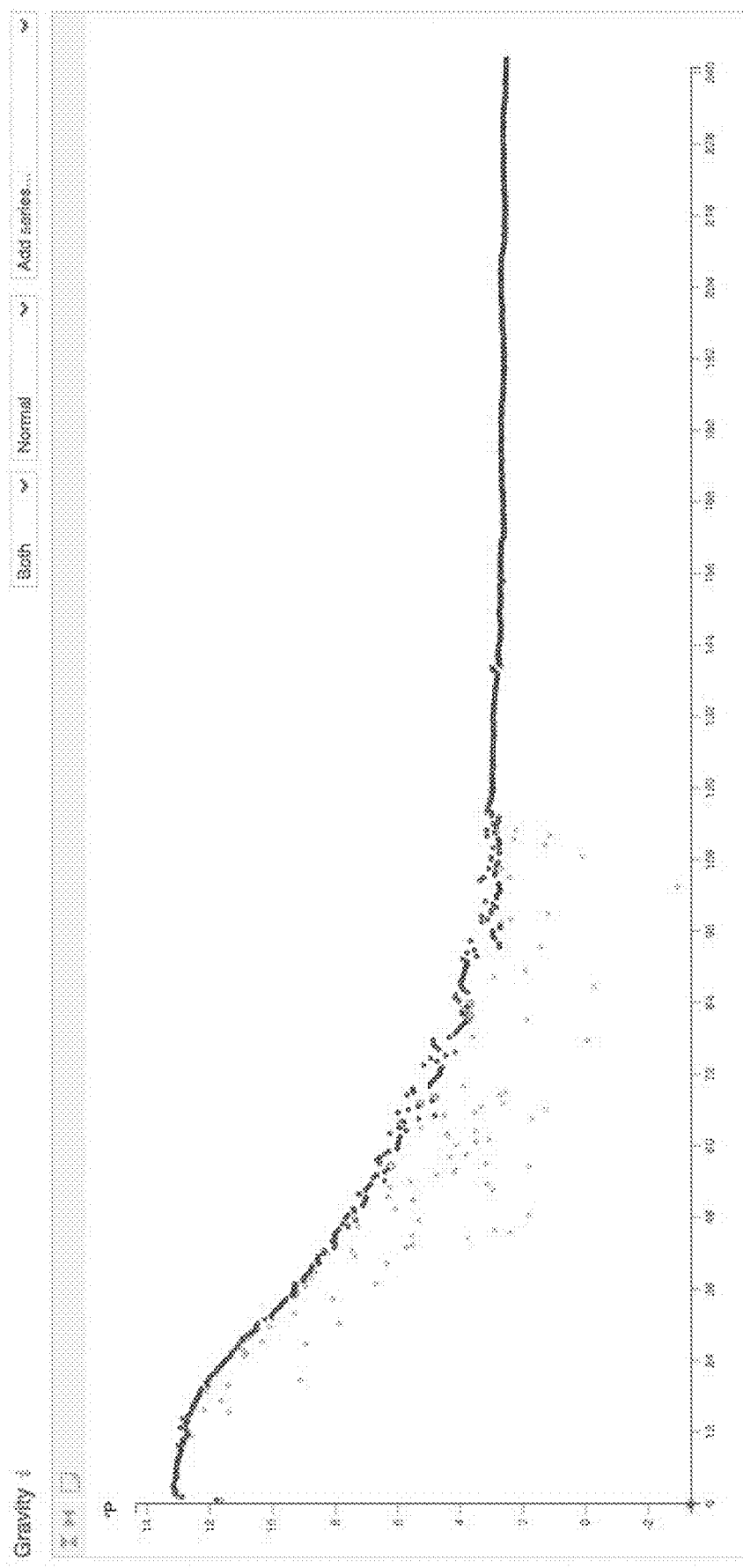
FIG. 7B shows a graph of optimized gravity in black overlaid on un-optimized in gray in Example 1, according to an example embodiment of the present disclosure.
Figure 7C:
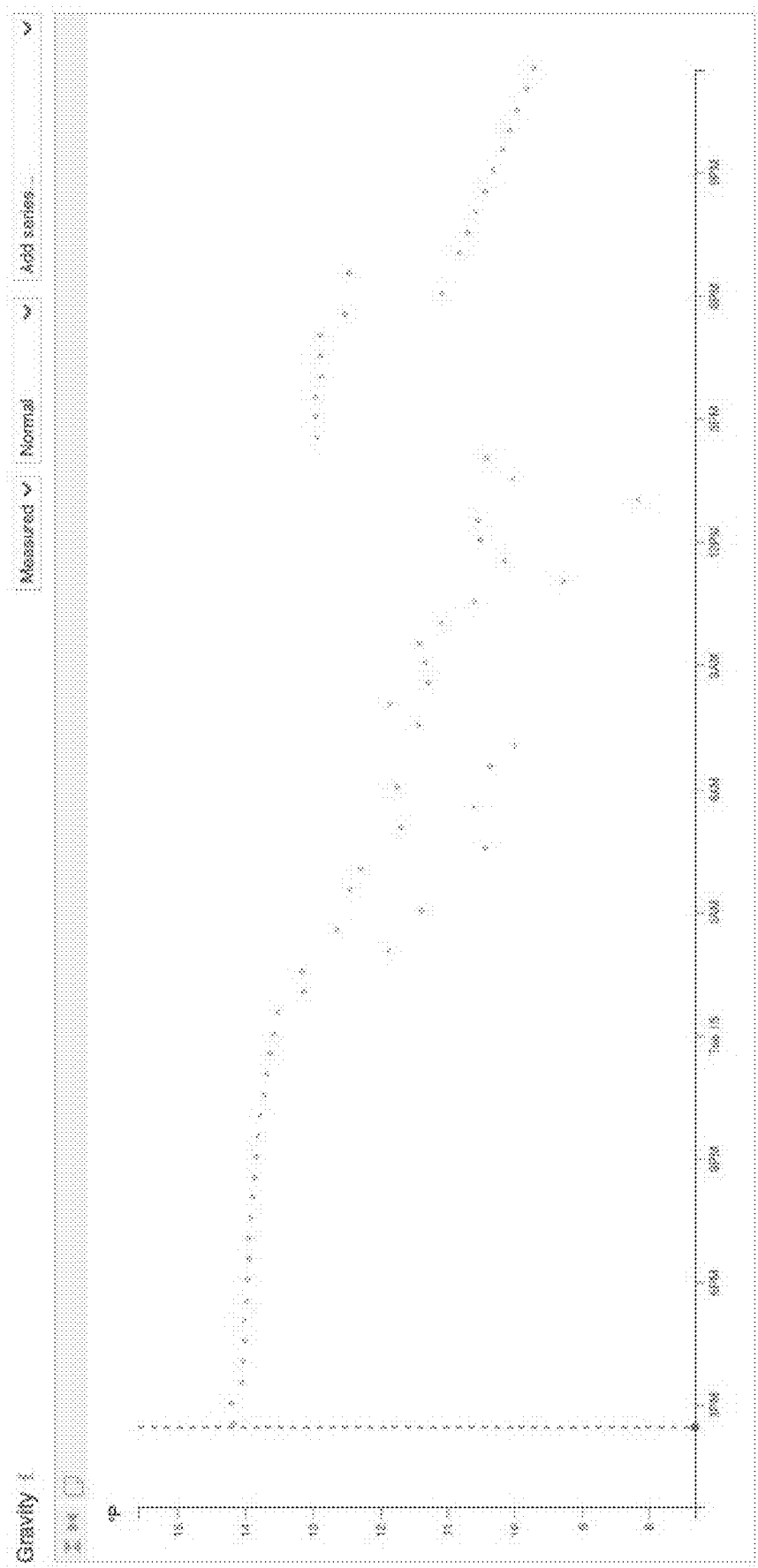
FIG. 7C shows a graph of un-optimized gravity in Example 2, according to an example embodiment of the present disclosure.
Figure 7D:
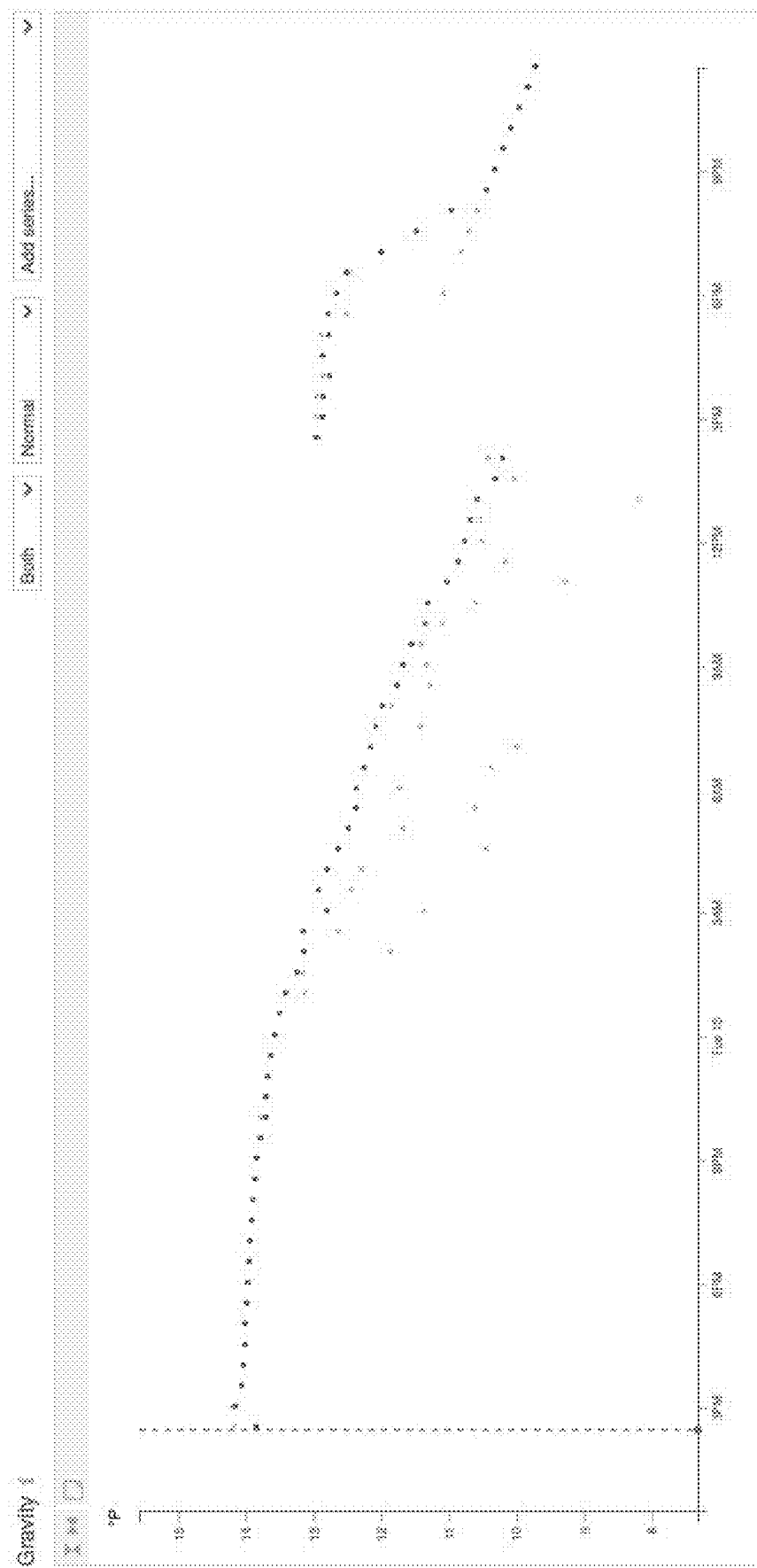
FIG. 7D shows a graph of optimized gravity in black overlaid on un-optimized in gray in Example 2, according to an example embodiment of the present disclosure.
Figure 7E:
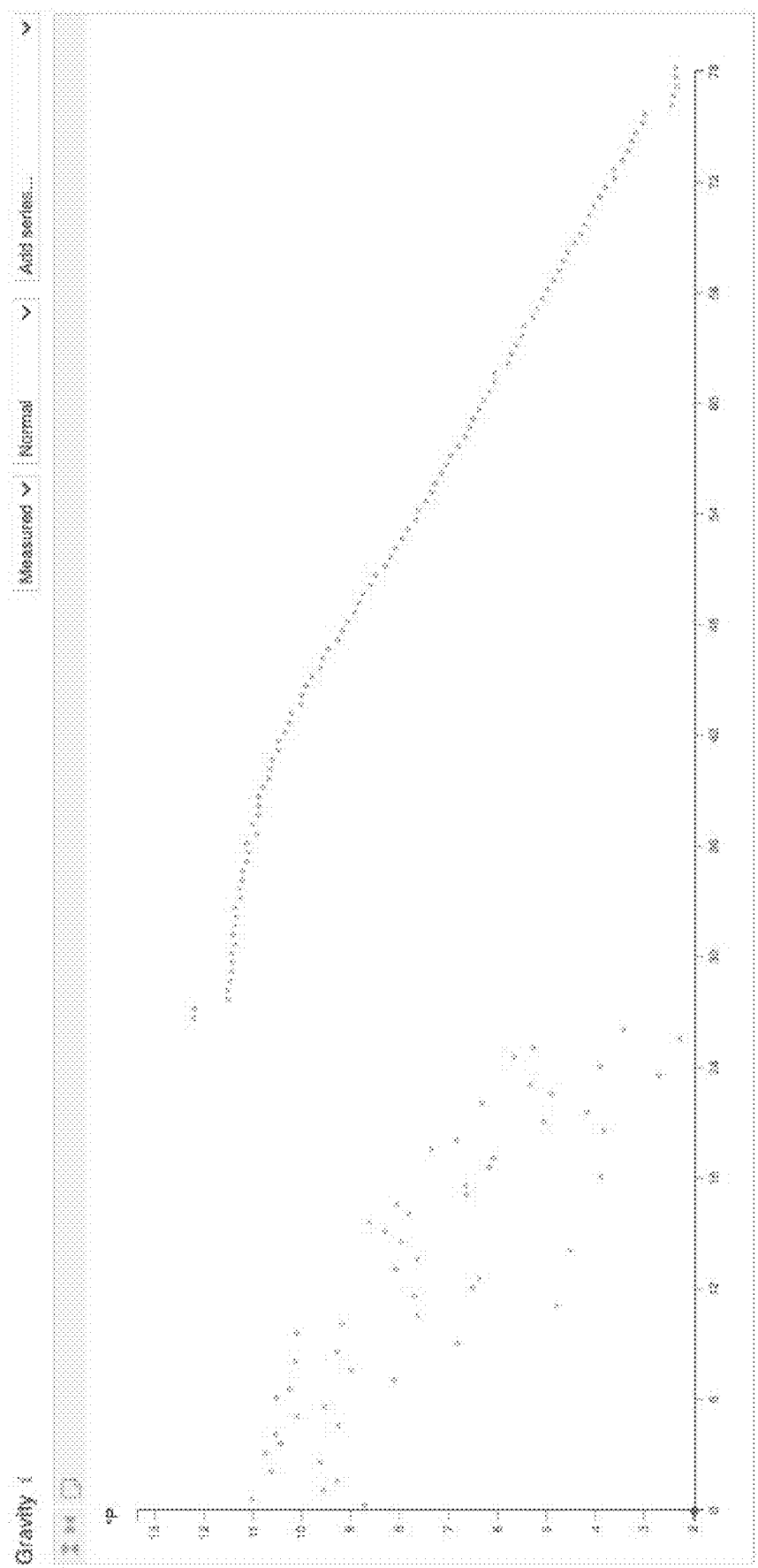
FIG. 7E shows a graph of un-optimized gravity in Example 3, according to an example embodiment of the present disclosure.
Figure 7F:
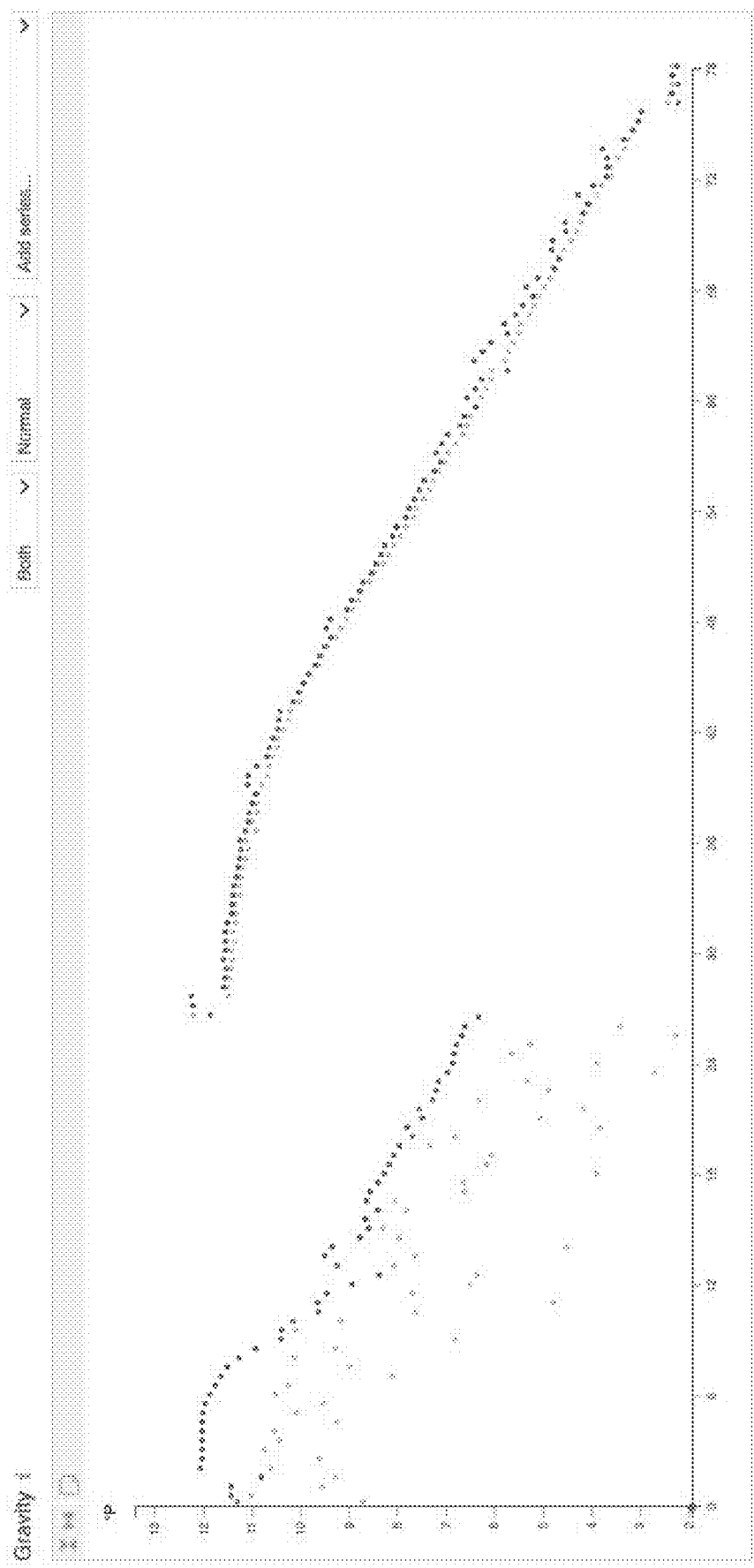
FIG. 7F shows a graph of optimized gravity in black overlaid on un-optimized in gray in Example 3, according to an example embodiment of the present disclosure.

FIGS. 7A-7F show an original reported graph based on un-optimized (measured) results, and then a graph with the optimized results overlaid over the measured results in Examples 1-3, respectively. FIG. 7A shows un-optimized gravity in Example 1. FIG. 7B shows optimized gravity in black overlaid on un-optimized in gray in Example 1. FIG. 7C shows un-optimized gravity in Example 2. FIG. 7D shows optimized gravity in black overlaid on un-optimized in gray in Example 2. FIG. 7E shows un-optimized gravity in Example 3. FIG. 7F shows optimized gravity in black overlaid on un-optimized in gray in Example 3.

An example factor beyond process changes that can make optimization more challenging that simple curve fitting is that errors and/or variances may not be distributed evenly around the correct values; the error bias may be significantly in one direction (e.g., less than the correct value) in most cases, with only occasional (e.g., frequency varying by phase) errors in a positive direction. This can be due to the primary error factor being the presence of un-dissolved gas in the fluid being measured, which can result in gravity being mis-reported to be lower than it actually is.

Example Algorithm Details

Figure 7G:
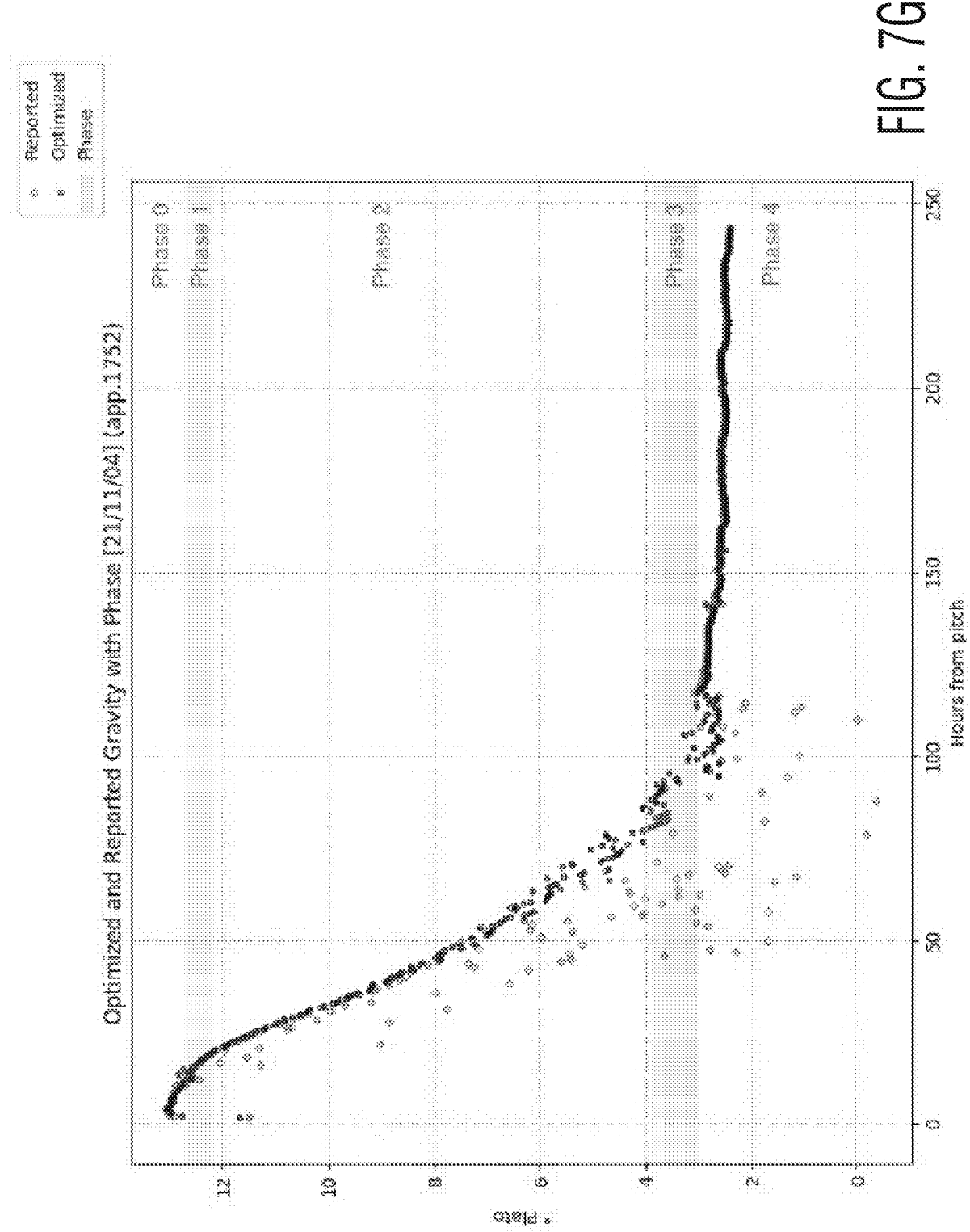
FIG. 7G is a depiction of fermentation phase using the same dataset as Example 1, according to an example embodiment of the present disclosure.
Figure 7H:
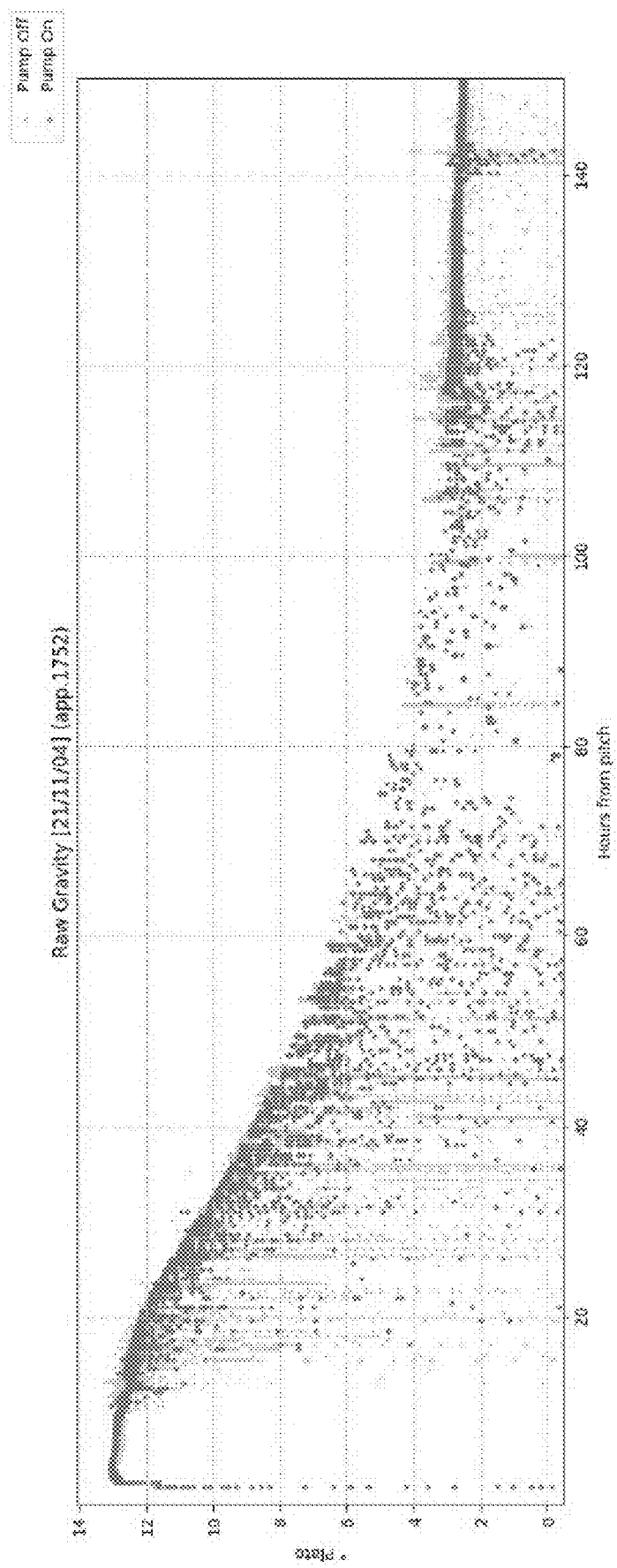
FIG. 7H is a depiction of individual gravity readings taken while the density pump is on vs. off, according to an example embodiment of the present disclosure.
Figure 7I:
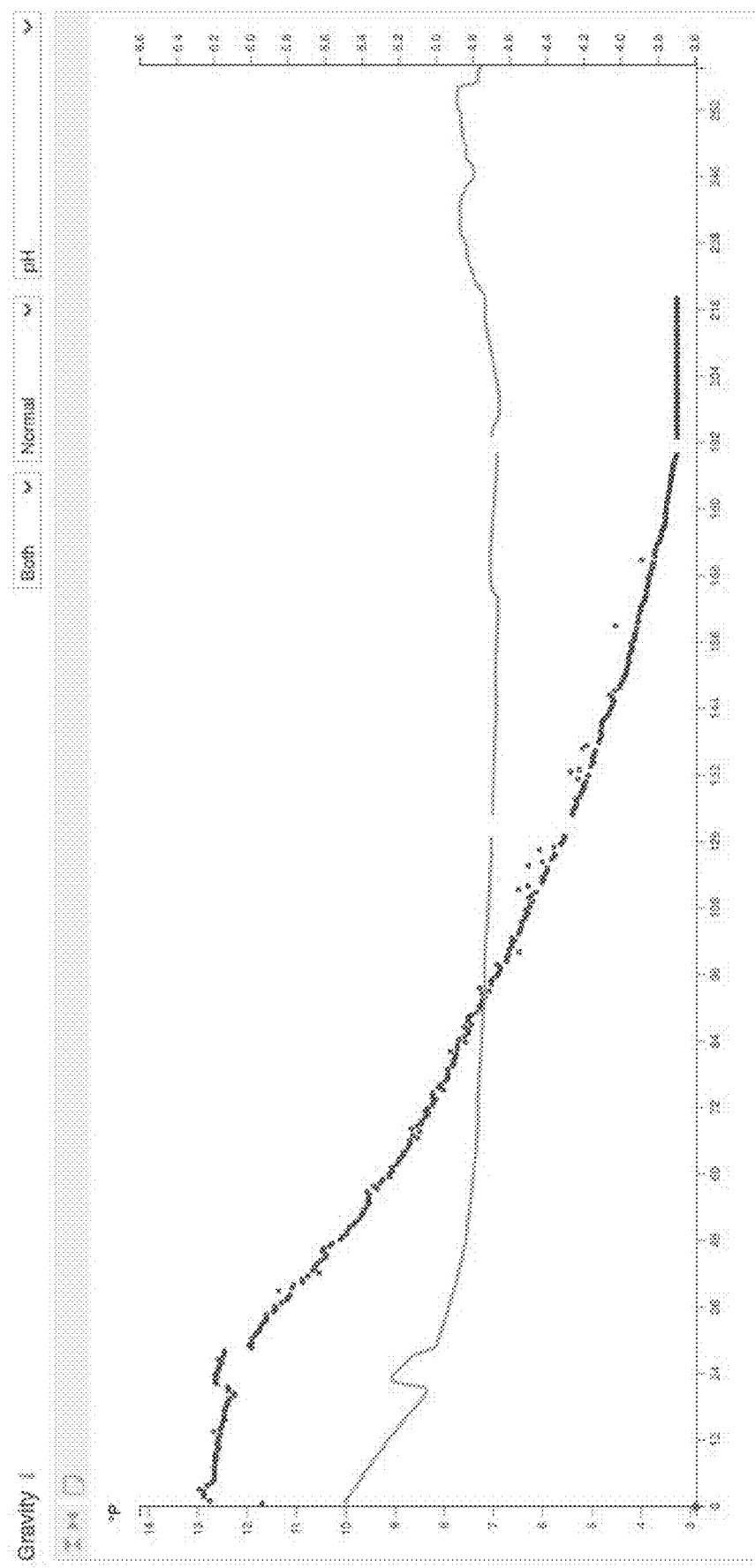
FIG. 7I is a graph showing addition approximately 22 hours after yeast was added to the fermentation, resulting in a gravity and pH increase, according to an example embodiment of the present disclosure.
Figure 7J:
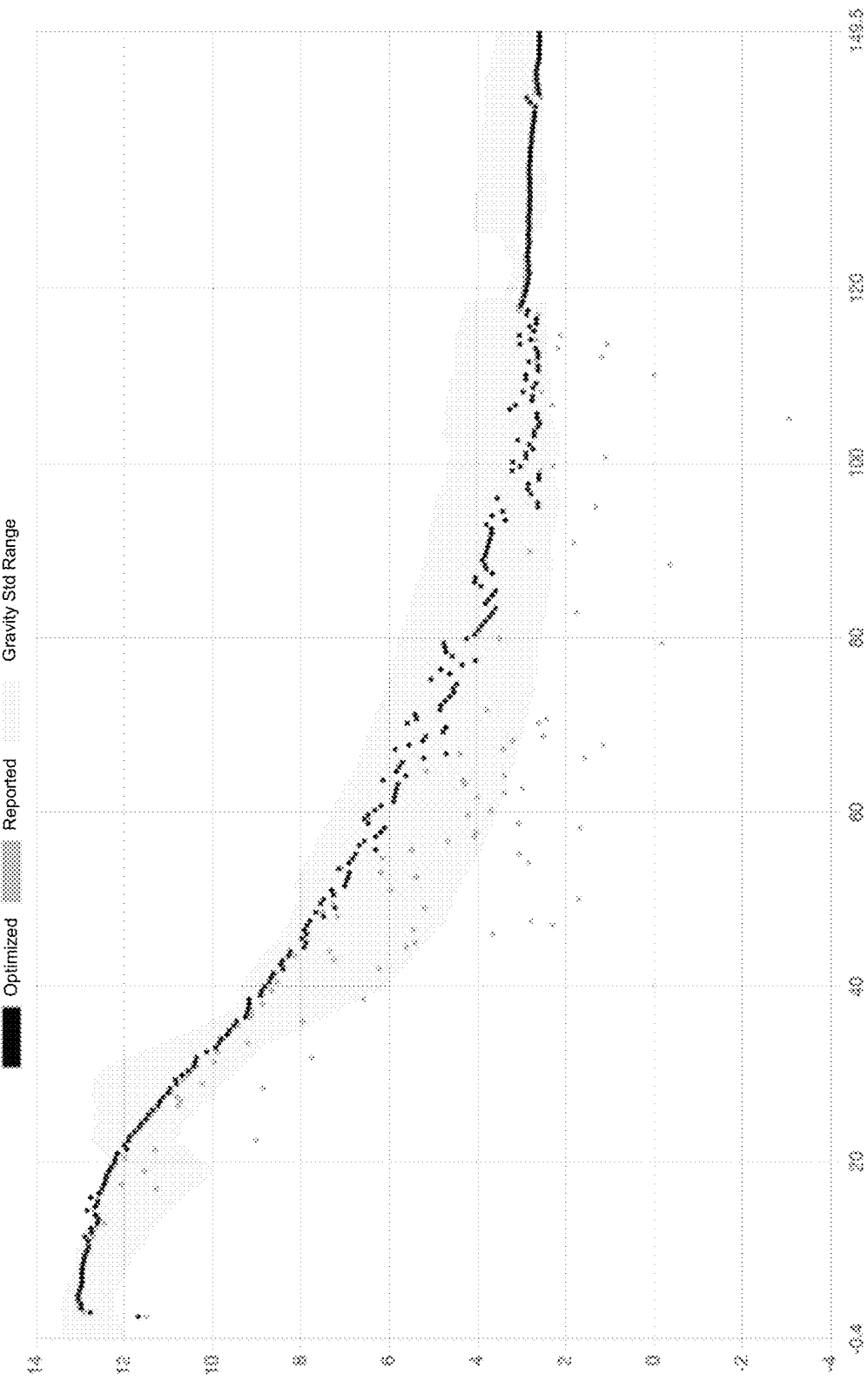
FIG. 7J is a plot showing filter range for optimization as determined by the standard deviation of optimized gravity for prior fermentations of the same beer brand, according to an example embodiment of the present disclosure.
Figure 7L:
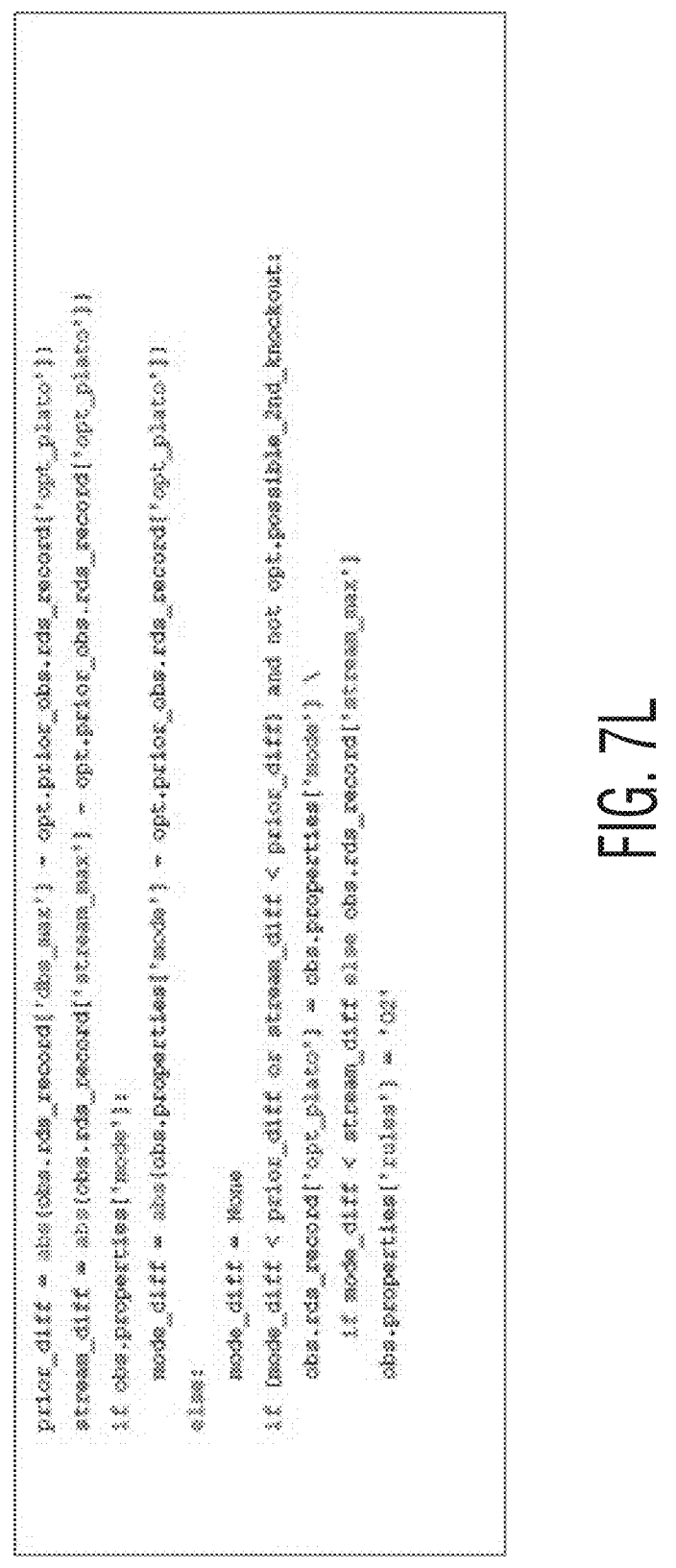
Figure 7M:
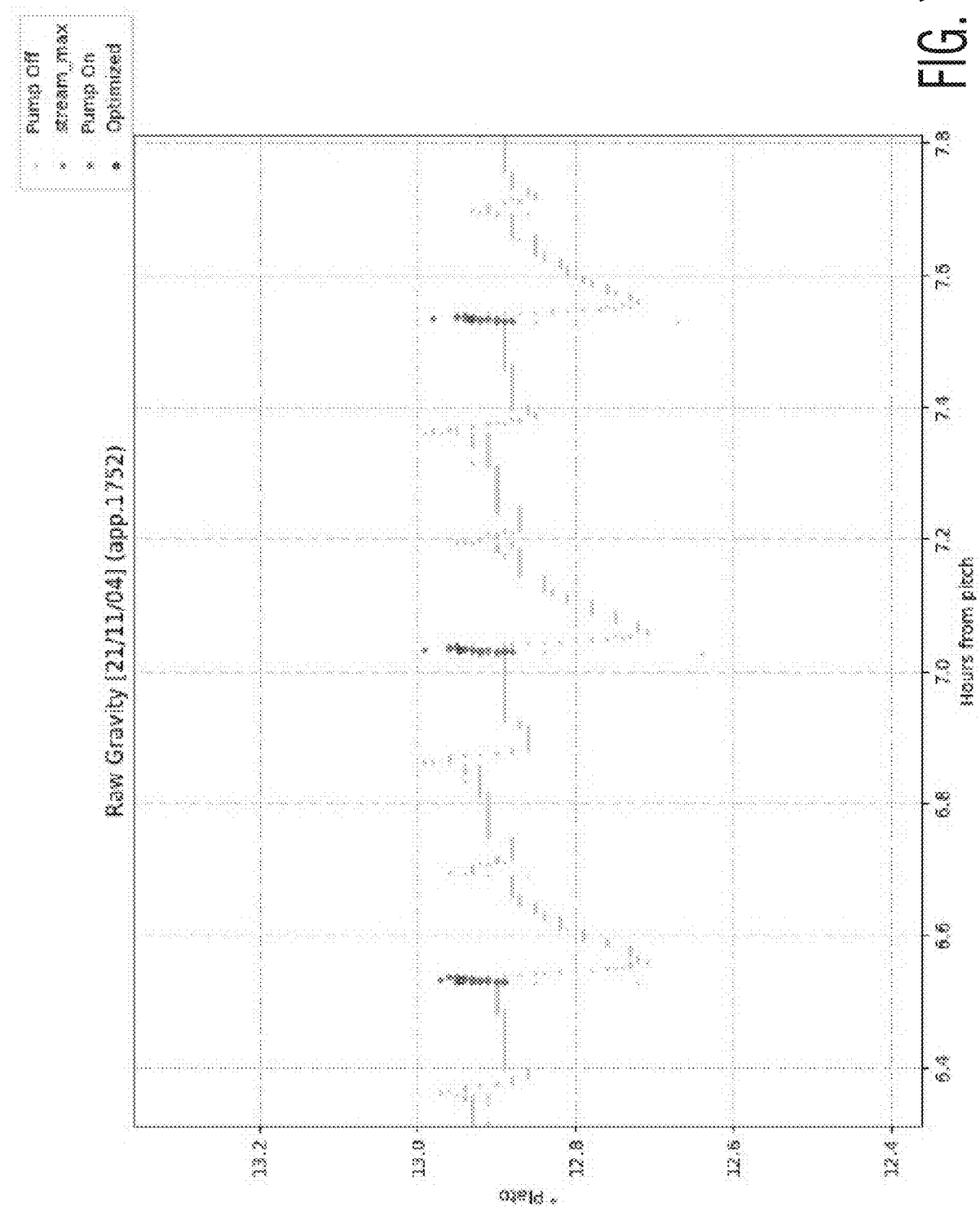
FIG. 7M is a plot of the available data points and resulting optimized value around this time point for the fermentation; mode is the mode of the pump on values, according to an example embodiment of the present disclosure.
Figure 70:
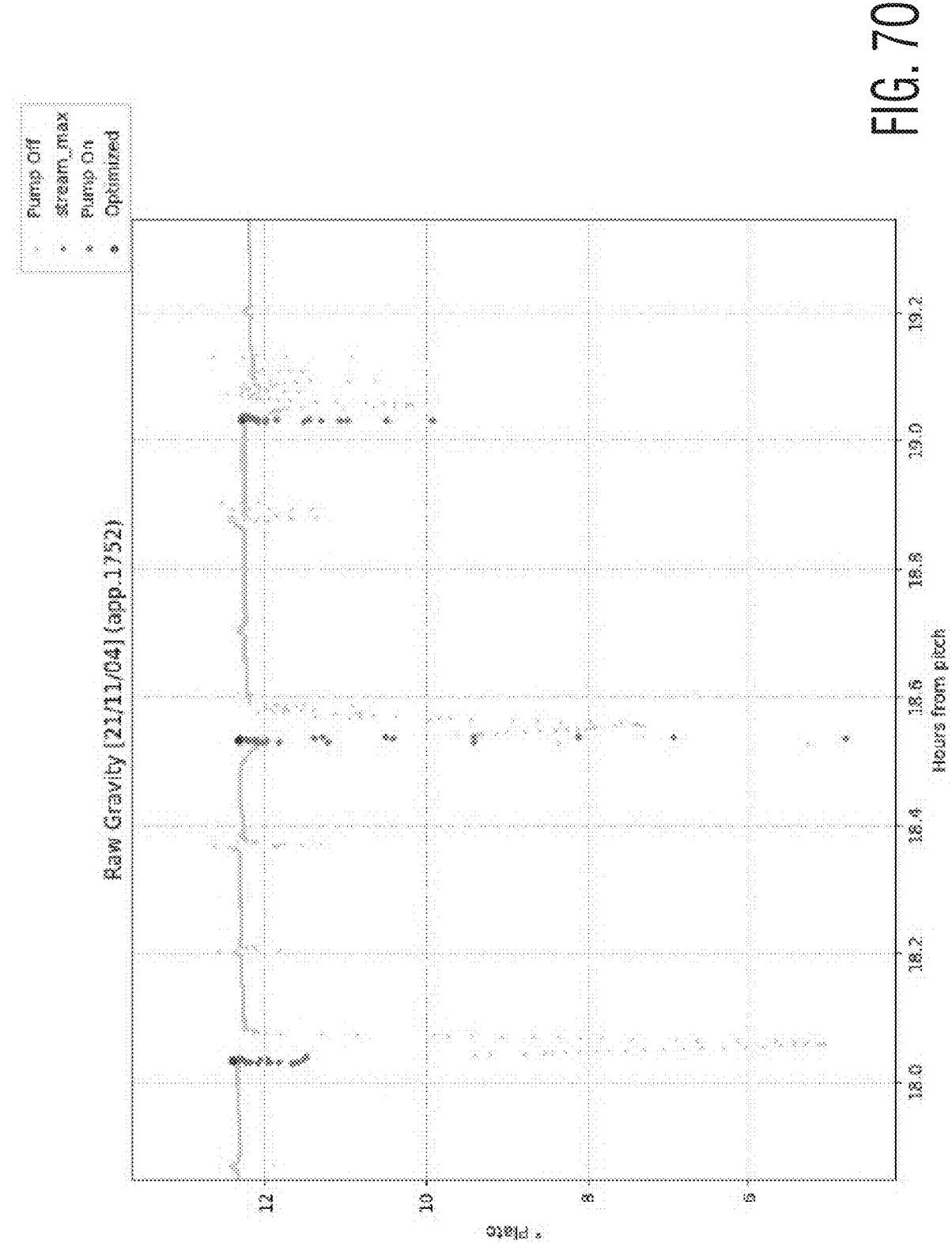
Figure 7Q:
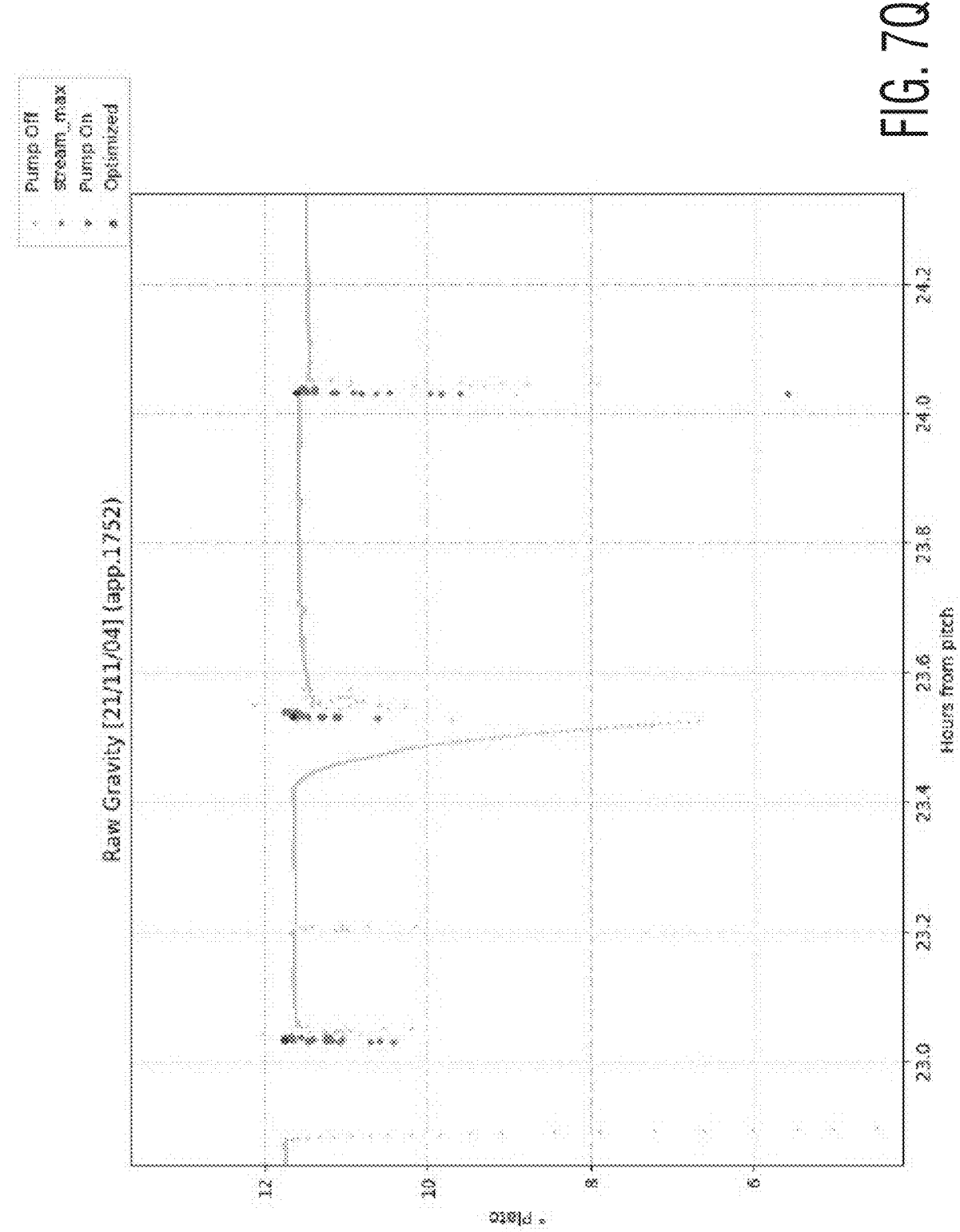
FIG. 7Q is a plot of the available data points and resulting optimized value around this time point for the fermentation; mode is the mode of the pump on values, according to an example embodiment of the present disclosure.
Figure 7S:
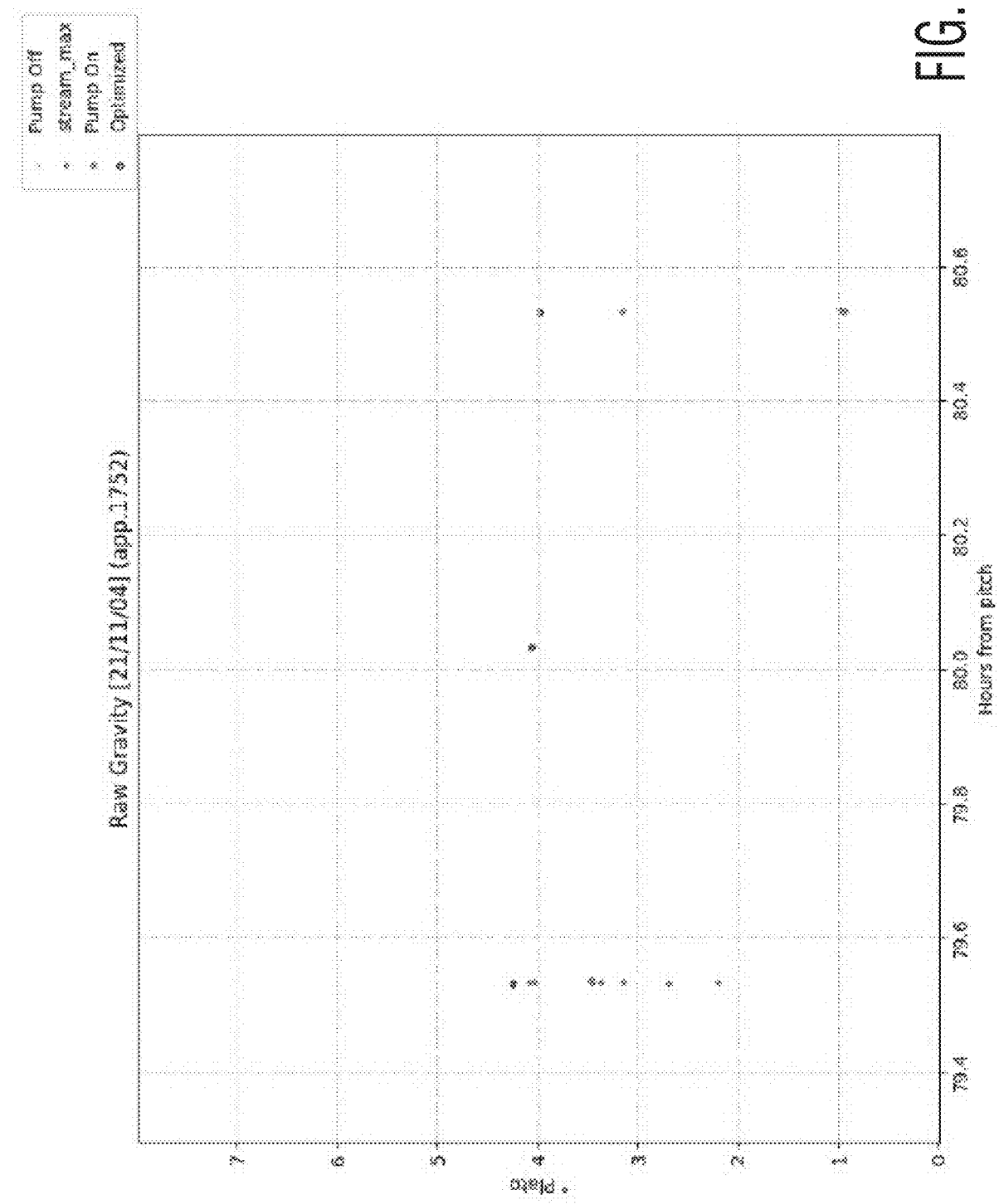
FIG. 7S is a plot of the available data points and resulting optimized value around this time point for the fermentation, according to an example embodiment of the present disclosure.
Figure 7T:
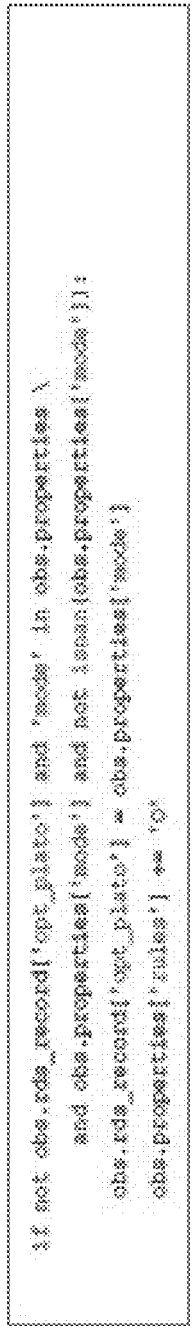
FIG. 7T is an example rule that can apply in phase 4, according to an example embodiment of the present disclosure.
Figure 7U:
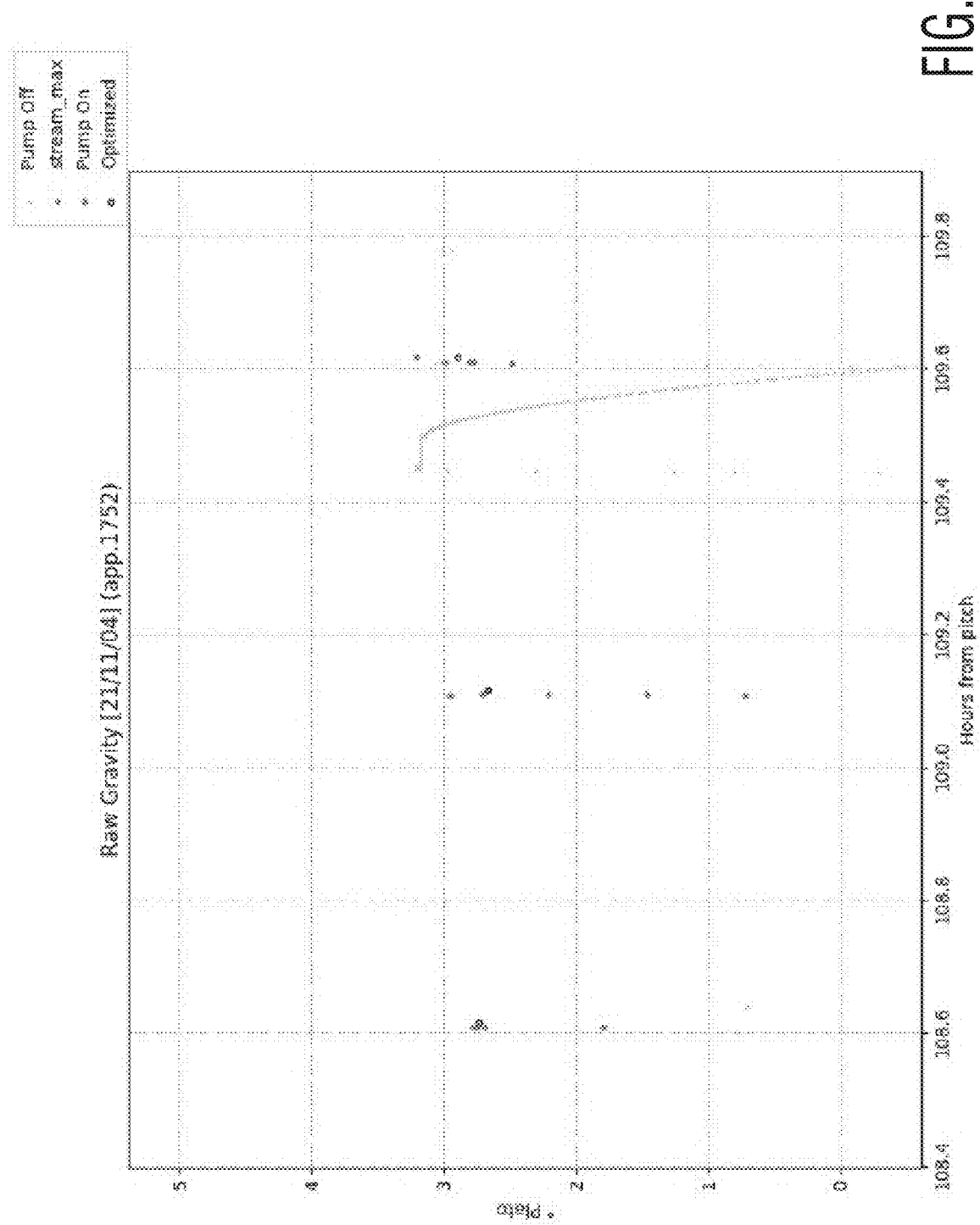

FIGS. 7G-7U show additional example details related to some of the elements defined in the algorithm flowchart of FIG. 6. The optimization process can be active while the fermentation is active and can process each measurement as it is reported. Thus, the process flow can be executed from time to time (e.g., once every 30 minutes, once every 20 to 40 minutes, or once any predetermined time) when a gravity reading is taken.

Example Fermentation Phase Definitions

Example fermentation phases referenced in the algorithm description are defined in FIG. 7G. FIG. 7G is a depiction of fermentation phase using the same dataset as Example 1 above. Phases are based on a model of expected attenuation, which is the decrease in gravity relative to starting gravity.

Example Gravity Data Source Definitions

The gravity data can be collected while one or more pumps are running, or when no pumps are running. The two data sources can be distinguished as follows:

Stream Data—these can be gravity readings taken while the density pump is not running.

Fluid in Motion Data—these can be readings taken while the density pump is running, and/or shortly (<10 second, any predetermined time) thereafter. There can be many (e.g., between 12 and 30, any predetermined amount) of these depending on firmware version for the sensor hub.

FIG. 7H is a depiction of individual gravity readings taken while the density pump is on vs. off. From the data collected in FIG. 7H, intermediate values can be calculated that may be used by rules in later calculations:

Reported value (this may be a single reported density reading based on calculations done in the firmware based only on fluid in motion data for the current reading.

Stream Max_This may be calculated as the maximum value measured from readings while the density pump is off at a chosen frequency within the measurement interval.

Pump On Max_This may be calculated as the maximum value measured while the density pump is running.

Additions Can Be Detected

At any point in a fermentation process, material may be added that alters the characteristics of the fluid. After the addition, measured gravity may change significantly due to the additional material rather than biological action by the yeast or other fermenting organism. Immediately after an addition, increase or decrease in gravity resulting from the addition must be distinguished from other sources of variability in gravity readings.

Additions may be detected via changes in physical parameters being measured other than gravity. These additional parameters may include one or more of pressure, temperature, pH, conductivity, or dissolved oxygen. FIG. 7I is a graph showing addition approximately 22 hours after yeast was added to the fermentation, resulting in a gravity and pH increase.

Current Filter Can Be Applied to Stream Data

Density data can contain a high degree of variability as depicted in the raw gravity data above. To reduce the impact of the variability on optimization calculations, readings can be filtered. At any given point during the fermentation, there can be an active range that can define potentially valid gravity readings. This range can depend on the current phase and/or starting gravity. For phase 1, for example, the valid range might be between 80% and 110% of starting gravity; any streaming gravity readings outside of this range can be filtered out of the dataset during this phase.

The filter range may be determined by comparison to historic data from prior fermentations using the same ingredients and process when comparison data matching the ingredients and process are known.

FIG. 7J is a plot showing filter range for optimization as determined by the standard deviation of optimized gravity for prior fermentations of the same beer brand. If comparable recipes and processes are not available, comparison across fermentations of similar style may be used to establish filter ranges, where style is a more generalized description of product category (e.g. Lager as a style of beer). FIG. 7K is a plot showing filter range for optimization as determined by the standard deviation of optimized gravity for prior fermentations of the same beer style.

Statistics Can Be Calculated for the Observation

The optimization algorithm can use a variety of standard statistics calculated based on the fluid in motion data and streaming data for the observation. These statistics can include any combination of:

- Number of observations within the current filter range;
- Maximum observed fluid in motion data value;
- 2nd largest fluid in motion data value;
- Mean fluid in motion data value' Mode of fluid in motion data values;
- Standard deviation of fluid in motion data values;
- Maximum stream data value that occurs at a frequency of 3 or higher in the prior 15 minutes; and/or
- These statistics can be calculated for each density observation.

Current Rules Can Apply to Define Optimized Value

The optimization process can proceed by applying a set of rules in a defined sequence, where the rule set can vary based on the phase of the fermentation. A rule can be a specific conditional or unconditional update to the optimized gravity value. For example, during several phases, the initial optimized gravity value can be the maximum observed fluid in motion data reading. In other phases, the initial optimized gravity value can be the mode of the observed fluid in motion readings. Most rules can be conditional; they can update the optimized gravity reading only if specific conditions are met.

Example Rule_Phase 0

FIG. 7L shows an example rule that can apply in phase 0 (and only in phase 0, in some aspects of the disclosure). It can determine whether to use the stream max or mode based on which is closer to the prior optimized reading Table A below sets forth the relevant data values for a sample time point where this rule may be applied; these data values are taken from the fermentation depicted in Example 1:

TABLE A

| phase | hours_from_pitch | opt_plato | stream_max | rules | mode |
|-------|------------------|-----------|------------|-------|-------|
| 0 | 6.53 | 12.94 | 12.97 | O2 | 12.94 |
|  | 6.70 |  |  |  |  |
|  | 6.87 |  |  |  |  |
| 0 | 7.03 | 12.95 | 12.99 | O2 | 12.95 |

In this example application of one phase 0 rule, at 7.03 hours from pitch, the optimized plato value is identified as the mode of values taken while the pump is running rather than the stream_max value. FIG. 7M is a plot of the available data points and resulting optimized value around this time point for the fermentation; mode is the mode of the pump on values.

Example Rule_Phase 1

FIG. 7N shows an example rule that can apply in phase 1. It can use the maximum reading taken when the pump is running. Table B below sets forth the relevant data values for a sample time point where this rule may be applied, values are taken from the fermentation depicted in example 1:

TABLE B

| phase | hours_from_pitch | plato | opt_plato | rules | dbs_max |
|-------|------------------|-------|-----------|-------|---------|
| 1 | 18.53 | 11.53 | 12.33 | M | 12.33 |

FIG. 7O is a plot of the available data points and resulting optimized value around this time point for the fermentation; mode is the mode of the pump on values.

Example Rule_Phase 2

FIG. 7P shows an example rule that can apply in phase 2. It can test whether the stream_max value for this observation is a more accurate reading for this optimization by testing its difference from the prior optimization vs. the difference of the existing optimization estimate for this observation. Table C below sets forth the relevant data values for a sample time point where this rule may be applied, values are taken from the fermentation depicted in example 1.:

TABLE C

| phase | hours_from_pitch | plato | opt_plato | stream_max | rules | dbs_max |
|-------|------------------|-------|-----------|------------|-------|---------|
| 2 | 23.03 | 11.71 | 11.76 | 11.78 | M | 11.76 |
|  | 23.20 |  |  |  |  |  |
|  | 23.37 |  |  |  |  |  |
| 2 | 23.53 | 11.62 | 11.66 | 11.66 | Mt | 11.77 |

FIG. 7Q is a plot of the available data points and resulting optimized value around this time point for the fermentation; mode is the mode of the pump on values.

Example Rule_Phase 3

FIG. 7R shows an example rule that can apply in phase 3. This rule can be conditional on whether some prior rules have been applied to this observation and can override the existing estimate of optimized gravity with an estimate based on a slope estimate based on average change in gravity per time period since phase 1 started.

Table D below sets forth the relevant data values for a sample time point where this rule may be applied, values are taken from the fermentation depicted in example 1. In this case, the optimized plato for the observation at hour 80.53 from pitch is based on the observation from 80.03 hours from pitch and the phase 1 average change (p1_slope).

TABLE D

| phase | hours_from_pitch | plato | opt_plato | stream_max | rules | dbs_max | dbs_valid | mode | p1_slope |
|---|---|---|---|---|---|---|---|---|---|
| 3 | 80.03<br>80.20<br>80.37 | 4.05 | | | M | 4.05 | 1 | | −0.07 |
| 3 | 80.53 | | 3.97 | | MSsq* | 3.16 | 1 | | −0.07 |

FIG. 7S is a plot of the available data points and resulting optimized value around this time point for the fermentation. There are no raw data readings in a valid range for this time period, so only the slope-based estimate for optimized gravity is shown.

Example Rule_Phase 4

FIG. 7T is an example rule that can apply in phase 4. This rule will assign the optimized plato estimate as the mode value if it exists and is a valid number.

Table D below sets forth the relevant data values for a sample time point where this rule is applied, values are taken from the fermentation depicted in example 1.

TABLE D

| phase | hours_from_pitch | opt_plato | stream_max | rules | dbs_max | dbs_valid | mode |
|---|---|---|---|---|---|---|---|
| 4 | 109.12 | 2.66 | | O | 2.95 | 6 | 2.662 |

FIG. 7U is a plot of the available data points and resulting optimized value around this time point for the fermentation; mode is the mode of the pump on values.

Slope Estimate Can Be Checked

During this phase, optimized results that are pure estimates (e.g., not based on analysis of measured results) can be accumulated until a sufficiently strong measured result that can be used to confirm the estimated results is obtained.

Points can be re-estimated with new anchor

If the accumulated estimated results need to be adjusted based on a new measured result, they can be updated. For example, assuming 24 hours into a fermentation, and the current estimated fermentation rate is 0.2 plato per hour and we're at 10 plato. If no valid gravity readings for the next six hours are obtained, the optimization algorithm can estimate a gravity decrease of 0.2 plato per hour over that period, so at 30 hours the optimized plato result can be 10−0.2 * 6, or 8.8 plato. If a strong valid gravity reading of 7.8 plato is obtained rather than the 8.8 estimated, the values over the 6 hour period that were purely estimation can be adjusted with a revised slope of (10−7.8/6), or 0.367 plato/hour for that period.

Phase Can Be Checked

During this phase, the attenuation of the current observation can be assessed and determine whether the result is a change in the fermentation phase. For fermentations with no additions, the phases can proceed in sequence (0-4). For fermentations with additions, the current phase can be reset. When a phase is updated, the optimization rules and phase gates can be adjusted based on what is appropriate for the phase. If a phase is reset to 0, this may not affect the current slope estimate. The current slope estimate can be a proxy for yeast activity, which may not be impacted by the addition of additional fermentable material.

Slope Esimate(s) May Be Udated

During phases 1-3, missing values may be estimated based on the current rate of change in the fermentation. In this step, the current estimated slope (e.g., rate of change in gravity) can be updated since the start of phase 1.

FIG. 8A, 8B, 8C, 8D, 8E, 8F, 8G, 8H, 8I, 8J, 8K, 8L, 8M, 8N, 8O 8P, 8Q, 8R, 8S, 8T, 8U, 8V, 8W, 8X, 8Y, 8Z, 8AA, 8BB, 8CC, 8DD, 8EE, 8FF, 8GG, 8HH, 8II, 8JJ, 8KK, 8LL, 8MM, 8NN, 8OO, 8PP, 8QQ, 8RR, BSS, BTT, 8UU, 8VV, 8WW, 8XX, 8YY, 8ZZ, 8AAA, RBBB, 8CCC, 8DDD, 8EEE, 8FFF, and 8GGG are, collectively, an example spreadsheet of the algorithmic detailed results of the graph of example 1 in FIGS. 7A to 7U.

Conclusion

While the present disclosure has been discussed in terms of certain embodiments, it should be appreciated that the present disclosure is not so limited. The embodiments are explained herein by way of example, and there are numerous modifications, variations and other embodiments that may be employed that would still be within the scope of the present disclosure.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. The examples set forth in this document are for illustrative purposes and all elements of the example may not be required or exhaustive. Accordingly, other implementations are within the scope of the following claims. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter. For example, the steps and/or limitations in the specification, drawings, and/or claims may be performed in an order other than the order set forth in the specification, drawings, and/or claims.

In addition, it should be understood that any figures which highlight the functionality and advantages are presented for example purposes only. The disclosed methodology and system are each sufficiently flexible and configurable such that they may be utilized in ways other than that shown. For example, other steps may be provided, or steps may be eliminated, from the described flows, and other components may be added to, or removed from, the described systems.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112(f). Claims that do not expressly include the phrase "means for" or "step for" are not to be interpreted under 35 U. S. C. 112(f).

The invention claimed is:

1. A computerized system for continuous monitoring, comprising:
    an inlet allowing fluid to enter a device;
    an outlet allowing fluid to exit the device;
    a first fluid path connected to the inlet, a sensor manifold, and the outlet, the sensor manifold comprising one or more sensors for sensing one or more characteristics of a fluid;
    a second fluid path connected to the inlet, a second sensor component, and the outlet, the second sensor component comprising a density sensor for sensing the density of the fluid;
    a gravity measurement module for measuring a change in the gravity of the fluid using the density of the fluid;
    varying timing of pumping and the measuring to increase accuracy of density measurement to calculate the gravity measurement in order to determine a current level of characteristics in the fluid,
    obtaining data while the fluid is in motion;
    obtaining data while the fluid is at rest;
    obtaining density observations;
    analyzing multiple measurements taken while the fluid is at motion and at rest within a defined period to calculate an estimated gravity range;
    calculating statistics for multiple density observations using the fluid at rest observations and the fluid in motion observations;
    determining a rule set to use from a predetermined group of rule sets using the calculated statistics; and
    using the rule set to define an estimated value of gravity of the fluid based on a phase of fermentation.

2. The computerized system of claim 1, wherein the timing of the measuring is adjusted based on a degree of escaped gas present in the fluid.

3. The computerized system of claim 1, wherein the characteristics comprise two or more of pH, fluid temperature, ambient temperature, fluid pressure, fluid conductivity, dissolved oxygen, cell counts, cell viability, turbidity, capacitance, concentration of organic compounds, and $CO_2$ concentration.

4. The computerized system of claim 1, wherein the sensor manifold comprises two or more of a pH sensor, an ambient temperature sensor, a fluid temperature sensor, a fluid pressure sensor, a fluid conductivity sensor, a dissolved oxygen sensor, a sensor for measuring cell counts, cell viability, turbidity, capacitance, concentration of organic compounds, and $CO_2$ concentration.

5. The computerized system of claim 1, further comprising:
    receiving measurements measured by the one or more sensors of the sensor manifold in real-time or near real-time;
    receiving measurements measured by the density sensor in real-time or near real-time; and
    calculating the gravity of the fluid via the received measurements.

6. The computerized system of claim 1, further comprising:
    measuring the one or more characteristics of the fluid via the one or more sensors of the sensor manifold at a predetermined rate; and
    reporting the density of the fluid via the density sensor at after a predetermined time period based on measurements taken continuously during the predetermined time period.

7. The computerized system of claim 6, further comprising re-estimating a gravity range by analyzing measurements when an anchor point is obtained.

8. The system of claim 6, wherein the predetermined rate is approximately 5 minutes to approximately 15 minutes.

9. The system of claim 6, wherein the predetermined time period is approximately 20 to 40 minutes.

10. The system of claim 6, wherein a reading is reported after the predetermined time period based on density measurements that are taken continuously during the predetermined time period.

11. The system of claim 10, wherein hundreds of individual measurements are taken during the predetermined time period to provide a single estimate for the predetermined time period.

12. The computerized system of claim 1, wherein the varying of the timing of the measuring comprises:
    identifying a level of escaped gas in the fluid during one or more periods;
    identifying which of the one or more periods allow for more accurate measurements of the one or more characteristic by the sensor manifold, wherein periods that include a lower level of escaped gas are more accurate than periods that include a higher level of escaped gas;
    identifying which of the measurements during a period before pumping, during pumping, or after pumping, or any combination thereof, that represents a most accurate measurement of fluid density by the density sensor, wherein a period that includes a lower levels of escaped gas is more accurate than a period that includes a higher levels of escaped gas;
    pumping the fluid to the sensor manifold via the first fluid path and measuring one or more fluid characteristics during an identified period; and
    pumping the fluid to the density sensor via the second fluid path and measuring the fluid density during an identified period.

13. The computerized system of claim 1, further comprising:
    determining if the measured value of gravity is within a predetermined range of the estimated value of gravity.

14. The computerized system of claim 1, wherein the statistics comprise:
    a number of observations within a current filter range;
    a maximum observed fluid in motion data value;
    a $2^{nd}$ largest fluid in motion data value;
    a mean fluid in motion data value;
    a mode of fluid in motion data values;
    a standard deviation of fluid in motion data values; or
    a maximum fluid at rest data value that occurs at a frequency of 3 or higher in a prior 15 minutes; or
    any combination thereof.

15. The system of claim 14, wherein the filter range is established via a comparison of optimized gravity of prior fermentations of a same brand.

16. The system of claim 14, wherein the filter range is established via a comparison of optimized gravity of prior fermentations of a similar style or similar brand or a combination thereof.

17. A method for continuous monitoring, comprising:
providing a computerized system for continuous monitoring, comprising:
an inlet allowing fluid to enter a device;
an outlet allowing fluid to exit the device;
a first fluid path connected to the inlet, a sensor manifold, and the outlet, the sensor manifold comprising one or more sensors for sensing one or more characteristics of a fluid;
a second fluid path connected to the inlet, a second sensor component, and the outlet, the second sensor component comprising a density sensor for sensing the density of the fluid; and
a gravity measurement module for measuring a change in the gravity of the fluid using the density of the fluid;
varying timing of pumping and the measuring to increase the accuracy of density measurement to calculate the gravity measurement in order to determine a current level of characteristics in the fluid,
obtaining data while the fluid is in motion;
obtaining data while the fluid is at rest;
obtaining density observations;
analyzing multiple measurements taken while the fluid is at motion and at rest within a defined period to calculate an estimated gravity range;
calculating statistics for multiple density observations using the fluid at rest observations and the fluid in motion observations;
determining a rule set to use from a predetermined group of rule sets using the calculated statistics; and
using the rule set to define an estimated value of gravity of the fluid based on a phase of fermentation.

18. The method of claim 17, wherein the timing of the measuring is adjusted based on the degree of escaped gas present in the fluid.

19. The method of claim 17, wherein the characteristics comprise two or more of pH, fluid temperature, ambient temperature, fluid pressure, fluid conductivity, dissolved oxygen, cell counts, cell viability, turbidity, capacitance, concentration of organic compounds, and $CO_2$ concentration.

20. The method of claim 17, wherein the sensor manifold comprises two or more of a pH sensor, an ambient temperature sensor, a fluid temperature sensor, a fluid pressure sensor, a fluid conductivity sensor, a dissolved oxygen sensor, a sensor for measuring cell counts, cell viability, turbidity, capacitance, concentration of organic compounds, and $CO_2$ concentration.

21. The method of claim 17, further comprising:
receiving measurements measured by the one or more sensors of the sensor manifold in real-time or near real-time;
receiving measurements measured by the density sensor in real-time or near real-time; and
calculating the gravity of the fluid via the received measurements.

22. The method of claim 17, further comprising:
measuring the one or more characteristics of the fluid via the one or more sensors of the sensor manifold at a predetermined rate; and
reporting the density of the fluid via the density sensor at after a predetermined time period based on measurements taken continuously during the predetermined time period.

23. The method of claim 22, further comprising re-estimating a gravity range by analyzing measurements when an anchor point is obtained.

24. The method of claim 22, wherein the predetermined rate is approximately 5 minutes to approximately 15 minutes.

25. The method of claim 22, wherein the predetermined time period is approximately 20 to 40 minutes.

26. The method of claim 22, wherein a reading is reported after the predetermined time period based on density measurements that are taken continuously during the predetermined time period.

27. The method of claim 26, wherein hundreds of individual measurements are taken during the predetermined time period to provide a single estimate for the predetermined time period.

28. The method of claim 17, wherein the varying of the timing of the measuring comprises:
identifying a level of escaped gas in the fluid during one or more periods;
identifying which of the one or more periods allow for more accurate measurements of the one or more characteristic by the sensor manifold, wherein periods that include a lower level of escaped gas are more accurate than periods that include a higher level of escaped gas;
identifying which of the measurements during a period before pumping, during pumping, or after pumping, or any combination thereof, that represents a most accurate measurement of fluid density by the density sensor, wherein a period that includes a lower levels of escaped gas is more accurate than a period that includes a higher levels of escaped gas;
pumping the fluid to the sensor manifold via the first fluid path and measuring one or more fluid characteristics during an identified period; and
pumping the fluid to the density sensor via the second fluid path and measuring the fluid density during an identified period.

29. The method of claim 17, further comprising:
determining if the measured value of gravity is within a predetermined range of the estimated value of gravity.

30. The method of claim 17, wherein the statistics comprise:
a number of observations within a current filter range;
a maximum observed fluid in motion data value;
a $2^{nd}$ largest fluid in motion data value;
a mean fluid in motion data value
a mode of fluid in motion data values;
a standard deviation of fluid in motion data values; or
a maximum fluid at rest data value that occurs at a frequency of 3 or higher in a prior 15 minutes; or
any combination thereof.

31. The method of claim 30, wherein the filter range is established via a comparison of optimized gravity of prior fermentations of a same brand.

32. The method of claim 30, wherein the filter range is established via a comparison of optimized gravity of prior fermentations of a similar style or similar brand or a combination thereof.

* * * * *